United States Patent
Emanuel et al.

(10) Patent No.: US 11,021,511 B2
(45) Date of Patent: Jun. 1, 2021

(54) CYCLIC DINUCLEOTIDES AS STING AGONISTS

(71) Applicant: Janssen Biotech, Inc., Horsham, PA (US)

(72) Inventors: Stuart Emanuel, Doylestown, PA (US); Mark Richter, Wayne, PA (US); Peter J. Connolly, New Providence, NJ (US); James Patrick Edwards, Ambler, PA (US); Guangyi Wang, Irvine, CA (US); Santhosh Kumar Thatikonda, Fremont, CA (US); Leonid Beigelman, San Mateo, CA (US); Minghong Zhong, San Bruno, CA (US); Gilles Bignan, Bridgewater, NJ (US)

(73) Assignee: Janssen Biotech, Inc., Horsham, PA (US)

(*) Notice: Subject to any disclaimer, the term of this patent is extended or adjusted under 35 U.S.C. 154(b) by 0 days.

(21) Appl. No.: 16/478,864

(22) PCT Filed: Jan. 26, 2018

(86) PCT No.: PCT/IB2018/050497
§ 371 (c)(1),
(2) Date: Jul. 18, 2019

(87) PCT Pub. No.: WO2018/138684
PCT Pub. Date: Aug. 2, 2018

(65) Prior Publication Data
US 2019/0375781 A1  Dec. 12, 2019

Related U.S. Application Data

(60) Provisional application No. 62/454,131, filed on Feb. 3, 2017, provisional application No. 62/451,285, filed on Jan. 27, 2017.

(51) Int. Cl.
*A61K 31/70* (2006.01)
*A01N 43/04* (2006.01)
(Continued)

(52) U.S. Cl.
CPC .............. *C07H 21/00* (2013.01); *A61P 31/12* (2018.01); *A61P 35/00* (2018.01); *A61K 31/708* (2013.01);
(Continued)

(58) Field of Classification Search
None
See application file for complete search history.

(56) References Cited

U.S. PATENT DOCUMENTS 6,531,491 B1   3/2003  Kania et al.
8,383,796 B2   2/2013  Korman et al.
(Continued)

FOREIGN PATENT DOCUMENTS

WO    WO 2000/41474 A2    7/2000
WO    WO 2001/002369 A2   1/2001
(Continued)

OTHER PUBLICATIONS

Tiwari et al. Nucleosides, Nucleotides and Nucleic Acids (2009), vol. 28, Nos. 5-7, pp. 657-677.*
(Continued)

*Primary Examiner* — Patrick T Lewis
(74) *Attorney, Agent, or Firm* — BakerHostetler

(57) ABSTRACT

Disclosed are compounds, compositions and methods for treating of diseases, syndromes, or disorders that are affected by the modulation of STING. Such compounds are represented by Formula (I) as follows:

Formula (I)

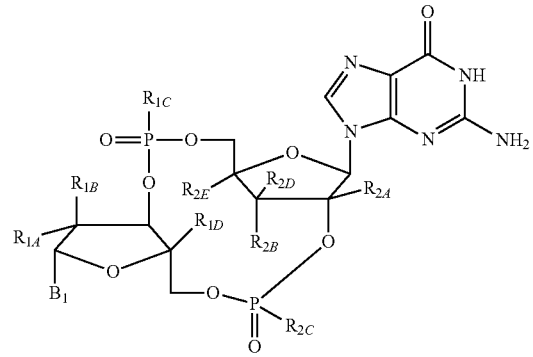

wherein $R_{1A}$, $R_{1B}$, $R_{1C}$, $R_{1D}$, $B_1$, $R_{2A}$, $R_{2B}$, $R_{2C}$, $R_{2D}$, and $R_{2E}$ are defined herein
and Formula (II)

Formula (II)

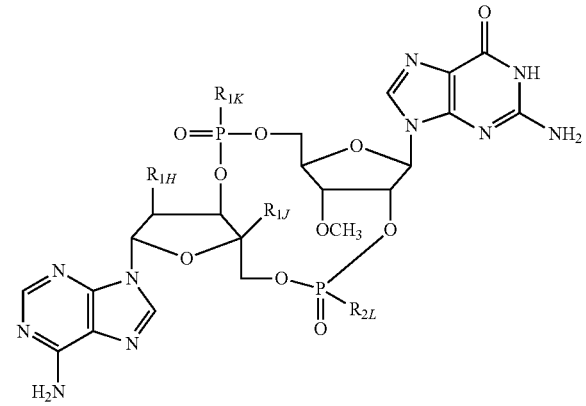

wherein $R_{1H}$, $R_{1K}$, $R_{1J}$, and $R_{2L}$ are defined herein.

14 Claims, No Drawings

(51) Int. Cl.
*C07H 21/00* (2006.01)
*A61P 31/12* (2006.01)
*A61P 35/00* (2006.01)
*A61K 31/708* (2006.01)
*A61K 31/7084* (2006.01)
*A61K 31/7076* (2006.01)

(52) U.S. Cl.
CPC ...... *A61K 31/7076* (2013.01); *A61K 31/7084* (2013.01)

(56) References Cited

U.S. PATENT DOCUMENTS

| | | | |
|---|---|---|---|
| 2006/0167241 A1* | 7/2006 | Hayakawa | C07H 19/10 536/26.2 |
| 2010/0203056 A1 | 8/2010 | Irving et al. | |
| 2013/0017199 A1 | 1/2013 | Langermann | |
| 2014/0341976 A1 | 11/2014 | Dubensky et al. | |
| 2015/0056224 A1 | 2/2015 | Dubensky et al. | |
| 2016/0068560 A1 | 3/2016 | Patel et al. | |
| 2016/0287623 A1 | 10/2016 | Gajewski et al. | |
| 2017/0044206 A1 | 2/2017 | Altman et al. | |
| 2017/0158724 A1 | 6/2017 | Adams et al. | |
| 2018/0002369 A1 | 1/2018 | Biggadike et al. | |
| 2018/0186828 A1 | 7/2018 | Biggadike et al. | |
| 2018/0230177 A1 | 8/2018 | Zhong et al. | |
| 2019/0062365 A1 | 2/2019 | Katibah et al. | |

FOREIGN PATENT DOCUMENTS

| | | |
|---|---|---|
| WO | WO 2002/010192 A2 | 2/2002 |
| WO | WO 2002/068470 A2 | 9/2002 |
| WO | WO 2010/027827 A2 | 3/2010 |
| WO | WO 2010/077634 A1 | 7/2010 |
| WO | WO 2011/066342 A2 | 6/2011 |
| WO | WO 2013/019906 A1 | 2/2013 |
| WO | WO 2014/179335 A1 | 11/2014 |
| WO | WO 2014/189805 A1 | 11/2014 |
| WO | WO 2014/189806 A1 | 11/2014 |
| WO | WO 2015/077354 A1 | 5/2015 |
| WO | WO 2015/185565 A1 | 12/2015 |
| WO | WO 2016/120305 A1 | 8/2016 |
| WO | WO 2017/027646 A1 | 2/2017 |
| WO | WO 2017/075477 A1 | 5/2017 |
| WO | WO 2017/093933 A1 | 6/2017 |
| WO | WO 2017/161349 A1 | 9/2017 |
| WO | WO 2017/186711 A1 | 11/2017 |

OTHER PUBLICATIONS

Guo, Fang, Yanxing Han, Xuesen Zhao, Jianghua Wang, Fei Liu, Chunxiao Xu, Lai Wei et al. "STING agonists induce an innate antiviral immune response against hepatitis B virus." Antimicrobial agents and chemotherapy 59, No. 2 (2015): 1273-1281.*
Chang et al. Antiviral Research (2015), vol. 121, pp. 152-159.*
Lioux et al. Journal of Medicinal Chemistry (2016), vol. 59, pp. 10253-10267.*

International Search Report relating to International Patent Application No. PCT/IB2018/050497, filed Jan. 26, 2018. Date of Mailing of International Search Report: dated Jun. 11, 2018.
Written Opinion of the International Searching Authority relating to International Patent Application no. PCT/IB2018/050497, filed Jan. 26, 2018. Date of Mailing of International Search Report: dated Jun. 11, 2018.
Beckett et al., "A minimal peptide substrate in biotin holoenzyme synthetase-catalyzed biotinylation.", Protein Science, 1999, pp. 921-929, vol. 8.
Bhat, N. and Fitzgerald, K.A., "Recognition of Cytosolic DNA by cGAS and other STING-dependent sensors.", Eur J Immunol., Mar. 2014, pp. 634-640, vol. 44(3).
Chen et al. "Activation of State by STING Is Critical for Antiviral Innate Immunity.", Cell, Oct. 14, 2011, pp. 433-446, vol. 147.
Corrales et al., "Direct activation of STING in the tumor microenvironment leads to potent and systemic tumor regression and immunity.", Cell Reports, May 19, 2015, pp. 1018-1030, vol. 11.
Danilchanka, O. and Mekalanos, JJ., "Cyclic Dinucleotides and the Innate Immune Response.", Cell, Aug. 29, 2013, pp. 962-970, vol. 154.
Guo et al., "STING Agonists Induce an Innate Antiviral Immune Response against Hepatitis B Virus.", Antimicrobial Agents and Chemotherapy, Feb. 2015, pp. 1273-1281, vol. 59(2).
Konno et al., "Cyclic dinucleotides trigger ULK1 (ATG1) phosphorylation of STING to prevent sustained innate immune signaling.", Cell, Oct. 24, 2013, pp. 688-698, vol. 155.
Liu et al., "Phosphorylation of innate immune adaptor proteins MAVS, STING, and TRIF induces IRF3 activation.", Science, Mar. 13, 2015, pp. 2630-2637, vol. 347(6227).
Liu et al., "Systematic identification of type I and type II interferon-induced antiviral factors.", Proc. Natl. Acad. Sci., Mar. 13, 2012, pp. 4239-4244, vol. 109(11).
Louix et al., "Design, Synthesis, and Biological Evaluation of Novel Cyclic Adenosine-Inosine Monophosphate (cAIMP) Analogs That Activate Stimulator of Interferon Genes.", J. Med. Chem., Nov. 4, 2016, pp. 10253-10267, vol. 59(22).
Marabelle et al., "Intratumoral Immunization: A New Paradigm for Cancer Therapy.", Clinical Cancer Research, Apr. 1, 2014, pp. 1747-1756, vol. 20(7).
Sun et al., "Cyclic GMP-AMP Synthase Is a Cytosolic DNA Sensor That Activates the Type I Interferon Pathway.", Science, Feb. 15, 2013, pp. 786-791, vol. 339.
Van der Jeught et al., "Targeting the tumor microenviroment to enhance antitumor immune responses.", Oncotarget, Dec. 26, 2014, pp. 1359-1381, vol. 6(3).
Wu et al., "Novel Phosphorylation Sites in the S. cerevisiae Cdc13 Protein Reveal New Targets for Telomere Length Regulation.", Journal of Proteome Research, 2013, pp. 316-327, vol. 12.
Yi et. al., "Single Nucleotide Polymorphisms of Human STING can affect innate immune response to cyclic dinucleotides.", PLOS ONE, Oct. 2013, pp. 1-15, vol. 8(10), e77846.
Zhang et al., "Cyclic GMP-AMP Containing Mixed Phosphodiester Linkages Is An Endogenous High-Affinity Ligand for STING.", Molecular Cell, Jul. 25, 2013, pp. 226-235, vol. 51.
Zhong et al., "The Adaptor Protein MITA Links Virus-Sensing Receptors to IRF3 Transcription Factor Activation.", Immunity, Oct. 17, 2008, pp. 538-550, vol. 29.

* cited by examiner

CYCLIC DINUCLEOTIDES AS STING AGONISTS

CROSS-REFERENCE TO RELATED APPLICATIONS

This Application is a U.S. national stage of PCT Application No. PCT/IB2018/050497, filed Jan. 26, 2018, which claims priority to U.S. Provisional Patent Application No. 62/451,285, filed Jan. 27, 2017 and U.S. Provisional Patent Application No. 62/454,131, filed Feb. 3, 2017; which are hereby incorporated by reference in their entireties.

FIELD OF THE INVENTION

The present invention relates to novel compounds which are STING (Stimulator of Interferon Genes) agonists and are useful for the treatment of disorders that are affected by the modulation of the STING protein. The invention also relates to pharmaceutical compositions comprising one or more of such compounds, processes to prepare such compounds and compositions, and use of such compounds or pharmaceutical compositions for the treatment of various diseases, syndromes and disorders. The invention may be involved in the activation of the downstream signaling pathway, further resulting in the activation of second messengers and growth factors, and the production of interferon involved in the innate and adaptive immunity. More particularly, the present invention relates to the use of such compounds or pharmaceutical compositions for the treatment of various infections, diseases, syndromes and disorders including, but not limited to, melanoma, colon cancer, breast cancer, prostate cancer, lung cancer, fibrosarcoma, and antiviral therapy.

BACKGROUND OF THE INVENTION

STING (stimulator of interferon genes), also known as TMEM173, MITA, MPYS, and ERIS, is a transmembrane receptor located inside the cell and a key sensor of cytosolic nucleic acids (Zhong B, et al. "The Adaptor Protein MITA Links Virus-Sensing Receptors to IRF3 Transcription Factor Activation". *Immunity.* 2008. vol. 29: 538-550). Recent studies have revealed the biology of STING and its role in mobilizing an innate immune response resulting in robust antitumor activity in mouse models. Activation of the STING pathway results in production of Type I interferons (mainly IFN-α and IFN-β) induced through the IRF3 (interferon regulatory factor 3) pathway. Activation of IRF3 is thought to be mediated by TBK1 that recruits and phosphorylates IRF3 thus forming an IRF3 homodimer capable of entering the nucleus to transcribe type I interferon and other genes (Liu S, et al. "Phosphorylation of innate immune adaptor proteins MAVS, STING, and TRIF induces IRF3 activation" *Science.* 2015: 2630-2637). TBK1 also activates the nuclear factor kappa-light-chain-enhancer of activated B cells pathway which leads to production of pro-inflammatory cytokines (IL-1a, IL-1β, IL-2, IL-6, TNF-α, etc.), via the oncogenic transcription factor NF-κB. In addition, STING activates STAT6 (signal transducer and activator of transcription 6) to induce (Th2-type), increase (IL-12) or decrease (IL-10) production of various cytokines, including the chemokines CCL2, CCL20, and CCL26 (Chen H, et al. "Activation of STAT6 by STING Is Critical for Antiviral Innate Immunity" *Cell.* 2011, vol. 14: 433-446). Direct phosphorylation of STING on Ser366 upon activation has also been reported to occur through TBK1 or ULK1 (Corrales, L. et al "Direct activation of STING in the tumor microenvironment leads to potent and systemic tumor regression and immunity" *Cell Reports,* 2015, vol. 11: 1-13; Konno, H. et al. "Cyclic dinucleotides trigger ULK1 (ATG1) phosphorylation of STING to prevent sustained innate immune signaling" *Cell,* 2013, vol. 155: 688-698).

The natural ligand that binds to and activates STING (2',3')cyclic guanosine monophosphate-adenosine monophosphate (2',3'-cGAMP) and the enzyme responsible for its synthesis (cGAS, also known as C6orf150 or MB21D1) have been elucidated providing an opportunity to modulate this pathway. cGAMP is a high affinity ligand for STING produced in mammalian cells that serves as an endogenous second messenger to activate the STING pathway. It is a cyclic dinucleotide with a unique 2',3' linkage produced by cGAS in the presence of exogenous double-stranded DNA (e.g. that released by invading bacteria, viruses or protozoa) or of self-DNA in mammals (Wu et al., 2013; Sun, L. et al. "Cyclic GMP-AMP Synthase Is a Cytosolic DNA Sensor That Activates the Type I Interferon Pathway" *Science,* 2013, vol. 339: 786-791; Bhat N and Fitzgerald K A. "Recognition of Cytosolic DNA by cGAS and other STING-dependent sensors". *Eur J Immunol.* 2014 March; 44(3): 634-40). STING activation can also occur through binding of exogenous (3',3) cyclic dinucleotides (c-di-GMP, c-di-AMP and 3'3'-cGAMP) that are released by invading bacteria (Zhang X, et al. "Cyclic GMP-AMP Containing Mixed Phosphodiester Linkages Is An Endogenous High-Affinity Ligand for STING" *Molecular Cell,* 2013, vol. 51: 226-235; Danilchanka, O and Mekalanos, J J. "Cyclic Dinucleotides and the Innate Immune Response" *Cell.* 2013. vol. 154: 962-970).

Activation of the STING pathway triggers an immune response that results in generation of specific killer T-cells that can shrink tumors and provide long lasting immunity so they do not recur. The striking antitumor activity obtained with STING agonists in preclinical models has generated a high level of excitement for this target and small molecule compounds that can modulate the STING pathway have potential to treat both cancer and reduce autoimmune diseases.

Activation of the STING pathway also contributes to an antiviral response. Loss-of-functional response, either at the cellular or organism level, demonstrates an inability to control viral load in the absence of STING. Activation of the STING pathway triggers an immune response that results in antiviral and proinflammatory cytokines that combat the virus and mobilize the innate and adaptive arms of the immune system. Ultimately, long-lasting immunity is developed against the pathogenic virus. The striking antiviral activity obtained with STING agonists in preclinical models has generated a high level of excitement for this target and small molecule compounds that can modulate the STING pathway have potential to treat chronic viral infections, such as hepatitis B.

Chronic hepatitis B virus (HBV) infection is a significant global health problem, affecting over 5% of the world population (over 350 million people worldwide and 1.25 million individuals in the U.S.). Despite the availability of certain HBV vaccines and therapies, the burden of chronic HBV infection continues to be a significant unmet worldwide medical problem due to suboptimal treatment options and sustained rates of new infections in most parts of the developing world. Current treatments are limited to only two classes of agents: interferon alpha and nucleoside analogues acting as inhibitors of the viral polymerase. Yet none of these therapies offer a cure to the disease, and drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma. There is, therefore, a need in the art for therapeutic agents that can increase the suppression of virus production and that can treat, ameliorate, or prevent HBV infection. Administration of such therapeutic agents to an HBV infected patient, either as monotherapy or in combination with other HBV treatments or ancillary treatments, may lead to significantly reduced virus burden, improved prognosis, diminished progression of the disease and enhanced seroconversion rates.

The potential therapeutic benefits of enhancing both innate and adaptive immunity make STING an attractive therapeutic target that demonstrates impressive activity by itself and can also be combined with other immunotherapies.

SUMMARY OF THE INVENTION

The present invention is directed to compounds of Formula (I)

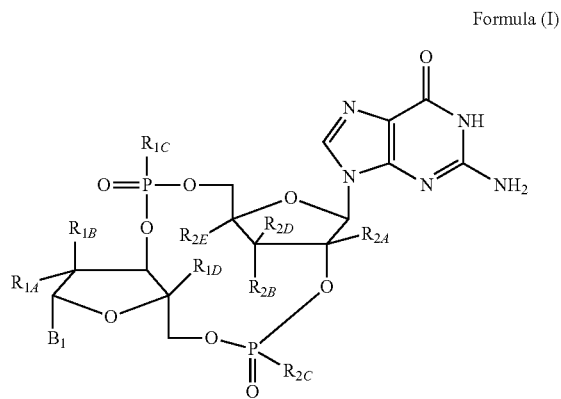

Formula (I)

wherein $R_{1A}$, $R_{2A}$, $R_{1D}$, $R_{2D}$, and $R_{2E}$ are each independently selected from hydrogen or methyl; such that one of said $R_{1A}$, $R_{2A}$, $R_{1D}$, $R_{2D}$, and $R_{2E}$ is methyl;

$R_{1B}$ is hydrogen, hydroxy or fluoro;

or, $R_{1B}$ is —O—, and $R_{1D}$ is $CH_2$, wherein $R_{1B}$, $R_{1D}$ and the atoms to which they are attached form a 5-membered ring;

$R_{1C}$ is selected from the group consisting of hydroxy, thiol, and $BH_3^-$;

$B_1$ is selected from the group consisting of rings b1 and b2

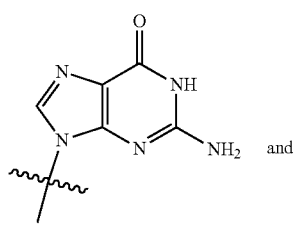

b1 and

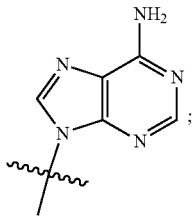

b2

$R_{2B}$ is selected from the group consisting of hydroxy, fluoro and methoxy;

$R_{2C}$ is selected from the group consisting of hydroxy, thiol, and $BH_3^-$;

or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I), or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and/or a pharmaceutically acceptable diluent.

The present invention further provides methods for treating or ameliorating a viral infection, disease, syndrome, or condition in a subject, including a mammal and/or human in which the viral infection, disease, syndrome, or condition is affected by the agonism of STING, using a compound of Formula (I).

The present invention further provides methods for treating or ameliorating a viral infection, disease, syndrome, or condition in a subject, including a mammal and/or human, using a compound of Formula (I).

The present invention further provides methods for treating or ameliorating a viral infection, disease, syndrome, or condition in a subject, including a mammal and/or human in which the viral infection, disease, syndrome, or condition is affected by the agonism of STING, selected from the group consisting of melanoma, colon cancer, breast cancer, prostate cancer, lung cancer, fibrosarcoma, and hepatitis B, using a compound of Formula (I).

The present invention further provides methods for treating or ameliorating a viral infection, disease, syndrome, or condition in a subject, including a mammal and/or human, selected from the group consisting of melanoma, colon cancer, breast cancer, prostate cancer, lung cancer, fibrosarcoma, and hepatitis B, using a compound of Formula (I).

The present invention is also directed to the use of any of the compounds described herein in the preparation of a medicament wherein the medicament is prepared for treating a viral infection, disease, syndrome, or condition that is affected by the agonism of STING, selected from the group consisting of melanoma, colon cancer, breast cancer, prostate cancer, lung cancer, fibrosarcoma, and hepatitis B, in a subject in need thereof.

The present invention is also directed to the use of any of the compounds described herein in the preparation of a medicament wherein the medicament is prepared for treating a viral infection, disease, syndrome, or condition selected from the group consisting of melanoma, colon cancer, breast cancer, prostate cancer, lung cancer, fibrosarcoma, and hepatitis B, in a subject in need thereof.

The present invention is also directed to the preparation of substituted cyclic dinucleotide derivatives that act as selective agonists of STING.

Exemplifying the invention are methods of treating a viral infection, disease, syndrome, or condition modulated by STING selected from the group consisting of melanoma, colon cancer, breast cancer, prostate cancer, lung cancer, fibrosarcoma, and hepatitis B, comprising administering to a subject in need thereof a therapeutically effective amount of any of the compounds or pharmaceutical compositions described above.

Exemplifying the invention are methods of treating a viral infection, disease, syndrome, or condition selected from the group consisting of melanoma, colon cancer, breast cancer, prostate cancer, lung cancer, fibrosarcoma, and hepatitis B, comprising administering to a subject in need thereof a therapeutically effective amount of any of the compounds or pharmaceutical compositions described above.

In another embodiment, the present invention is directed to a compound of Formula (I) for use in the treatment of a viral infection, disease, syndrome, or condition affected by the agonism of STING selected from the group consisting of melanoma, colon cancer, breast cancer, prostate cancer, lung cancer, fibrosarcoma, and hepatitis B.

In another embodiment, the present invention is directed to a composition comprising a compound of Formula (I) for the treatment of a viral infection, disease, syndrome, or condition selected from the group consisting of melanoma, colon cancer, breast cancer, prostate cancer, lung cancer, fibrosarcoma, and hepatitis B.

The present invention is also directed to compounds of Formula (II)

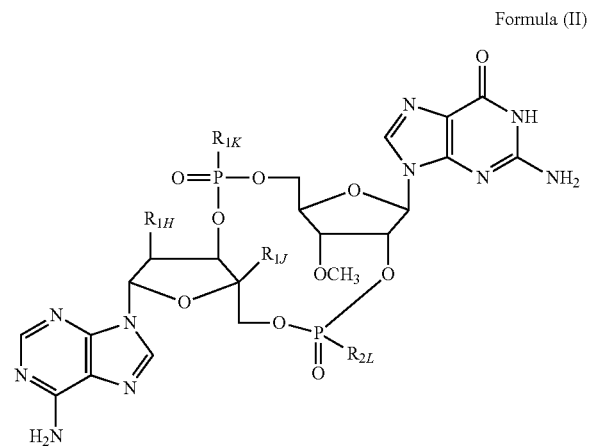

Formula (II)

wherein $R_{1H}$ is fluoro; or, $R_{1H}$ is —O—, and $R_{1J}$ is $CH_2$, wherein $R_{1H}$, $R_{1J}$ and the atoms to which they are attached form a 5-membered ring;

$R_{1J}$ is hydrogen or methyl;

$R_{1K}$ is selected from the group consisting of hydroxy or thiol;

$R_{2L}$ is selected from the group consisting of hydroxy and thiol;

or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (II), or a pharmaceutically acceptable salt form thereof.

Also provided are processes for making a pharmaceutical composition comprising, consisting of, and/or consisting essentially of admixing a compound of Formula (II), and a pharmaceutically acceptable carrier, a pharmaceutically acceptable excipient, and/or a pharmaceutically acceptable diluent.

The present invention further provides methods for treating or ameliorating a viral infection, disease, syndrome, or condition in a subject, including a mammal and/or human in which the viral infection, disease, syndrome, or condition is affected by the agonism of STING, using a compound of Formula (II).

The present invention further provides methods for treating or ameliorating a viral infection, disease, syndrome, or condition in a subject, including a mammal and/or human, using a compound of Formula (II).

The present invention further provides methods for treating or ameliorating a viral infection, disease, syndrome, or condition in a subject, including a mammal and/or human in which the viral infection, disease, syndrome, or condition is affected by the agonism of STING, selected from the group consisting of melanoma, colon cancer, breast cancer, prostate cancer, lung cancer, fibrosarcoma, and hepatitis B, using a compound of Formula (II).

The present invention further provides methods for treating or ameliorating a viral infection, disease, syndrome, or condition in a subject, including a mammal and/or human, selected from the group consisting of melanoma, colon cancer, breast cancer, prostate cancer, lung cancer, fibrosarcoma, and hepatitis B, using a compound of Formula (II).

The present invention is also directed to the preparation of substituted cyclic dinucleotide derivatives of Formula (II) that act as selective agonists of STING.

Exemplifying the invention are methods of treating a viral infection, disease, syndrome, or condition modulated by STING selected from the group consisting of melanoma, colon cancer, breast cancer, prostate cancer, lung cancer, fibrosarcoma, and hepatitis B, comprising administering to a subject in need thereof a therapeutically effective amount of any of the compounds of Formula (II), or a pharmaceutical composition thereof.

Exemplifying the invention are methods of treating a viral infection, disease, syndrome, or condition selected from the group consisting of melanoma, colon cancer, breast cancer, prostate cancer, lung cancer, fibrosarcoma, and hepatitis B, comprising administering to a subject in need thereof a therapeutically effective amount of a compound of Formula (II), or a pharmaceutical composition thereof.

In another embodiment, the present invention is directed to a compound of Formula (II) for use in the treatment of a viral infection, disease, syndrome, or condition affected by the agonism of STING selected from the group consisting of melanoma, colon cancer, breast cancer, prostate cancer, lung cancer, fibrosarcoma, and hepatitis B.

In another embodiment, the present invention is directed to a composition comprising a compound of Formula (II) for the treatment of a viral infection, disease, syndrome, or condition selected from the group consisting of melanoma, colon cancer, breast cancer, prostate cancer, lung cancer, fibrosarcoma, and hepatitis B.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}alkyl)_2$ amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl. The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

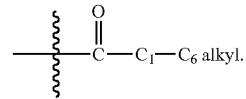

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "STING agonist" is intended to encompass a compound that interacts with STING by binding to it and inducing downstream signal transduction characterized by activation of the molecules associated with STING function. This includes direct phosphorylation of STING, IRF3 and/or NF-κB and could also include STAT6. STING pathway activation results in increased production of type I interferons (mainly IFN-α and IFN-β) and expression of interferon-stimulated genes (Chen H, et al. "Activation of STAT6 by STING Is Critical for Antiviral Innate Immunity". *Cell.* 2011, vol. 14: 433-446; and Liu S-Y, et al. "Systematic identification of type I and type II interferon-induced antiviral factors". *Proc. Natl. Acad. Sci.* 2012:vol. 109 4239-4244).

The term "STING-modulated" is used to refer to a condition affected by STING directly or via the STING pathway, including but not limited to, viral infections, diseases or conditions such as melanoma, colon cancer, breast cancer, prostate cancer, lung cancer, fibrosarcoma, and hepatitis B infection.

As used herein, unless otherwise noted, the term "disorder modulated by STING" shall mean any viral infection, disease, disorder or condition characterized in that at least one of its characteristic symptoms is alleviated or eliminated upon treatment with a STING agonist. Suitable examples include, but are not limited to melanoma, colon cancer, breast cancer, prostate cancer, lung cancer, fibrosarcoma, and hepatitis B.

As used herein, unless otherwise noted, the term "affect" or "affected" (when referring to a viral infection, disease, syndrome, condition or disorder that is affected by agonism of STING) includes a reduction in the frequency and/or severity of one or more symptoms or manifestations of said viral infection, disease, syndrome, condition or disorder; and/or include the prevention of the development of one or more symptoms or manifestations of said viral infection, disease, syndrome, condition or disorder or the development of the viral infection, disease, condition, syndrome or disorder.

The compounds of the instant invention are useful in methods for treating or ameliorating a viral infection, disease, a syndrome, a condition or a disorder that is affected by the agonism of STING. Such methods comprise, consist of and/or consist essentially of administering to a subject, including an animal, a mammal, and a human in need of such treatment, amelioration and/or prevention, a therapeutically effective amount of a compound of Formula (I) or Formula (II), or an enantiomer, diastereomer, solvate or pharmaceutically acceptable salt thereof.

In particular, the compounds of Formula (I) and Formula (II), or an enantiomer, diastereomer, solvate or pharmaceutically acceptable salt form thereof are useful for treating or ameliorating diseases, syndromes, conditions, or disorders such as melanoma, colon cancer, breast cancer, prostate cancer, lung cancer, fibrosarcoma, and hepatitis B.

More particularly, the compounds of Formula (I) and Formula (II), or an enantiomer, diastereomer, solvate or pharmaceutically acceptable salt form thereof are useful for treating or ameliorating melanoma, colon cancer, breast cancer, prostate cancer, lung cancer, fibrosarcoma, and hepatitis B, comprising administering to a subject in need thereof a therapeutically effective amount of a compound of Formula (I) or Formula (II), or an enantiomer, diastereomer, solvate or pharmaceutically acceptable salt form thereof as herein defined.

Some embodiments disclosed herein relate to methods of ameliorating and/or treating a viral infection including infections caused by Hepadnaviridae such as hepatitis B virus or HBV. The methods can include administering to a subject identified as suffering from a viral infection an effective amount of one or more compounds of Formula (I) or Formula (II), or a pharmaceutically acceptable salt form thereof, or a pharmaceutical composition that includes one or more compounds of Formula (I) or Formula (II), or a pharmaceutically acceptable salt form thereof.

Other embodiments disclosed herein relate to a method of ameliorating and/or treating a viral infection that can include contacting a cell infected with the virus with an effective amount of one or more compounds described herein (for example, a compound of Formula (I) or Formula (II), or a pharmaceutically acceptable salt form thereof), or a pharmaceutical composition that includes one or more compounds described herein, or a pharmaceutically acceptable salt thereof. Still other embodiments described herein relate to using one or more compounds of Formula (I) or Formula (II), or a pharmaceutically acceptable salt form thereof, in the manufacture of a medicament for ameliorating and/or treating a viral infection.

Yet still other embodiments described herein relate to one or more compounds of Formula (I) or Formula (II), or a pharmaceutically acceptable salt form thereof, or a pharmaceutical composition that includes one or more compounds of Formula (I) or Formula (II), or a pharmaceutically acceptable salt form thereof, that can be used for ameliorating and/or treating a viral infection. Some embodiments disclosed herein relate to a method of inhibiting replication of a virus that can include contacting a cell infected with the virus with an effective amount of one or more compounds of Formula (I) or Formula (II), or a pharmaceutically acceptable salt form thereof, or a pharmaceutical composition that includes one or more compounds described herein, or a pharmaceutically acceptable salt form thereof.

Other embodiments described herein relate to using one or more compounds of Formula (I) or Formula (II), or a pharmaceutically acceptable salt form thereof) in the manufacture of a medicament for inhibiting replication of a virus. Still other embodiments described herein relate to one or more compounds described herein (for example, a compound of Formula (I) or Formula (II), or a pharmaceutically acceptable salt form thereof), or a pharmaceutical composition that includes one or more compounds described herein, or a pharmaceutically acceptable salt form thereof, that can be used for inhibiting replication of a virus.

In some embodiments, the viral infection can be a hepatitis B viral infection. The methods can include administering to a subject identified as suffering from HBV an effective amount of one or more compounds of Formula (I) or Formula (II), or a pharmaceutically acceptable salt form thereof, or a pharmaceutical composition that includes one or more compounds of Formula (I) or Formula (II), or a pharmaceutically acceptable salt form thereof.

Other embodiments disclosed herein relate to a method of ameliorating and/or treating a viral infection that can include contacting a cell infected with HBV with an effective amount of one or more compounds of Formula (I) or Formula (II), or a pharmaceutically acceptable salt form thereof, or a pharmaceutical composition that includes one or more compounds of Formula (I) or Formula (II), or a pharmaceutically acceptable salt form thereof. Still other embodiments described herein relate to using one or more compounds of Formula (I) or Formula (II), or a pharmaceutically acceptable salt form thereof, in the manufacture of a medicament for ameliorating and/or treating HBV.

Yet still other embodiments described herein relate to one or more compounds of Formula (I) or Formula (II), or a pharmaceutically acceptable salt form thereof, or a pharmaceutical composition that includes one or more compounds of Formula (I) or Formula (II), or a pharmaceutically acceptable salt form thereof, that can be used for ameliorating and/or treating HBV. Some embodiments disclosed herein relate to a method of inhibiting replication of HBV that can include contacting a cell infected with the virus with an effective amount of one or more compounds of Formula (I) or Formula (II), or a pharmaceutically acceptable salt form thereof, or a pharmaceutical composition that includes one or more compounds of Formula (I) or Formula (II), or a pharmaceutically acceptable salt form thereof.

Other embodiments described herein relate to using one or more compounds of Formula (I) or Formula (II), or a pharmaceutically acceptable salt thereof) in the manufacture of a medicament for inhibiting replication of HBV. Still other embodiments described herein relate to one or more compounds of Formula (I) or Formula (II), or a pharmaceutically acceptable salt thereof, or a pharmaceutical composition that includes one or more compounds of Formula (I) or Formula (II), or a pharmaceutically acceptable salt form thereof, that can be used for inhibiting replication of HBV.

An embodiment of the present invention is directed to compounds of Formula (I)

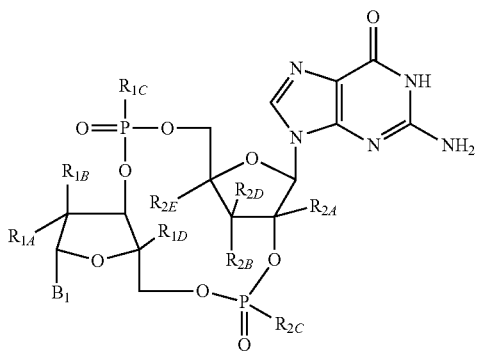

Formula (I)

wherein

AA) $R_{1B}$ is hydroxy or fluoro; and $R_{1D}$ is hydrogen;
BB) $R_{1B}$ is —O—, and $R_{1D}$ is CH$_2$, wherein $R_{1B}$, $R_{1D}$ and the atoms to which they are attached form a 5-membered ring;
CC) $R_{1C}$ is selected from the group consisting of hydroxy and thiol;
DD) B$_1$ is ring b2

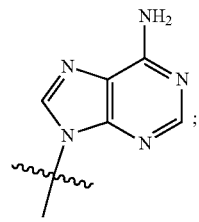

b2

EE) $R_{2C}$ is selected from the group consisting of hydroxy and thiol;

and any combination of embodiments AA) though EE) above, such that one of said $R_{1A}$, $R_{2A}$, $R_{1D}$, $R_{2D}$, and $R_{2E}$ is methyl; and provided that it is understood that combinations in which different embodiments of the same substituent would be combined are excluded; or an enantiomer, diastereomer, or pharmaceutically acceptable salt form thereof.

One embodiment of the present invention is directed to a compound of Formula (I)

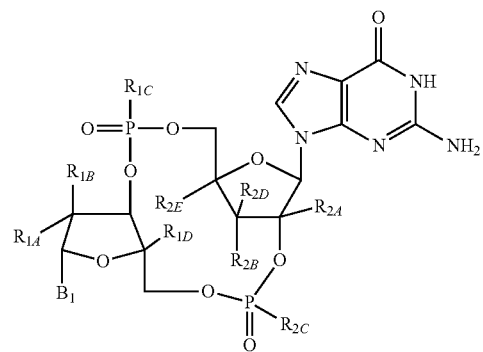

Formula (I)

wherein $R_{1A}$, $R_{2A}$, $R_{1D}$, $R_{2D}$, and $R_{2E}$ are each independently selected from hydrogen or methyl; such that one of said $R_{1A}$, $R_{2A}$, $R_{1D}$, $R_{2D}$, and $R_{2E}$ is methyl;

$R_{1B}$ is hydrogen, hydroxy or fluoro;

or, $R_{1B}$ is —O—, and $R_{1D}$ is CH$_2$, wherein $R_{1B}$, $R_{1D}$ and the atoms to which they are attached form a 5-membered ring;

$R_{1C}$ is selected from the group consisting of hydroxy and thiol;

B$_1$ is ring b2

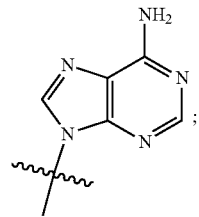

b2

$R_{2B}$ is selected from the group consisting of hydroxy, fluoro and methoxy;

$R_{2C}$ is selected from the group consisting of hydroxy and thiol;

or an enantiomer, diastereomer, or pharmaceutically acceptable salt form thereof.

Embodiments of the present invention include a compound of Formula (I) as herein defined, or an enantiomer, diastereomer, solvate, or a pharmaceutically acceptable salt form thereof, wherein the substituents selected from one or more of the variables defined herein (e.g. $R_{1A}$, $R_{1B}$, $R_{1C}$, $R_{1D}$, $B_1$, $R_{2A}$, $R_{2B}$, $R_{2C}$, $R_{2D}$, and $R_{2E}$) are independently selected to be any individual substituent or any subset of substituents from those exemplified in the listing in Table 1, below.

TABLE 1

Formula (I)

| Cpd No. | $R_{1A}$ | $R_{1B}$ | $R_{1C}$ | $R_{1D}$ | $B_1$ | $R_{2B}$ | $R_{2D}$ | $R_{2C}$ |
|---|---|---|---|---|---|---|---|---|
| 1 | $CH_3$ | OH | $OH^-$ | H | b2 | OH | H | OH |
| 2 | H | OH | $OH^-$ | $CH_3$ | b2 | OH | H | OH |
| 3 | H | OH | OH | H | b2 | OH | $CH_3$ | OH |

A further embodiment of the present invention is directed to a compound of Formula (I), selected from compounds 1 to 3,

1

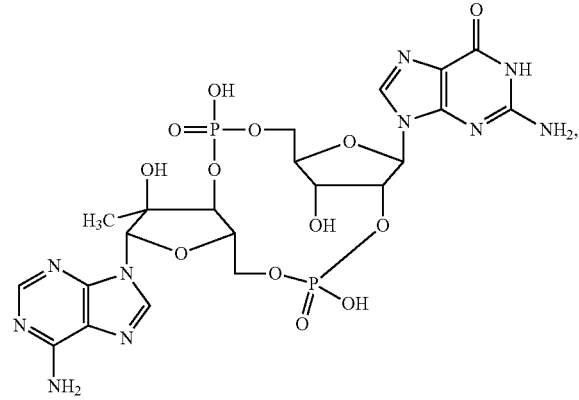

2

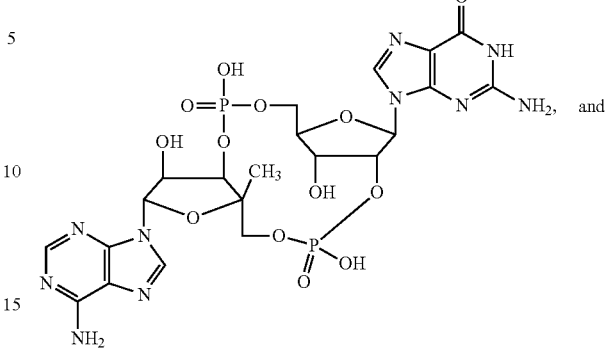

and

3

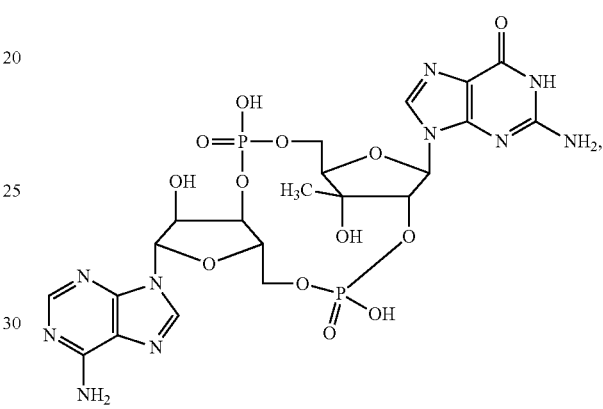

or a pharmaceutically acceptable salt form thereof.

Embodiments of the present invention include a compound of Formula (II) as herein defined, or an enantiomer, diastereomer, solvate, or a pharmaceutically acceptable salt form thereof, wherein the substituents selected from one or more of the variables defined herein (e.g. $R_{1H}$, $R_{1K}$, $R_{1J}$, and $R_{2L}$) are independently selected to be any individual substituent or any subset of substituents from those exemplified in the listing in Table 2, below.

TABLE 2

Formula (II)

| Cpd No. | $R_{1H}$ | $R_{1K}$ | $R_{1J}$ | $R_{2L}$ |
|---|---|---|---|---|
| 4 | —O— | OH | $CH_2$ to form a ring with $R_{1H}$ | OH |

TABLE 2-continued

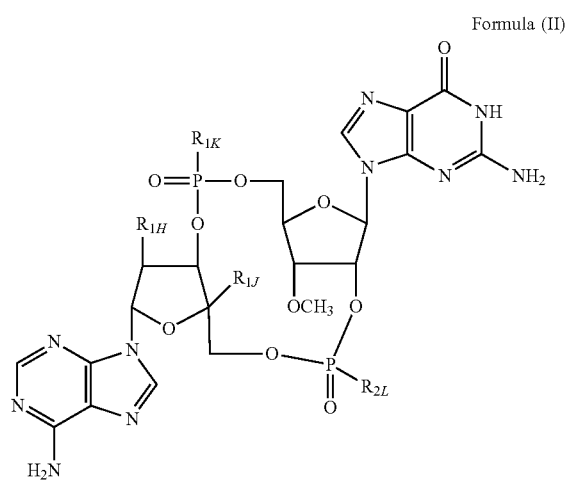

| Cpd No. | $R_{1H}$ | $R_{1K}$ | $R_{1J}$ | $R_{2L}$ |
|---|---|---|---|---|
| 5 | F | OH | H | OH |
| 6a | F | (*R)—SH | H | (*S)—SH |
| 6b | F | (*S)—SH | H | (*R)—SH |
| 6c | F | (*S)—SH | H | (*S)—SH |
| 6d | F | (*R)—SH | H | (*R)—SH |

A further embodiment of the present invention is directed to compounds 4 to 6 of Formula (II)

4

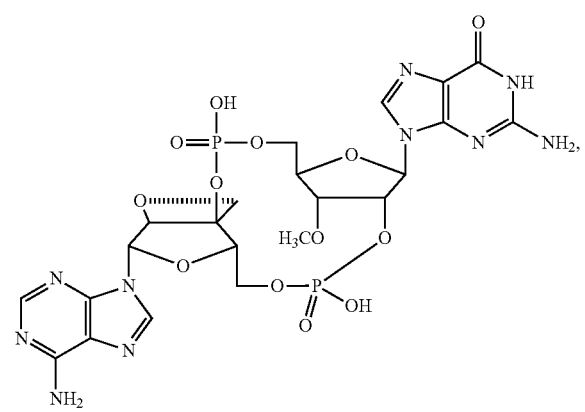

5

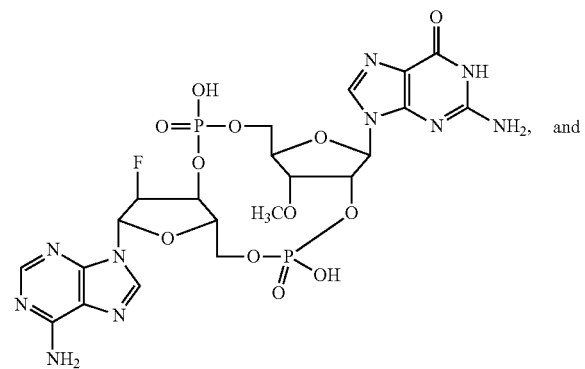

and

6

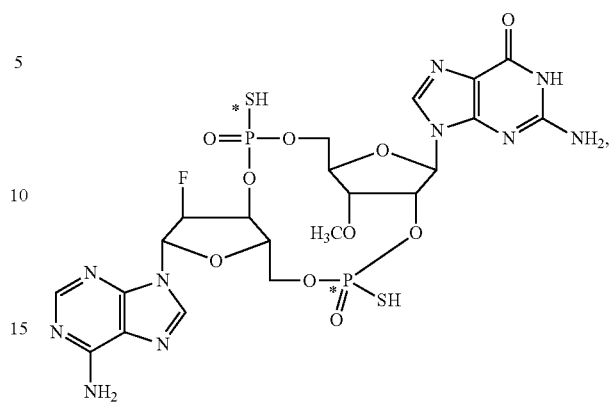

or a pharmaceutically acceptable salt form thereof.

For use in medicine, salts of compounds of Formula (I) and Formula (II) refer to non-toxic "pharmaceutically acceptable salts." Other salts may, however, be useful in the preparation of compounds of Formula (I) and Formula (II) or of their pharmaceutically acceptable salt forms thereof. Suitable pharmaceutically acceptable salts of compounds of Formula (I) and Formula (II) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) and Formula (II) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, c-oxo-glutaric acid, glycolic acid, hippuric acid, hydrobromic acid, hydrochloric acid, (+)-L-lactic acid, (+)-DL-lactic acid, lactobionic acid, maleic acid, (−)-L-malic acid, malonic acid, (+)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I) and Formula (II). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I) and Formula (II).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) or Formula (II) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\% \ (+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) or Formula (II) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\% \ (-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis*, Third Edition, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and/or Formula (II) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) and Formula (II) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) and Formula (II) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

In addition to the above described routes of administration for the treatment of cancer, the pharmaceutical compositions may be adapted for administration by intratumoral or peritumoral injection. The activation of the immune system in this manner to kill tumors at a remote site is commonly known as the abscopal effect and has been demonstrated in animals with multiple therapueutic modalities, (van der Jeught, et al., *Oncotarget,* 2015, 6(3), 1359-1381). A further advantage of local or intratumoral or peritumoral administration is the ability to achieve equivalent efficacy at much lower doses, thus minimizing or eliminating adverse events that may be observed at much higher doses (Marabelle, A., et al., *Clinical Cancer Research,* 2014, 20(7), 1747-1756).

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) and Formula (II) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or Formula (II) or a pharmaceutical composition thereof includes a dose range from about 0.01 mg to about 3000 mg, or any particular amount or range therein, in particular from about 0.05 mg to about 1000 mg, or any particular amount or range therein, or, more particularly, from about 0.05 mg to about 250 mg, or any particular amount or range therein, of active ingredient in a regimen of about 1 to about 4 times per day for an average (70 kg) human; although, it is apparent to one skilled in the art that the therapeutically effective amount for a compound of Formula (I) or Formula (II) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I) or Formula (II).

Advantageously, a compound of Formula (I) or Formula (II) may be administered in a single daily dose, or the total daily dosage may be administered in divided doses of two, three and four times daily.

Optimal dosages of a compound of Formula (I) or Formula (II) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) and Formula (II) may be administered in any of the foregoing compositions and dosage regimens or by means of those compositions and dosage regimens established in the art whenever use of a compound of Formula (I) or Formula (II) is required for a subject in need thereof.

As STING protein agonists, the compounds of Formula (I) and Formula (II) are useful in methods for treating or preventing a viral infection, disease, a syndrome, a condition or a disorder in a subject, including an animal, a mammal and a human in which the viral infection, disease, the syndrome, the condition or the disorder is affected by the modulation, including agonism, of the STING protein. Such methods comprise, consist of and/or consist essentially of administering to a subject, including an animal, a mammal, and a human, in need of such treatment or prevention, a therapeutically effective amount of a compound, salt or solvate of Formula (I) or Formula (II).

In one embodiment, the present invention is directed to a compound of Formula (I) or Formula (II), or a pharmaceutically acceptable salt form thereof, for the use in the treatment of cancer, and cancer diseases and conditions, or a viral infection.

Examples of cancer diseases and conditions for which compounds of Formula (I) or Formula (II), or pharmaceutically acceptable salts or solvates thereof, may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease or a combination of one or more of the foregoing cancers. Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal madenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, pro myelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In another embodiment, the present invention is directed to a compound of Formula (I) or Formula (II), or a pharmaceutically acceptable salt form thereof, for use in the treatment of a disorder affected by the agonism of STING selected from the group consisting of melanoma, colon cancer, breast cancer, prostate cancer, lung cancer, fibrosarcoma, and hepatitis B.

The disclosed compounds of Formula (I) or Formula (II) may be useful in combination with one or more additional compounds useful for treating HBV infection. These additional compounds may comprise other disclosed compounds and/or compounds known to treat, prevent, or reduce the symptoms or effects of HBV infection. Such compounds include, but are not limited to, HBV polymerase inhibitors, interferons, viral entry inhibitors, viral maturation inhibitors, literature-described capsid assembly modulators, reverse transcriptase inhibitors, immunomodulatory agents, TLR-agonists, and other agents with distinct or unknown mechanisms that affect the HBV life cycle or that affect the consequences of HBV infection.

In non-limiting examples, the disclosed compounds may be used in combination with one or more drugs (or a salt thereof) selected from the group comprising:

HBV reverse transcriptase inhibitors, and DNA and RNA polymerase inhibitors including, but not limited to, lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons including, but not limited to, interferon alpha (IFN-α), interferon beta (IFN-β), interferon lambda (IFN-λ), and interferon gamma (IFN-γ);

viral entry inhibitors;

viral maturation inhibitors;

capsid assembly modulators, such as, but not limited to, BAY 41-4109;

reverse transcriptase inhibitors;

immunomodulatory agents such as TLR-agonists; and agents of distinct or unknown mechanisms, such as, but not limited to, AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl) prop-1-en-2-yl)-4-nitrobenzamide), and analogs thereof.

In one embodiment, the additional therapeutic agent is an interferon. The term "interferon" or "IFN" refers to any member of the family of highly homologous species-specific proteins that inhibit viral replication and cellular proliferation and modulate immune response. For example, human interferons are grouped into three classes: Type I, which includes interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons may include pegylated interferons and glycosylated interferons. Examples of interferons also include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferon alpha-2b.

Accordingly, in one embodiment, the compounds of Formula (I) and Formula (II) can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS). In another embodiment, the additional therapeutic agent is selected from immune modulator or immune stimulator therapies, which includes biological agents belonging to the interferon class.

Further, the additional therapeutic agent may be an agent that disrupts the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor or DNA or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can effect maturation of antigen presenting cells, proliferation of T-cells and cytokine release (e.g., IL-12, IL-18, IFN-alpha, -beta, and -gamma and TNF-alpha among others), In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms.

In another aspect, provided herein is method of treating an HBV infection in an individual in need thereof, comprising reducing the HBV viral load by administering to the individual a therapeutically effective amount of a disclosed compound alone or in combination with a reverse transcriptase inhibitor; and further administering to the individual a therapeutically effective amount of HBV vaccine. The reverse transcriptase inhibitor may be at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another aspect, provided herein is a method of treating an HBV infection in an individual in need thereof, comprising reducing the HBV viral load by administering to the individual a therapeutically effective amount of a disclosed compound alone or in combination with an antisense oligonucleotide or RNA interference agent that targets HBV nucleic acids; and further administering to the individual a therapeutically effective amount of HBV vaccine. The antisense oligonucleotide or RNA interference agent possesses sufficient complementarity to the target HBV nucleic acids to inhibit replication of the viral genome, transcription of viral RNAs, or translation of viral proteins.

In another embodiment, the disclosed compound and the at least one additional therapeutic agent are co-formulated. In yet another embodiment, the disclosed compound and the at least one additional therapeutic agent are co-administered. For any combination therapy described herein, synergistic effect may be calculated, for example, using suitable methods such as the Sigmoid-Emax equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In an embodiment of any of the methods of administering combination therapies provided herein, the method can further comprise monitoring or detecting the HBV viral load of the subject, wherein the method is carried out for a period of time including until such time that the HBV virus is undetectable.

Abbreviations used in the instant specification, particularly the schemes and examples, are as follows:
ACN acetonitrile
AcOH glacial acetic acid
ADDP azodicarlboxylic dipiperidide
aq. aqueous
Bn or Bzl benzyl
BINAP 2,2'-bis(diphenylphosphino)-1,1'-binaphthyl
Boc tert-butyloxycarbonyl
conc. concentrated
dba dibenzylideneacetone
DBU 1,8-diazabicyclo[5.4.0]undec-7-ene
DCC N,N'-dicyclohexyl-carbodiimide
DCE 1,2-dichloroethane
DCM dichloromethane
DEAD diethyl azodicarboxylate
DIBAL diisobutylaluminum hydride
DIPEA or DIEA diisopropyl-ethyl amine
DMA dimethylaniline
DMAP 4-dimethylaminopyridine
DME dimethoxyethane
DMF N,N-dimethylformamide
DMSO dimethylsulfoxide
DMT 4,4'-dimethoxytrityl
DPPA diphenylphosphoryl azide
dppf 1,1'-bis(diphenylphosphino)ferrocene
EA ethyl acetate
EDCI 1-ethyl-3-(3-dimethylaminopropyl) carbodiimide
ESI electrospray ionization
EtOAc or EA ethyl acetate
EtOH ethanol
GCMS gas chromatography-mass spectrometry
h or hr(s) hour or hours
HEK hum an embryonic kidney
HPLC high performance liquid chromatography
LAH lithium aluminum hydride
LDA lithium diisopropylamide
LHMDS lithium bis(trimethylsilyl)amide
MEK methyl ethyl ketone
MeOH methanol
MHz megahertz
min minute or minutes
MS mass spectrometry
Ms methanesulfonyl
NBS N-bromosuccinimide
NIS N-iodosuccinimide
NMM N-methylmorpholine
NMP N-methylpyrrolidone
NMR nuclear magnetic resonance
PCC pyridinium chlorochromate PE petrolum ether
RP reverse-phase
rt or RT room temperature
Rt retention time
Sec second or seconds
SEM-Cl 2-(trimethylsilyl)ethoxymethyl chloride
TBAF tetrabutylammonium fluoride
TBDMS t-butyldimethylsilyl
TBP tributyl phosphate
TEA or Et₃N triethylamine TFA trifluoroacetic acid
THF tetrahydrofuran
TIPS triisopropylsilyl
TLC thin layer chromatography
TMS tetramethylsilane
Ts 4-toluenesulfonyl

SPECIFIC EXAMPLES

Example 1

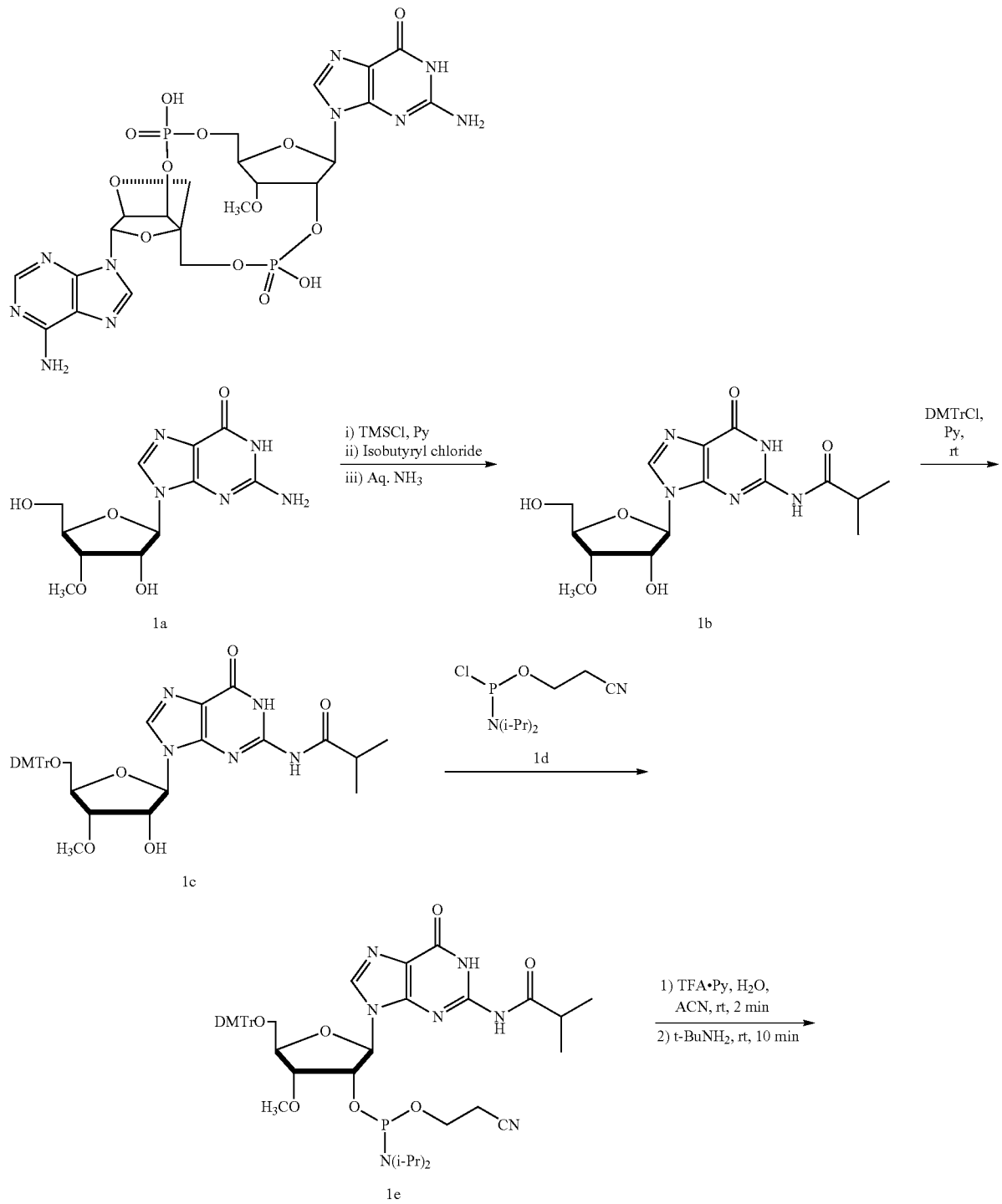

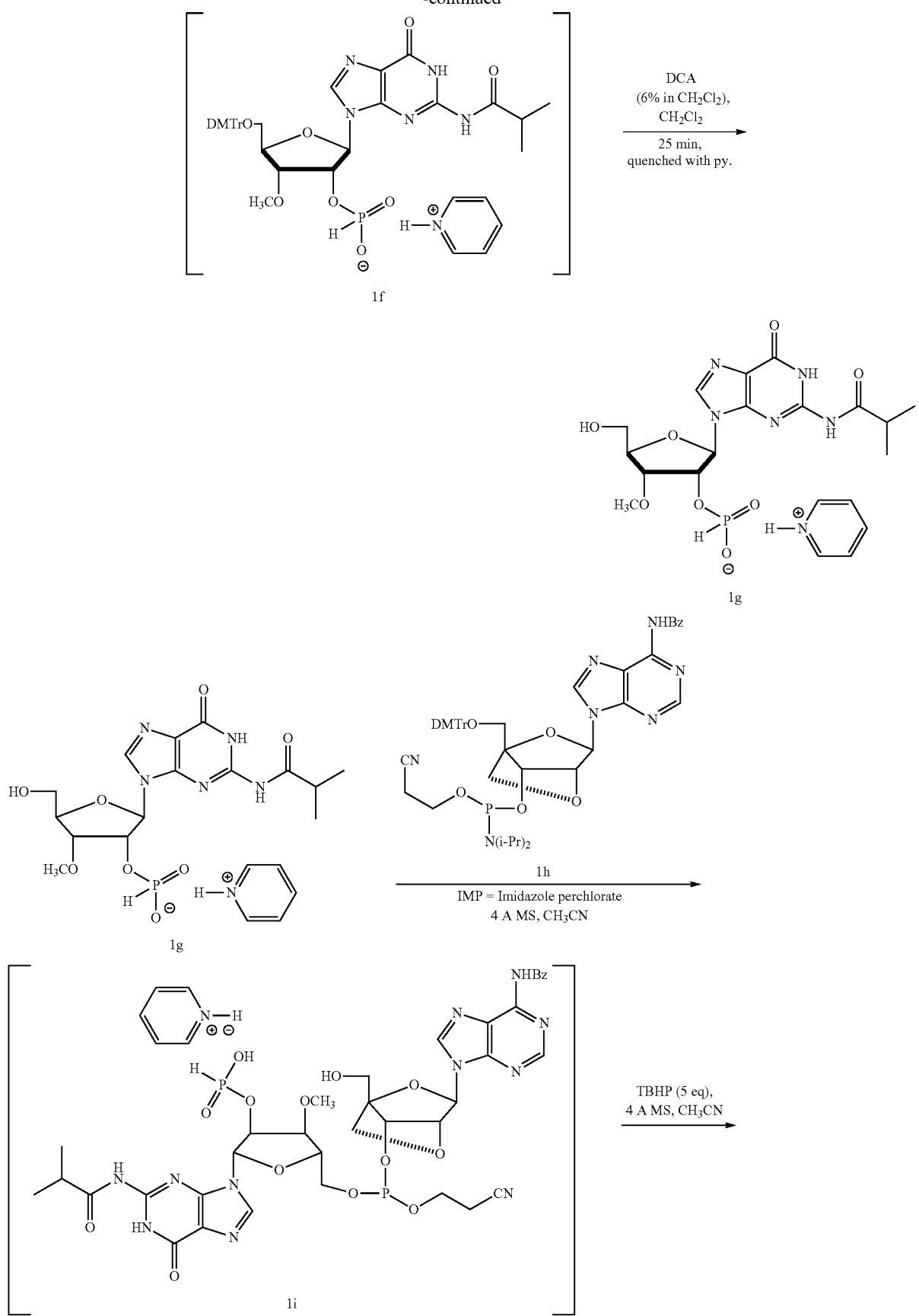

-continued
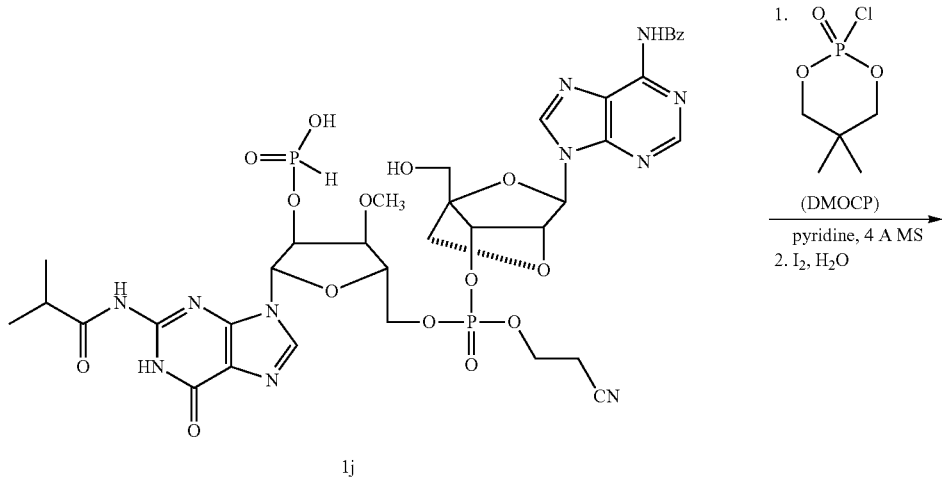
1j
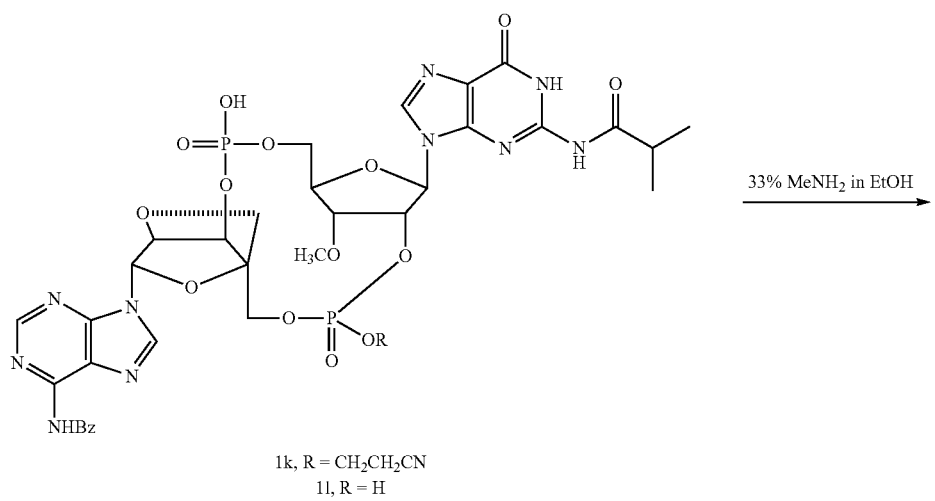
1k, R = CH₂CH₂CN
1l, R = H
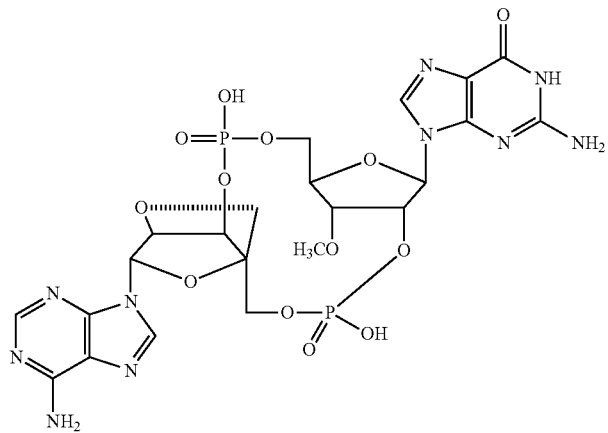
Compound 4, ammonium salt -continued

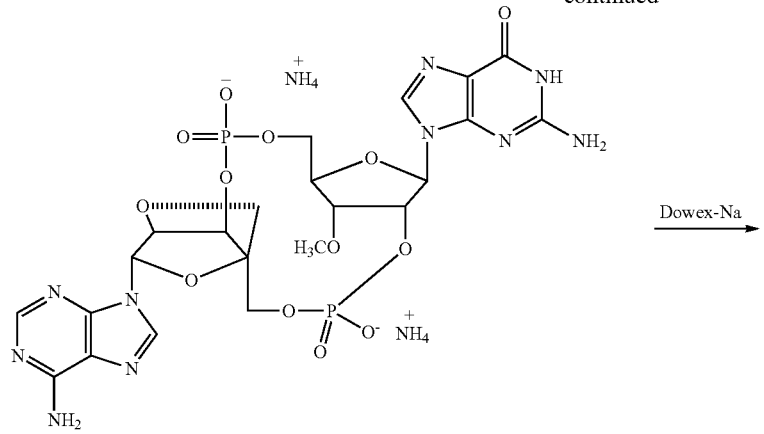

Compound 4, ammonium salt

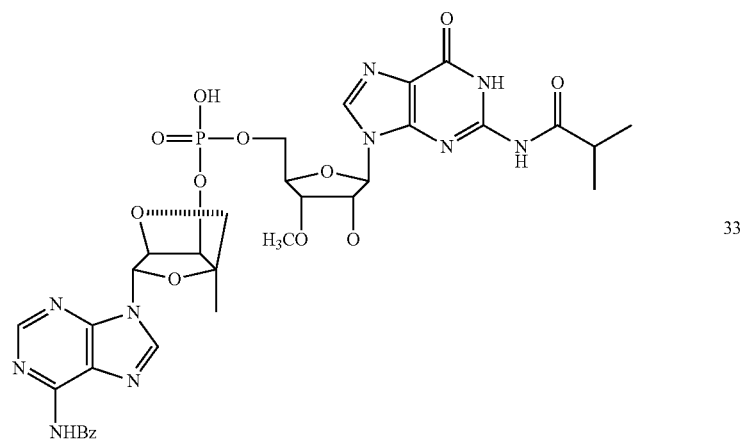

1k, R = CH₂CH₂CN
1l, R = H

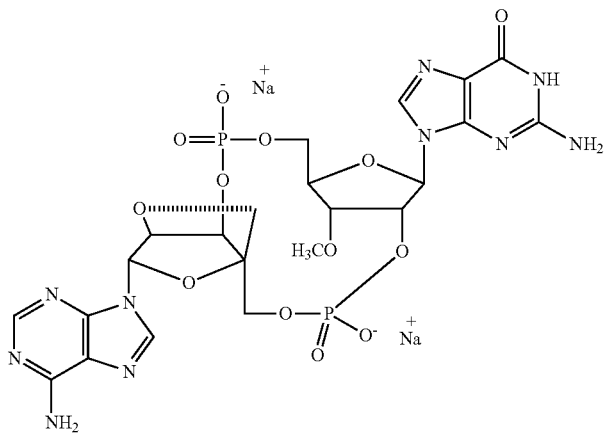

Compound 4 sodium salt

Step 1: Preparation of 1b

To a solution of 1a (5 g, 16.82 mmol) in pyridine (100 mL) was added dropwise tert-butylchlorodimethylsilane (16.4 g, 151.4 mmol) at room temperature. After 1 h, isobutyryl chloride (5.38 g, 50.5 mmol) was added dropwise at room temperature. The final mixture was stirred at room temperature for 2 h. The mixture was quenched with water (150 mL) at 0° C. and NH₄OH (50 mL) was added dropwise at 0° C. After 10 min, the mixture was stirred at room temperature for 0.5 h. The mixture was concentrated. The crude product was purified by flash chromatography (silica gel, $CH_2Cl_2$:MeOH=10:1) to afford 1b (3.8 g, 63.9%). ESI-MS: m/z=368.0 [M+1]$^+$.

Step 2: Preparation of 1c

A solution of 1b (3.7 g, 10.07 mmol) and DMTrCl (5.12 g, 15.11 mmol) in pyridine (10 mL) was stirred at room temperature overnight. The mixture was quenched with water (500 mL) and extracted with $CH_2Cl_2$ (300 mL×3). The combined organic layer was dried over $Na_2SO_4$, filtered, and the filtrate was concentrated. The residue was purified by flash chromatography (silica gel, $CH_2Cl_2$:MeOH=15:1, Rf=0.5) to afford 1c (5.7 g, 84%) as light yellow solid.

Step 3: Preparation of 1e

To a solution of 1c (7.6 g, 11.35 mmol) and DIPEA (8.80 g, 68.09 mmol) in THF (30 mL) was added 3-((chloro (diisopropylamino)phosphino)oxy)propanenitrile 1d (8.06 g, 34.04 mmol) at room temperature. The mixture was stirred at room temperature for 1 h and quenched with MeOH. The mixture was extracted with EtOAc and the combined organic layer was washed with brine twice. The organic layer was dried over $Na_2SO_4$, filtered, and the filtrate concentrated. The residue was purified by flash chromatography ($CH_2Cl_2$:MeOH=20:1, Rf=0.6) to afford compound 1e (9.5 g, 96.23%). ESI-MS: m/z 787.5 [M+1]$^+$.

Step 4: Preparation of 1f

To a solution of 1e (9.5 g, 10.92 mmol) and water (393.464 mg, 21.84 mmol) in dry $CH_3CN$ (38 mL) was added pyridinium trifluoroacetate (2.531 g, 13.10 mmol) at room temperature. t-Butylamine (38 mL) was added. The resulting mixture was stirred at 15° C. for 20 min. The mixture was concentrated to afford 1f (8.876 g, crude) as a white solid. The crude product was used directly for the next step.

Step 5: Preparation of 1g

To a solution of compound 1f (8.876 g, 10.92 mmol) and water (1.967 g, 109.2 mmol) in $CH_2Cl_2$ (80 mL) was added dichloroacetic acid (4.72 g, 36.62 mmol) at room temperature for 1.5 h. Pyridine (1.53 g, 21.84 mmol) was added. The mixture was concentrated and the residue was purified by flash chromatography (silica gel, $CH_2Cl_2$:MeOH=5:1) to afford 1g (3.5 g, 62.79%) as a white solid. $^1$H NMR (400 MHz, DMSO-$d_6$) 8.27 (s, 1H), 7.28-7.22 (m, 5H), 5.92-5.88 (m, 1H), 5.04-4.99 (m, 1H), 3.99-3.96 (m, 2H), 3.78 (m, 2H), 3.43 (s, 3H), 2.87-2.75 (m, 1H), 1.13-1.12 (d, J=6.4 Hz, 6H); $^{31}$P NMR (162 MHz, DMSO-$d_6$) 2.27 (s, 1P), 0.34 (s, 1P); ESI-MS: m/z=431.9 [M+1]$^+$.

Step 6: Preparation of 1j

A solution of 1 g (500 mg, 0.98 mmol) and 4 Å MS (0.5 g) in $CH_3CN$ (35 mL) was stirred at room temperature under an Argon atmosphere for 3 min. Imidazole perchlorate (3.30 g, 19.59 mmol) was added. After 10 min, 1 h (1 g, 1.13 mmol) in $CH_3CN$ (5 mL) was added. The mixture was stirred at 26° C. for 1 h. tert-Butyl hydroperoxide (0.98 mL, 4.90 mmol) was added. The resultant mixture was stirred at 26° C. for 1 h. The mixture was concentrated and the residue was purified by prep-HPLC to afford 1j (38.5 mg, 0.04 mmol, ESI-MS m/z 930.4 (M+1)) and 1j contaminated with DMTr cation (1000 mg, 0.01 mmol, 0.914%, ESI-MS m/z 930.4 (M+1)) as a white solid.

Step 2: Preparation of 1k and 1l

To a solution of 1j (38.5 mg, 0.041 mmol) and molecular sieves in pyridine (20 mL) was added DMOCP (22.93 mg, 0.124 mmol) at room temperature under an Argon atmosphere. The mixture was stirred at 26° C. for 1 h. Water (7.46 mg, 0.414 mmol) and 12 (52.55 mg, 0.207 mmol) were added. The reaction mixture was stirred at 26° C. for 1 h. The reaction was quenched with $Na_2SO_3$ (aq). The mixture was filtered and the filtrate concentrated to give a crude product. The crude product was purified by prep-HPLC to give 2l (7.5 mg, 0.008 mmol, ESI-MS m/z 875.3) and 1k (13.5 mg, 0.015 mmol, ESI-MS m/z 927.9 (M+1)) as a white solid.

Step 3: Preparation of Compound 4, Ammonium Salt

Compound 1l (7.5 mg, 0.008 mmol) was treated with a solution of $MeNH_2$ in EtOH (33%, 3 mL) was stirred at room temperature for 1 h to generate a first crude batch of compound 4.

Compound 1k (13.5 mg, 0.015 mmol) was treated with a solution of $MeNH_2$ in EtOH (5 mL) was stirred at room temperature for 1 h to generate a second crude batch of compound 4. The two crude batches were combined, concentrated to dryness, and purified by prep-HPLC to afford compound 4, ammonium salt (6.8 mg, 0.010 mmol) as a white solid. $^1$H NMR (400 MHz, $D_2O$) 8.14 (s, 1H), 7.92 (s, 1H), 7.69 (s, 1H), 6.03 (s, 1H), 5.77 (d, J=8.4 Hz, 1H), 5.60 (s, 1H), 4.81 (s, 2H), 4.32 (s, 2H), 4.19 (d, J=10.0 Hz, 1H), 4.08-3.99 (m, 4H), 3.89 (d, J=8.8 Hz, 1H), 3.40 (s, 3H); ESI-MS m/z 701.1 (M+1).

Step 4: Preparation of Compound 4, Sodium Salt

An 8 mL volume of Dowex 50W×8, 200-400 (H form) was added to a beaker (for 6.8 mg of compound 4, ammonium salt) and washed with DI $H_2O$ (2×). Then to the resin was added 15% $H_2SO_4$ in deionized water (50 mL), the mixture was stirred for 15 min, and decanted (1×). The resin was transferred to a column with 15% $H_2SO_4$ in DI $H_2O$ and washed with 15% $H_2SO_4$ (at least 4 CV), and then with DI $H_2O$ until it was neutral. The resin was transferred back into the beaker, and 15% NaOH in DI $H_2O$ solution (50 mL) was added, and the mixture was stirred for 15 min, and decanted (1×). The resin was transferred to the column and washed with 15% NaOH in DI $H_2O$ (at least 4 CV), and then with $H_2O$ until it was neutral (at least 4 CV). A was dissolved in DI water (6.8 mg in 5 mL), added to the top of the column, and eluted with DI water. Compound 4 was eluted out in early fractions as detected by TLC (UV). The product was lyophilized to give compound 4, sodium salt (5.6 mg, 0.008 mmol). $^1$H NMR (400 MHz, $D_2O$) 8.14 (s, 1H), 7.89 (s, 1H), 7.76 (s, 1H), 6.04 (s, 1H), 5.84 (d, J=8.4 Hz, 1H), 5.76-5.67 (m, 1H), 4.97 (d, J=2.8 Hz, 1H), 4.84 (s, 1H), 4.47-4.34 (m, 2H), 4.24 (d, J=12.0 Hz, 1H), 4.18 (d, J=4.4 Hz, 1H), 4.09 (d, J=8.0 Hz, 3H), 3.95 (d, J=8.4 Hz, 1H), 3.47 (s, 3H). $^{31}$P NMR (162 MHz, $D_2O$) −1.51, −2.20; ESI-MS m/z 700.8 (M+1).

Example 2
Cpd 5
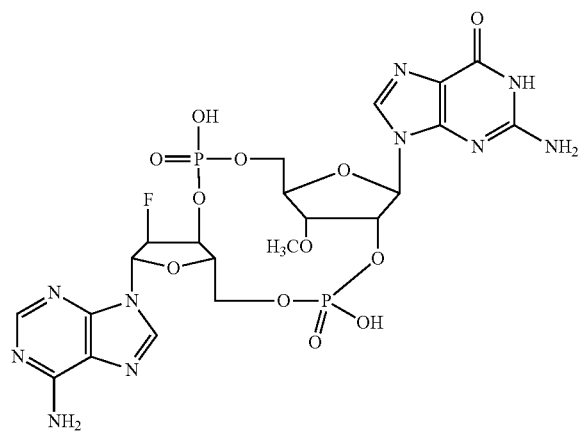
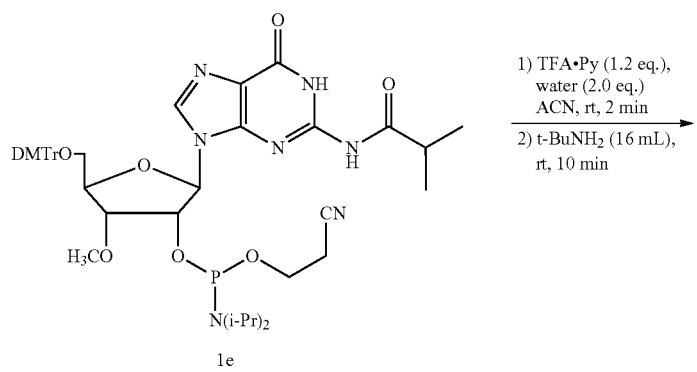
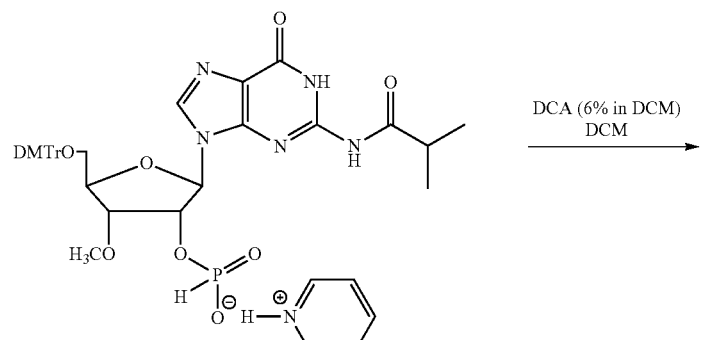

-continued
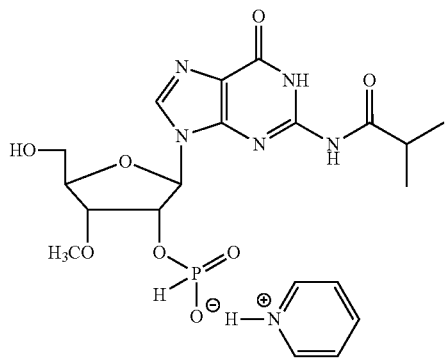
2b
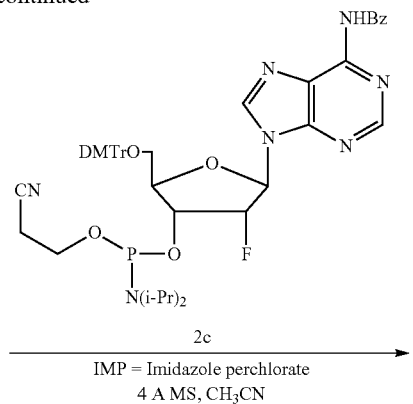
2c
IMP = Imidazole perchlorate
4 A MS, CH₃CN
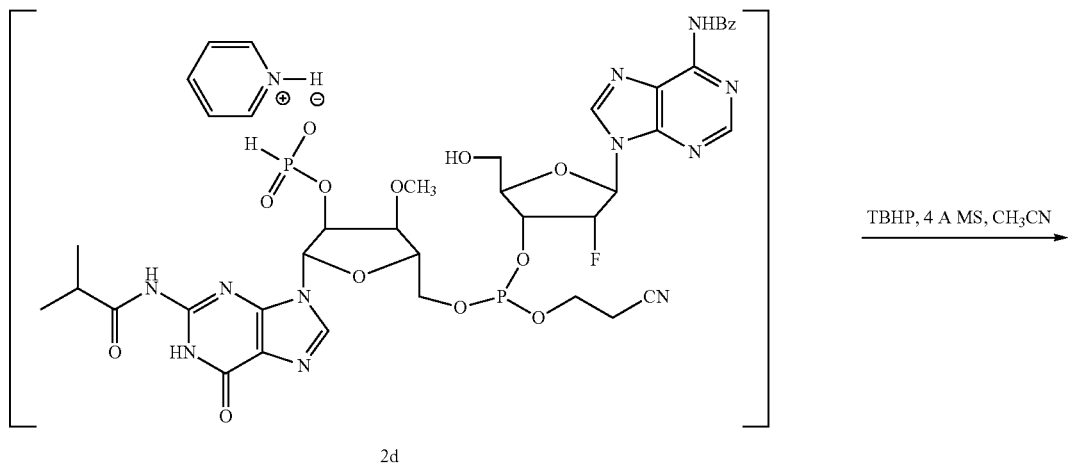
2d
TBHP, 4 A MS, CH₃CN
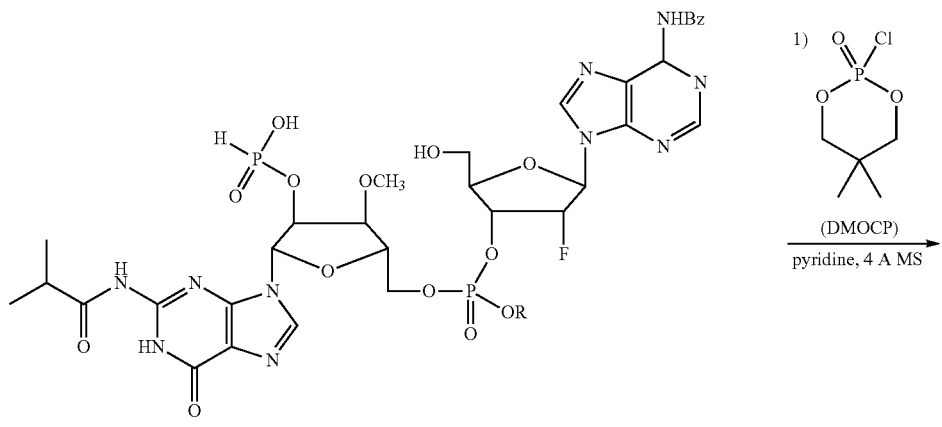 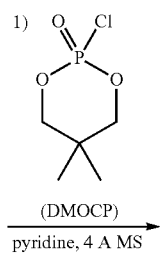
(DMOCP)
pyridine, 4 A MS
2e, R = CH₂CH₂CN
2f, R = H -continued
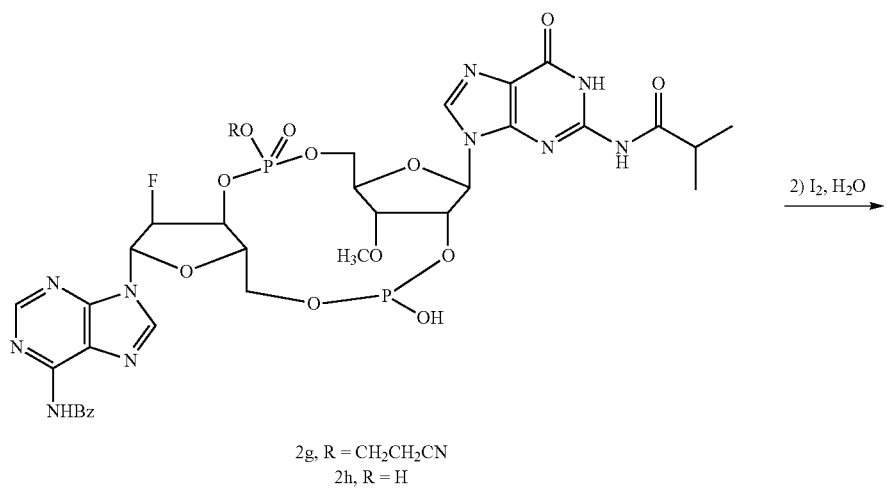
2g, R = CH₂CH₂CN
2h, R = H
2) I₂, H₂O →
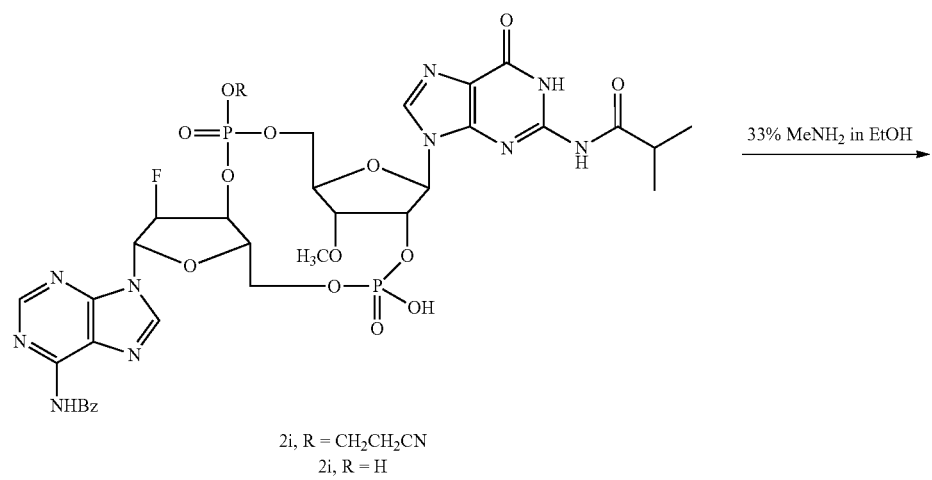
2i, R = CH₂CH₂CN
2j, R = H
33% MeNH₂ in EtOH →
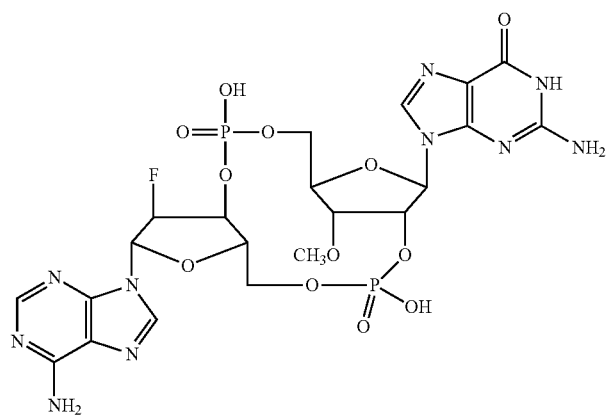
Compound 5, ammonium salt

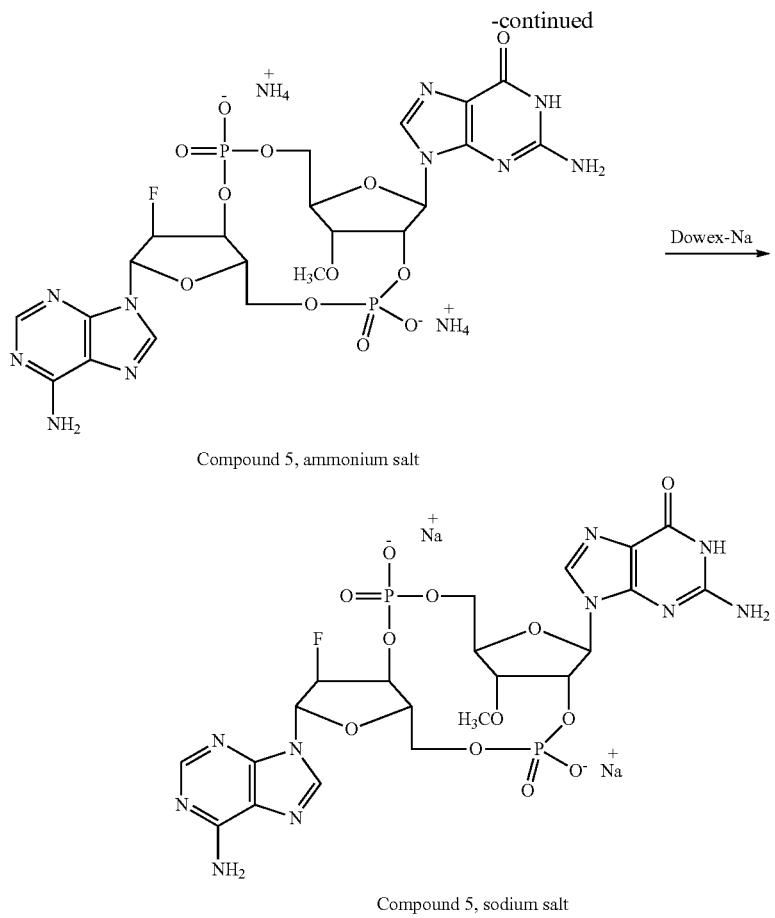

Compound 5, ammonium salt

Compound 5, sodium salt

Step 1: Preparation of Compound 2a

To a solution of compound 1e (1.2 g, 1.38 mmol) and $H_2O$ (0.05 mL) in $CH_3CN$ (7.2 mL) was added pyridinium trifluoroacetate (0.32 g, 1.66 mmol) at 25° C. After 2 min, TLC ($CH_2Cl_2$:MeOH=15:1, Rf=0.5) showed the starting material was consumed, and then t-butylamine (7.2 mL) was added. The final mixture was stirred at 25° C. for 10 min. The crude product was concentrated with MeCN (5 mL) (3×) to afford the crude compound 2a (crude, 1.2 g) as a white solid. The crude product was used directly for the next step without purification.

Step 2: Preparation of Compound 2b

To a solution of the crude compound 2a (1.2 g, 1.476 mmol, crude) and water (14.764 mmol, 0.266 mL) in $CH_2Cl_2$ (10 mL) was added dichloroacetic acid (6% in $CH_2Cl_2$, 6 mL) at 25° C. for 20 min. After 20 min, pyridine (233.56 mg, 2.953 mmol) was added. The reaction mixture was concentrated under pressure to give a residue. The residue was purified by flash column chromatography (silica gel, DCM/MeOH=100/1 to 3/1) to give compound 2b (440 mg, 58% yield) as a white foam. ESI-MS: m/z 432.2 $[M+H]^+$.

Step 3: Preparation of Compounds 2e+2f

To a solution of compound 2b (440 mg, 0.862 mmol) and 4 Å molecular sieves (1 g) in dry $CH_3CN$ (10 mL) was stirred at 15° C. under nitrogen for 10 min. After 10 min, 1H-imidazole perchlorate (2.70 g, 16.026 mmol) was added. The mixture was stirred at 25° C. for 10 min. After 10 min, compound 2c (981.56 mg, 1.12 mmol) in dry $CH_3CN$ (5 mL) was added. The mixture was stirred at 25° C. for 50 min. After 50 min, tert-butyl hydroperoxide (5.5 M in hexane, 0.784 mL, 4.310 mmol) was added. The final mixture was stirred at 15° C. for 1 h. The mixture was concentrated to give a residue and then the residue was purified by prep-HPLC (Column: Phenomenex Gemini C18 250*50 10 u; Condition:water (10 mM $NH_4HCO_3$)-ACN; Begin B: 48; End B: 78; FlowRate (mL/min): 22) to give compounds 2e+2f (120 mg, 15% yield) as a white solid. ESI-MS: m/z 921.1, 460.9 $[M+H]^+$.

Step 4: Preparation of Compound 2g+2h

To a solution of compounds 2e+2f (120 mg, 0.13 mmol) and 4 Å molecular sieves (1 g) in pyridine (50 mL) was added 2-chloro-5,5-dimethyl-1,3,2-dioxaphosphinane 2-oxide (72.242 mg, 0.391 mmol) at 25° C. The solution was stirred at 25° C. for 1 hour. After 1 hour, the solution of compounds 2g+2h (50 mL, crude) was used directly for the next step without further purification.

Step 5: Preparation of Compounds 2i+2j

To a solution of compounds 2g+2h (50 mL, crude) was added water (0.02 mL) and then 12 (140.7 mg, 0.556 mmol) was added at 25° C. The solution was stirred at 25° C. for 1 hour. After 1 h, the reaction was quenched with $Na_2SO_3$ (aq). The mixture was filtered and concentrated to give a residue, which was purified by prep-HPLC (column: Boston Green ODS 150*30 5 u; mobile phase: water (10 mM $NH_4HCO_3$)-ACN, flow rate: 25 ml/min) to afford compound 2i (10 mg, 10% yield) as a white solid (ESI-MS: m/z 918.2 [M+H]$^+$) and compound 2j (45 mg, 47% yield) as a white solid (ESI-MS: m/z 865.2 [M+H]$^+$).

Step 6: Preparation of Compound 5, Ammonium Salt

Compound 2j (30 mg, 0.035 mmol) was treated with a solution of $MeNH_2$ in EtOH (33%, 2 mL) and the resultant mixture was stirred for 2 h. The solution was then concentrated under reduced pressure to give a white solid which was purify by reverse phase preparative HPLC (column: Agela Durashell C18 150×25 5 µM; mobile phase:water (0.05% ammonia hydroxide v/v)-ACN, flow rate: 35 ml/min) to afford compound 5 ammonium salt as a white solid (18 mg). $^1$H NMR (400 MHz, $D_2O$), 8.32 (br s, 1H), 8.17 (br s, 1H), 7.81 (br s, 1H), 6.39 (br, d, J=14.1 Hz, 1H), 5.86 (br, d, J=8.0 Hz, 1H), 5.72 (br, s, 1H), 5.55-5.32 (m, 1H), 5.15-4.96 (m, 1H), 4.49 (br, s, 2H), 4.38 (br s, 1H), 4.20 (br, d, J=19.8 Hz, 3H), 4.07 (br, s, 1H), 3.55 (s, 3H). ESI-MS: m/z 691.1, 345.9 [M+H]$^+$.

Step 7: Preparation of Compound 5 Sodium Salt

Dowex 50W×8, 200-400 (H form, 5 mL) was added to a beaker (for 18 mg of compound 5 ammonium salt) and washed with DI $H_2O$ (2×). Then to the resin was added 15% $H_2SO_4$ in DI $H_2O$ (50 mL), the mixture was stirred for 15 min, and decanted (1×). The resin was transferred to a column with 15% $H_2SO_4$ in DI $H_2O$ and washed with 15% $H_2SO_4$ (at least 4 CV), and then with DI $H_2O$ until it was neutral. The resin was transferred back into the beaker, and 15% NaOH in $H_2O$ solution (50 mL) was added, and the mixture was stirred for 15 min, and decanted (1×). The resin was transferred to the column and washed with 15% NaOH in $H_2O$ (at least 4 CV), and then with $H_2O$ until it was neutral (at least 4 CV). Compound 5 ammonium salt was dissolved in DI water (18 mg in 2 mL), added to the top of the column, and eluted with DI water. The converted sodium salt was eluted out in early fractions as detected by TLC (UV). The product was lyophilized to give compound 5 sodium salt (14.8 mg, 77% yield) as a white solid. $^1$H NMR (400 MHz, $D_2O$), 8.23 (br, d, J=6.5 Hz, 2H), 7.82 (s, 1H), 6.42 (br, d, J=14.2 Hz, 1H), 5.87 (br, d, J=8.4 Hz, 1H), 5.67 (br, d, J=4.4 Hz, 1H), 5.59-5.42 (m, 1H), 5.18-5.05 (m, 1H), 4.57-4.50 (m, 2H), 4.46 (br, d, J=12.4 Hz, 1H), 4.21 (br, s, 3H), 4.13 (br, d, J=12.8 Hz, 1H), 3.55 (s, 3H); $^{19}$F NMR (376 MHz, $D_2O$) −202.946; $^{31}$P NMR (162 MHz, $D_2O$) −1.422, −2.618; ESI-MS: m/z 690.8 [M+H]$^+$.

Batch2:

Step 6: Preparation of Compound 5 Ammonium Salt

Compound 2j (15 mg, 0.017 mmol) was treated with a solution of $MeNH_2$ in EtOH (33%, 1 mL) and the resultant solution was stirred for 5 h. After 5 h, the solution was concentrated under reduced pressure to give a residue, which was purified by purified by reverse phase preparative HPLC (column: Agela Durashell C18 150×25 5 µM; mobile phase: water (0.05% ammonia hydroxide v/v)-ACN, flow rate: 35 mL/min) to afford compound 5 ammonium salt (8 mg, 67% yield) as a white solid. $^1$H NMR (400 MHz, $D_2O$) 8.24 (d, J=8.3 Hz, 2H), 7.82 (s, 1H), 6.43 (d, J=14.1 Hz, 1H), 5.88 (d, J=8.5 Hz, 1H), 5.70-5.64 (m, 1H), 5.59-5.44 (m, 1H), 5.19-5.06 (m, 1H), 4.56-4.50 (m, 2H), 4.47 (br, d, J=12.8 Hz, 1H), 4.22 (br, d, J=4.0 Hz, 3H), 4.13 (br, d, J=12.3 Hz, 1H), 3.55 (s, 2H), 3.58-3.53 (m, 1H); ESI-MS: m/z 690.8 [M+H]$^+$.

Step 7: Preparation of Compound 5, Sodium Salt

Dowex 50W×8, 200-400 (H form) was added to a beaker (for 8 mg of compound 5 ammonium salt) and washed with DI $H_2O$ (2×). Then to the resin was added 15% $H_2SO_4$ in DI $H_2O$ (50 mL), the mixture was stirred for 15 min, and decanted (1×). The resin was transferred to a column with 15% $H_2SO_4$ in DI $H_2O$ and washed with 15% $H_2SO_4$ (at least 4 CV), and then with DI $H_2O$ until it was neutral. The resin was transferred back into the beaker, and 15% NaOH in $H_2O$ solution (50 mL) was added, and the mixture was stirred for 15 min, and decanted (1×). The resin was transferred to the column and washed with 15% NaOH in $H_2O$ (at least 4 CV), and then with $H_2O$ until it was neutral (at least 4 CV). Compound 5 was dissolved in DI water (8 mg in 2 mL), added to the top of the column, and eluted with DI water. The converted sodium salt was eluted out in early fractions as detected by TLC (UV). The product was lyophilized to give compound 5 MHz, $D_2O$), 8.20 (br, d, J=11.0 Hz, 2H), 7.78 (s, 1H), 6.40 (br, d, J=14.1 Hz, 1H), 5.85 (d, J=8.8 Hz, 1H), 5.62 (br, d, J=4.3 Hz, 1H), 5.57-5.41 (m, 1H), 5.16-5.02 (m, 1H), 4.53-4.46 (m, 2H), 4.42 (br d, J=13.3 Hz, 1H), 4.18 (br, d, J=4.0 Hz, 3H), 4.10 (br d, J=9.5 Hz, 1H), 3.51 (s, 3H). $^{19}$F NMR (376 MHz, $D_2O$): −202.954; $^{31}$P NMR (162 MHz, $D_2O$): −1.458, −2.582; ESI-MS: m/z 690.8 [M+H]$^+$.

Example 3

Cpd 1

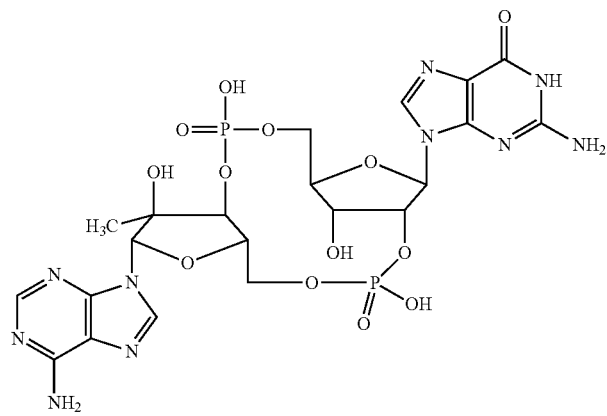

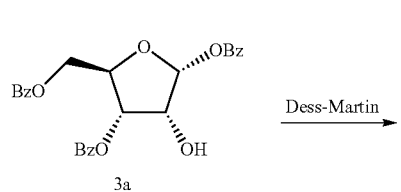
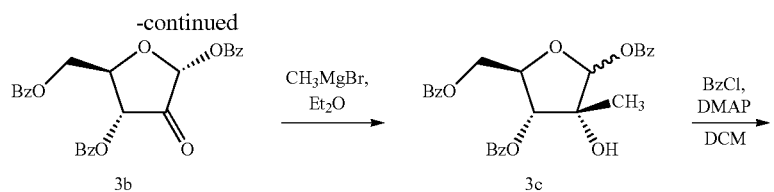
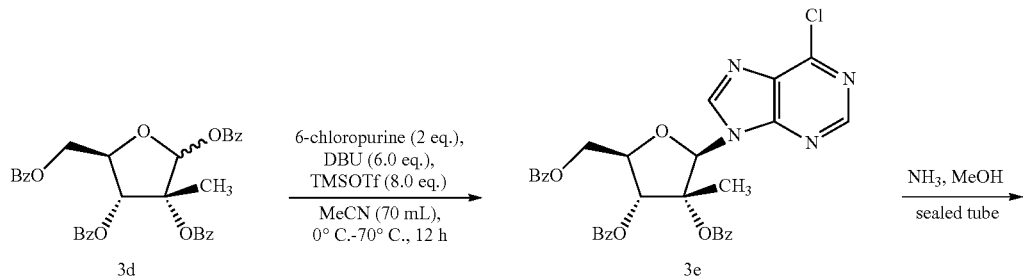
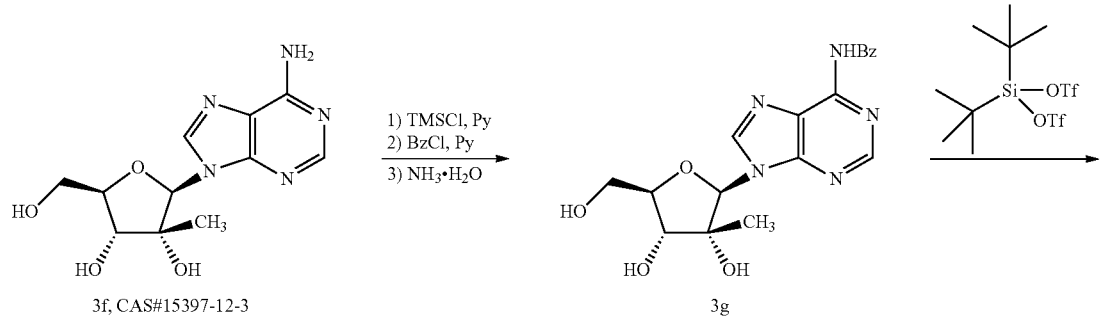
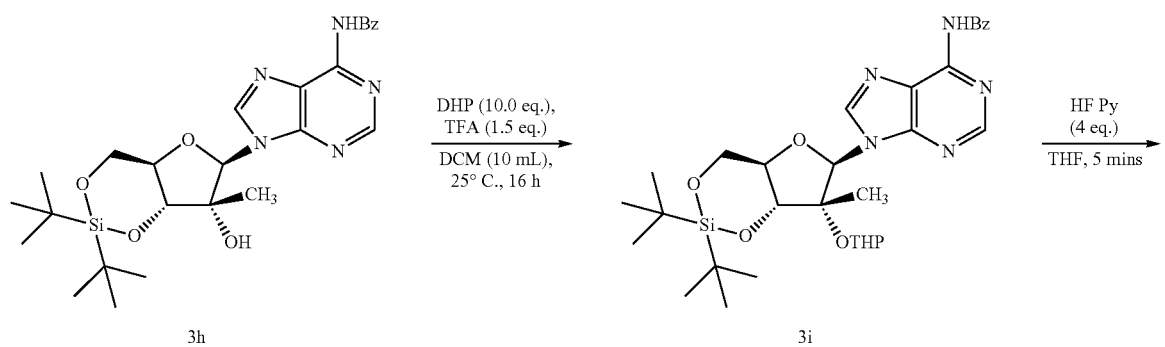
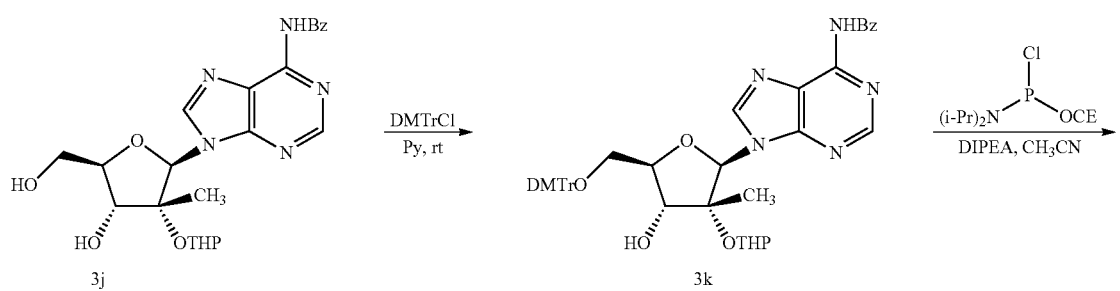

-continued
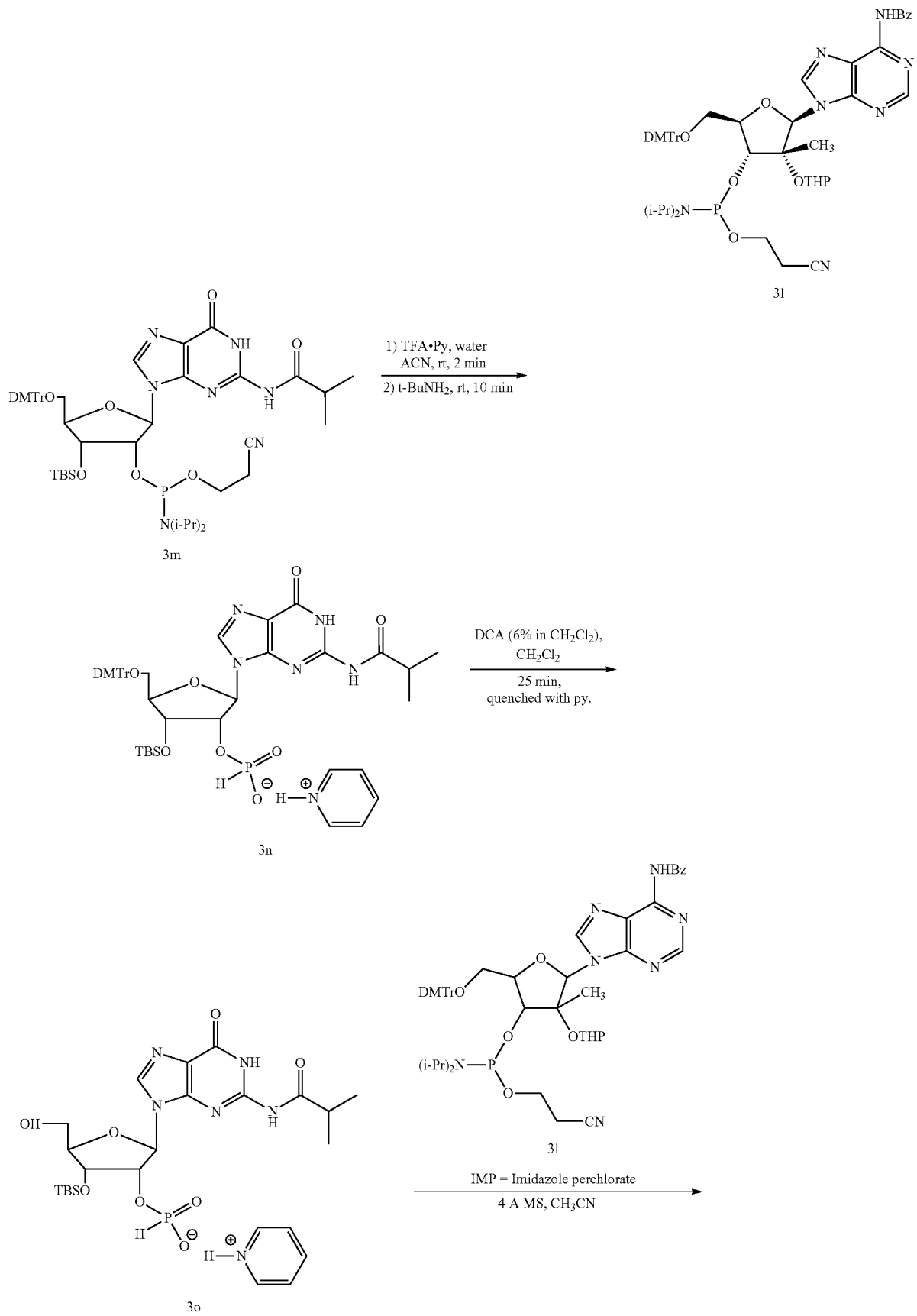

-continued
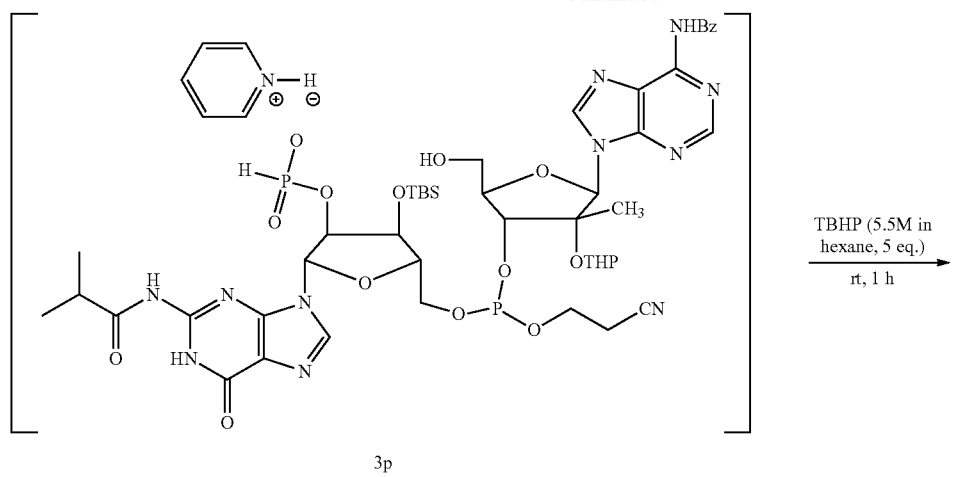
3p
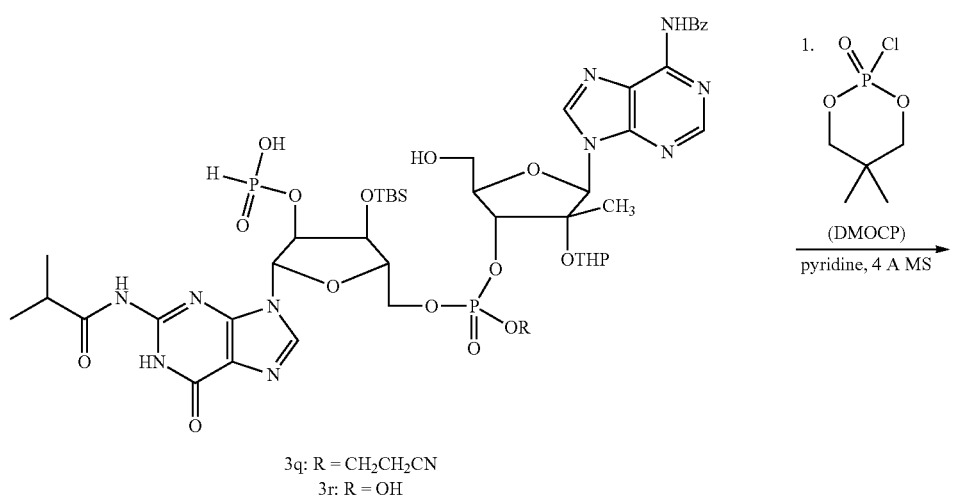
3q: R = CH₂CH₂CN
3r: R = OH
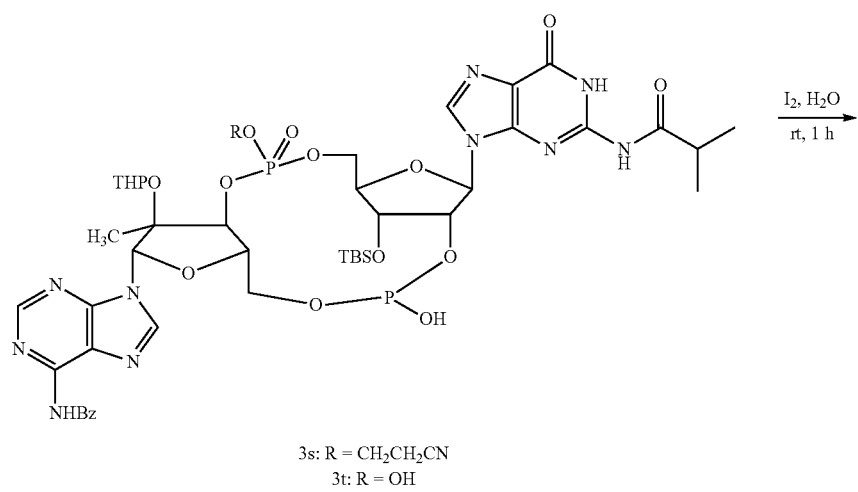
3s: R = CH₂CH₂CN
3t: R = OH -continued
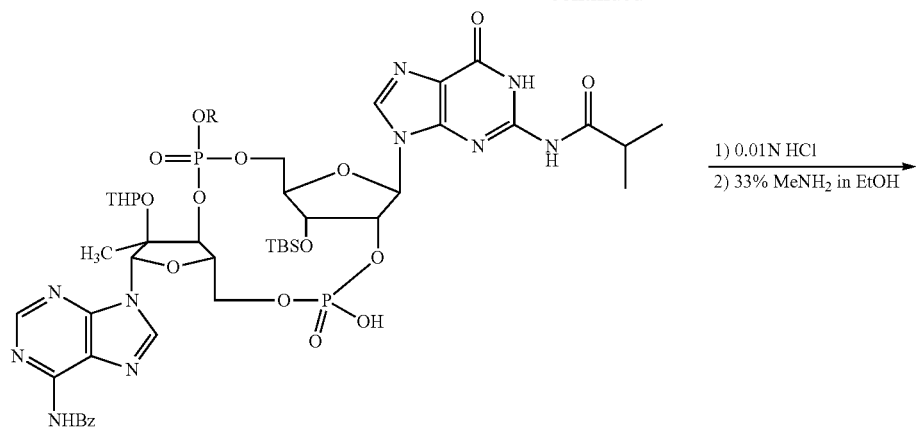
3u: R = CH₂CH₂CN
3v: R = OH
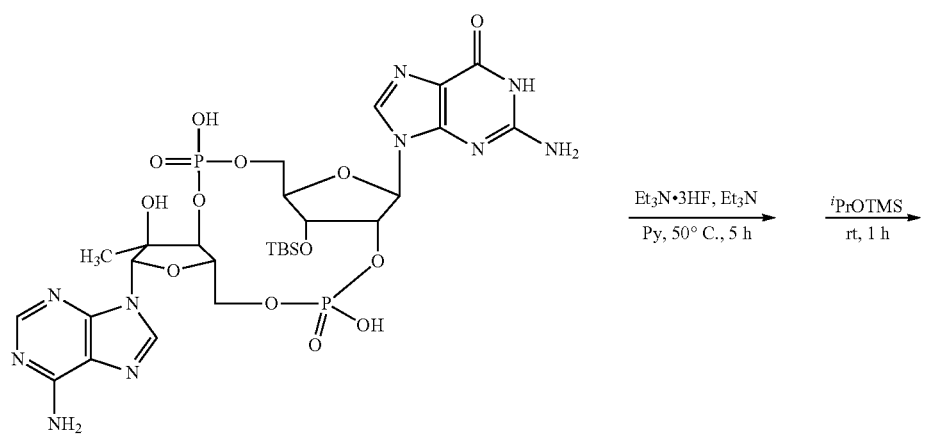
3w
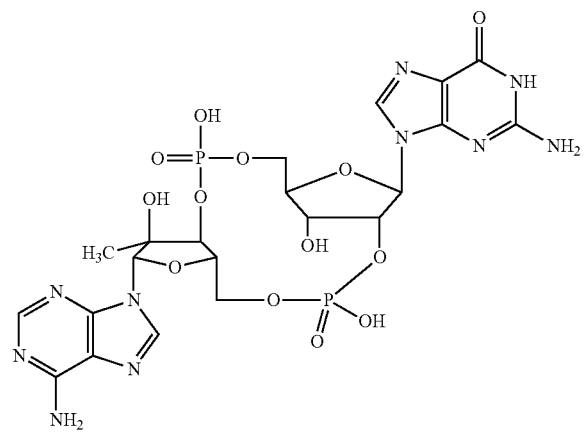
Compound 1, ammonium salt

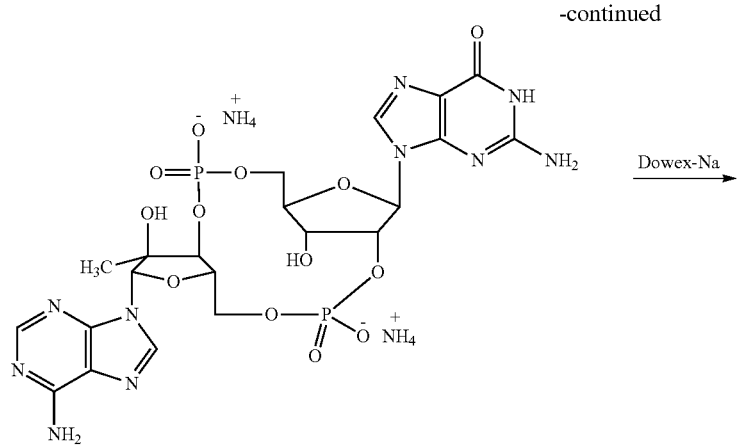

Compound 1, ammonium salt

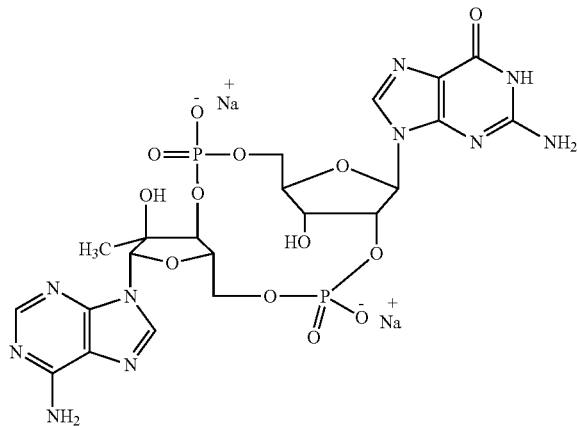

Compound 1, sodium salt

Step 1: Preparation of Compound 3b

To a solution of compound 3a (50.0 g, 108.12 mmol, 1.0 eq) in MeCN (500 mL) was added IBX (45.413 g, 162.18 mmol, 1.5 eq). The mixture was stirred at 80° C. for 12 h. The reaction mixture was cooled to room temperature and filtered. The filtrate was concentrated to dryness to give crude compound 3b (57.0 g, light yellow oil), which was used for the next step without further purification.

Step 2: Preparation of Compound 3c

Compound 3b was co-evaporated with anhydrous toluene three times to remove water. Then a solution of MeMgBr (76 mL, 228.047 mmol, 3 M in Et$_2$O, 3.0 eq) was added dropwise into a solution of compound 3b (35 g, crude) in THF (400 mL) over 20 min at −78° C. and the resulting mixture was stirred for about 2 h at −78° C. The dry ice-acetone cooling bath was removed, and the mixture was poured into a solution of saturated NH$_4$Cl (300 mL) with stirring. After warming to 25° C., the mixture was extracted with EtOAc (500 mL), filtered through diatomaceous earth, and washed with brine (300 mL×3). The combined organic extracts were dried with anhydrous Na$_2$SO$_4$, filtered and concentrated to give crude product 3c (32 g, brown oil), which was used directly for the next step without further purification.

Step 3: Preparation of Compound 3d

To a solution of compound 3c (32 g, crude), DMAP (16.41 g, 134.32 mmol, 2.0 eq), Et$_3$N (20.39 g, 201.48 mmol, 3.0 eq) in CH$_2$Cl$_2$ (500 mL) was added BzCl (28.32 g, 201.48 mmol, 3.0 eq) at 0° C. The mixture was stirred at 25° C. for 12 h. The reaction mixture was diluted with CH$_2$Cl$_2$ (100 mL) and then washed with saturated aq. NaHCO$_3$ (100 mL). The aqueous phase was extracted with CH$_2$Cl$_2$ (100 mL) and the combined organic extracts were dried with Na$_2$SO$_4$, filtered and evaporated to dryness under reduced pressure to give a black oil. The residue was purified by column chromatography (SiO$_2$, petroleum ether/EtOAc=10/1 to EtOAc) to afford compound 3d (19.0 g, 49% yield) as a white solid. ESI-MS m/z 603.1 (M+Na)$^+$.

Step 4: Preparation of Compound 3e

Compound 3d and 6-chloro-9H-purine were co-evaporated with anhydrous toluene (3×) to remove water. To a stirred suspension of compound 3d (17.0 g, 29.281 mmol, 1.0 eq) and 6-chloro-9H-purine (9.051 g, 58.562 mmol, 2.0 eq) in anhydrous MeCN (300 mL) was added DBU (26.746 g, 175.686 mmol, 6.0 eq) at 0° C. The mixture was stirred at 0° C. for 15 min and then TMSOTf (52.064 g, 234.248 mmol, 8.0 eq) was added dropwise at 0° C. After the addition, the mixture was stirred at 0° C. for 15 min until a clear solution was achieved. The mixture was then heated to 70° C. and stirred for 12 h. The reaction was cooled to room temperature and diluted with $CH_2Cl_2$ (200 mL). To the solution was added sat. $NaHCO_3$ (100 mL), and the organic layer was washed with brine (2×100 mL), dried over $Na_2SO_4$, filtered, and concentrated under reduced pressure to give a residue. The crude product was purified by column chromatography ($SiO_2$, petroleum ether/EtOAc=10/1 to 5/1) to afford compound 3e (15.0 g, 84% yield) as a white solid.

Step 5: Preparation of Compound 3f

Compound 3d (4.6 g, 7.504 mmol) and $NH_3$ (70.0 mL, 7 M in MeOH) was stirred at 50° C. for 24 h. The solution was concentrated under reduced pressure to give a residue. The solution was concentrated under reduced pressure to give a residue. The crude product was crystallized from $CH_2Cl_2$/MeOH=10/1 (30 mL) to give compound 3f (76% yield) as a white solid. $^1H$ NMR (400 MHz, DMSO-$d_6$) 8.46 (s, 1H), 8.14 (s, 1H), 7.29 (s, 2H), 5.94 (s, 1H), 5.24 (s, 3H), 4.07 (d, J=9.0 Hz, 1H), 3.96-3.78 (m, 2H), 3.69 (d, J=10.0 Hz, 1H), 0.76 (s, 3H).

Step 6: Preparation of Compound 3g

To a solution of compound 3f (3.0 g, 10.666 mmol, 1.0 eq) in pyridine (30.0 mL) was added TMSCl (6.953 g, 63.996 mmol, 6.0 eq) at 0° C. Then the mixture was stirred at 25° C. for 2 h. The reaction mixture (0.356 M in Py, 30 mL) was used for the next step without purification.
BzCl (2.999 g, 21.332 mmol, 2.0 eq) was added to the solution. The reaction mixture was stirred at 25° C. for 12 h. $NH_3$—$H_2O$ (1.869 g, 53.33 mmol, 5.0 eq) was added to the solution, then the reaction mixture was stirred at 25° C. for 3 h. The solution was concentrated under pressure to give a residue, which was purified by flash column chromatography ($SiO_2$, $CH_2Cl_2$/MeOH=100/1 to 10/1) to afford compound 3g (3.2 g, 78% yield) as a white solid. ESI-MS m/z 386.0 $(M+1)^+$.

Step 7: Preparation of Compound 3h

To a solution of compound 3g (1.3 g, 3.373 mmol, 1.0 eq) in DMF (20 mL) was added di-tert-butylsilanediyl bis (trifluoromethanesulfonate) (1.634 g, 3.711 mmol, 1.1 eq.) dropwise at 0° C. The mixture was stirred at 0° C. for 2 h. 1H-Imidazole (1.148 g, 16.867 mmol, 5.0 eq) was added to the reaction mixture at 0° C. and the reaction was stirred at 25° C. for 30 min. The mixture was diluted with EtOAc (50 mL), washed with brine (3×50 mL), dried over $Na_2SO_4$, filtered and concentrated under pressure to give a residue. The residue was purified by column chromatography on silica gel (petroleum ether/EtOAc=10/1 to 1/1) to give compound 3h (1.32 g, 74% yield) as a white solid.

Step 8: Preparation of Compound 3i

To a solution of compound 3h (620 mg, 1.179 mmol, 1.0 eq) and 3,4-dihydro-2H-pyran (0.992 g, 11.794 mmol, 10.0 eq) in $CH_2Cl_2$ (8 mL) was added trifluoroacetic acid (201.725 mg, 1.769 mmol, 1.5 eq.) at 0° C. Then the reaction mixture was stirred at 25° C. for 16 h. The reaction mixture was diluted with $CH_2Cl_2$ (20 mL) and quenched with $Et_3N$ (1 mL). Then the solution was washed with brine (2×10 mL), dried over $Na_2SO_4$, filtered and concentrated under reduced pressure to give a residue, which was purified by flash chromatography on silica gel (petroleum ether/EtOAc=10/1 to 3/1) to afford compound 3i (552 mg, 77% yield) as a white foam.

Step 9: Preparation of Compound 3j

Pyridine hydrofluoride (326.23 uL, 3.621 mmol, 4.0 eq) was carefully diluted with pyridine (1.5 mL) and then added dropwise to a solution of compound 3i (552 mg, 0.905 mmol, 1.0 eq.) in THF (5 mL) at 0° C. The mixture was warmed to 25° C. and stirred for 5 min. The reaction mixture was quenched by addition of pyridine (1.5 mL) and diluted with $CH_2Cl_2$ (20 mL). The mixture was washed with brine (2×10 mL), dried over $Na_2SO_4$, filtered and the filtrate concentrated under pressure to give a residue. The residue was purified by flash column chromatography on silica gel (petroleum ether/EtOAc=10/1 to 0/1) to afford compound 3j (93.79% yield) as a white foam.

Step 10: Preparation of Compound 3k

To a solution of compound 3j (736 mg, 1.568 mmol, 1.0 eq.) in pyridine (10.0 mL) was added DMTrCl (796.748 mg, 2.351 mmol, 1.5 eq) at 25° C. The solution was stirred at 25° C. for 2 h. The reaction mixture was quenched by addition MeOH (2.0 mL), diluted with EtOAc (20 mL), and washed with brine (3×10 mL). The organic phase was dried over $Na_2SO_4$, filtered and the filtrate concentrated under reduced pressure to give a residue, which was purified by flash column chromatography on silica gel (petroleum ether/EtOAc=10/1 to 0/1) to afford compound 3k (1.13 g, 93% yield) as a white solid.

Step 11: Preparation of Compound 3l

To a solution of compound 3k (1.13 g, 1.464 mmol, 1.0 eq.) in THF (8.0 mL) was quickly added N, N-diisopropylethylamine (1.135 g, 8.784 mmol, 6.0 eq) and 2-cyanoethyl N,N-diisopropylchlorophosphoramidite (1.039 g, 4.392 mmol, 3.0 eq) at 0° C. under an argon atmosphere. The reaction mixture was then warmed to 25° C. and stirred for 2 h. The reaction mixture was diluted with EtOAc (50 mL), washed with brine (2×20 mL), and the organic phase was dried over $Na_2SO_4$, filtered, and the filtrate concentrated under reduced pressure. The resultant residue was purified by flash column chromatography on silica gel (petroleum ether/EtOAc=10/1 to 3/1) to afford compound 3l (1.25 g, 88% yield) as a white foam. $^{31}P$ NMR (162 MHz, $CDCl_3$) 151.242, 150.783, 149.656, 149.209; ESI-MS m/z 889.2 $(M-N(iPr)_2+17)^+$.

Step 12: Preparation of Compound 3n

To a solution compound 3m (1.0 g, 1.031 mmol, 1.0 eq) and water (37.138 mg, 2.061 mmol, 2.0 eq) in MeCN (5.0 mL) was added pyridinium trifluoroacetate (238.872 mg, 1.237 mmol, 1.2 eq) at 25° C. The reaction mixture was stirred at 25° C. for 5 min. After 5 min, t-butylamine (5.0 mL) was added. The reaction mixture was stirred at 25° C. for 15 min. The mixture was then concentrated under reduced pressure to form a foam. The residue was dissolved in $CH_3CN$ (5.0 mL) and concentrated under reduced pressure to afford a foam again. This process was repeated one more time to afford compound 3n (859.79 mg, crude) as a white foam. The crude product was used directly for the next step without further purification.

Step 13: Preparation of Compound 3o

To a solution of compound 3n (859.79 mg, 1.031 mmol, 1.0 eq) and water (185.738 mg, 10.31 mmol, 10 eq) in $CH_2Cl_2$ (12 mL) was added dichloroacetic acid (6% in $CH_2Cl_2$, 12 mL) at 0° C. The mixture was stirred at 25° C. for 1 h. Pyridine (2.0 mL) was added to quench the reaction. The reaction mixture was stirred at 25° C. for 30 min. The reaction mixture was concentrated under reduced pressure to give a residue, which was purified by flash column chromatography over silica gel (DCM/MeOH=10/1 to 5/1) to afford compound 3o (495 mg, 90% yield) as a white foam. $^1H$ NMR (400 MHz, DMSO-$d_6$) 8.18 (s, 1H), 7.82 (s, 2H), 5.78-5.70 (m, 1H), 5.07 (s, 1H), 4.90 (s, 1H), 4.23 (s, 1H), 3.78 (s, 1H), 3.69-3.57 (m, 1H), 3.50-3.31 (m, 2H), 2.71-2.57 (m, 2H), 0.99 (d, J=6.8 Hz, 6H), 0.77 (s, 9H), 0.01 (d, J=4.9 Hz, 6H); $^{31}P$ NMR (162 MHz, DMSO) 0.260 (s, 1P), −1.127 (s, 1P); ESI-MS m/z 532.1 $(M+1)^+$.

Step 14: Preparation of Compound 3p

A solution of compound 3o (650 mg, 1.223 mmol, 1.0 eq.) and 4 Å molecular sieves in MeCN (dry, 40 mL) was stirred at room temperature under a N2 atmosphere for 5 min. 1H-Imidazole perchlorate (2.085 g, 12.228 mmol, 10.0 eq) was added. After 10 min, compound 31 (1.248 g, 1.284 mmol, 1.05 eq) in MeCN (20.0 mL) was added. The mixture was stirred at 25° C. for 50 min, then the reaction mixture (0.02 M in MeCN, 60 mL) was used for the next step without further purification.

Step 15: Preparation of Compounds 3q+3r

To a solution of compound 3p (0.02 M in MeCN, 60 mL) was added tert-butyl hydroperoxide (1.112 mL, 6.115 mmol, 5.0 eq) at 25° C. The reaction mixture was stirred at 25° C. for 1 h. The reaction mixture was filtered, and the filtrate was concentrated under reduced pressure to give a residue, which was purified by reverse phase preparative HPLC (column: Waters Xbridge 150×25 5 μM; mobile phase: water (10 mM $NH_4HCO_3$)-ACN, B %: 37%-67%) to afford a mixture of compounds 3q+3r (360 mg of 3q and 130 mg of 3r) as a white solid. $^{31}P$ NMR (162 MHz, $CD_3OD$) 3.904, 2.553, −2.139, −2.242; ESI-MS: m/z=1116.5 $[M+1]^+$.

Step 16: Preparation of Compounds 3s+3t

To a solution of a mixture of compounds 3q+3r (120 mg, 0.108 mmol, 1.0 eq) and 4 Å molecular sieves in pyridine (40 mL) was added DMOCP (59.53 mg, 0.323 mmol, 3.0 eq) at 25° C. The mixture was stirred at 25° C. for 1 h, then the reaction mixture (0.0027 M in Py, 40 mL) was used directly for the next step.

Step 17: Preparation of Compound 3u+3v

To a solution of compounds 3s+3t (0.0027 M in Py, 40 mL) was added water (19.457 mg, 1.08 mmol, 10.0 eq) and 12 (137.057 mg, 0.54 mmol, 5.0 eq) at 25° C. The mixture was stirred at 25° C. for 1 h. The reaction was quenched with $Na_2SO_3$ (aq., 10 mL). The mixture was filtered and the filtrate concentrated under reduced pressure to give a residue, which was purified by reverse phase preparative HPLC (column: Waters Xbridge 150×25 5 μM; mobile phase: water (10 mM $NH_4HCO_3$)-ACN, B %: 20%-40%, FlowRate: 25 mL/min) to afford a mixture of compounds 3u+3v (25 mg, 21% yield) as white solid. $^{31}P$ NMR (162 MHz, Methanol-$d_4$) −1.94 (s, 1P), −1.98 (s, 1P).

Step 18: Preparation of Compound 3w

A mixture of compounds 3u+3v was treated with a solution of $MeNH_2$ in EtOH (33%, 3 mL) and the reaction was stirred at 25° C. for 16 h. The reaction mixture was concentrated under reduced pressure to give a crude product (26.8 mg) as a white solid, which was used for the next step without further purification.

To the crude product in water (2 mL) was added AcOH (aq. 10% in water, 2 mL). The reaction mixture was stirred at 25° C. for 5 h. The reaction mixture was neutralized with $Et_3N$ and the crude product was lyophilized to give compound 3w (30.5 mg) as a yellow solid. The crude was used for the next step without further purification.

Step 19: Preparation of Compound 1, Ammonium Salt

To a solution of compound 3w (30.5 mg, 0.038 mmol, 1.0 eq) in Py (2 mL) was added $Et_3N$ (384.49 mg, 3.8 mmol, 100 eq.) and $Et_3N$-3HF (306.271 mg, 1.9 mmol, 50 eq) at 25° C. The reaction mixture was stirred at 50° C. for 10 h. The mixture was dissolved in THF (3 mL) and isopropoxytrimethylsilane (502.607 mg, 3.8 mmol, 100 eq) was added at 25° C. and stirred for 1 h. The mixture was concentrated under reduced pressure to give a residue, which was purified by reverse phase preparative HPLC (column: Agela Durashell C18 150×25 5 μM; mobile phase: water (0.05% ammonia hydroxide v/v)-ACN from 0% to 10%, flow rate: 35 ml/min) to afford compound 1 ammonium salt (18 mg, 69% yield) as a white solid. $^1H$ NMR (400 MHz, $D_2O$) 8.44 (s, 1H), 8.18 (s, 1H), 7.97 (s, 1H), 5.80 (d, J=10.4 Hz, 2H), 5.62 (s, 1H), 4.61-4.55 (m, 1H), 4.52 (s, 1H), 4.41 (s, 1H), 4.35-4.10 (m, 4H), 3.92 (d, J=11.9 Hz, 1H), 1.13 (s, 3H); $^{31}P$ NMR (162 MHz, $D_2O$) −0.612 (s, 1P).

Step 20: Preparation of Compound 1, Sodium Salt

Compound 1, ammonium salt was dried under high vacuum to give a white solid (15 mg). Dowex 50W×8, 200-400 (H form, 3 mL) was added to a beaker (for 15 mg of cpd 7) and washed with de-ionized $H_2O$ (2×). Then to the resin was added 15% $H_2SO_4$ in de-ionized $H_2O$ (50 mL) and the mixture was stirred for 15 min and decanted (1×). The resin was transferred to a column with 15% $H_2SO_4$ in de-ionized $H_2O$ and washed with 15% $H_2SO_4$ (at least 4 CV), and then with de-ionized $H_2O$ until it was neutral. The resin was transferred back into the beaker, and 15% NaOH in de-ionized $H_2O$ solution (50 mL) was added and the mixture was stirred for 15 min and decanted (1×). The resin was transferred to the column and washed with 15% NaOH in de-ionized $H_2O$ (at least 4 CV), and then with de-ionized $H_2O$ until it was neutral (at least 4 CV). Compound 1 was dissolved in de-ionized $H_2O$ (15 mg in 2 mL), added to the top of the column, and eluted with de-ionized $H_2O$. The converted sodium salt was eluted out in early fractions as detected by TLC (UV). The product was lyophilized to give a first batch of compound 7, sodium salt (4.9 mg, 31% yield) as a white solid and a second batch of compound 1, sodium salt (6.2 mg, 37% yield) as a white solid. $^1H$ NMR (400 MHz, $D_2O$) 8.04 (s, 1H), 8.02 (s, 1H), 7.90 (s, 1H), 5.94 (s, 1H), 5.89 (d, J=8.4 Hz, 1H), 5.30 (dt, J=4.0, 8.8 Hz, 1H), 4.56 (t, J=8.4 Hz, 1H), 4.51 (d, J=4.0 Hz, 1H), 4.33-4.24 (m, 3H), 4.13-4.01 (m, 3H), 1.00 (s, 3H); $^{31}P$ NMR (162 MHz, $D_2O$) −1.125 (s, 1P), −2.066 (s, 1P). ESI-MS: m/z 688.9 $(M+1)^+$.

The reaction scheme illustrated under Example 4 describes one possible route to the preparation of compound 2 and pharmaceutically acceptable salt forms thereof, of the present invention.

Example 4
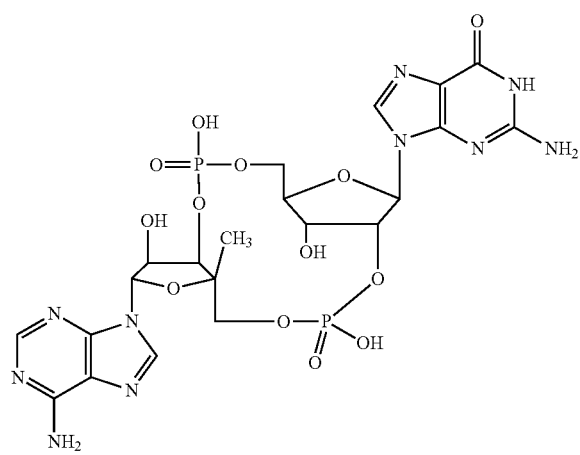
Cpd 2
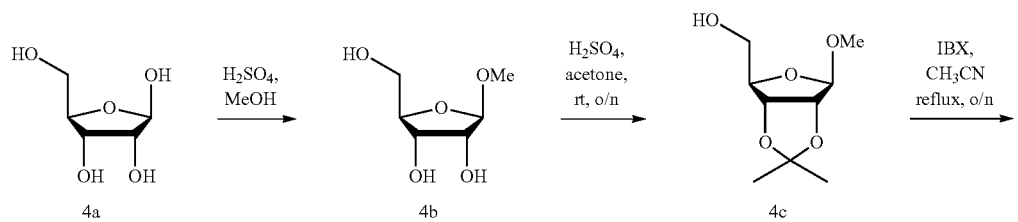
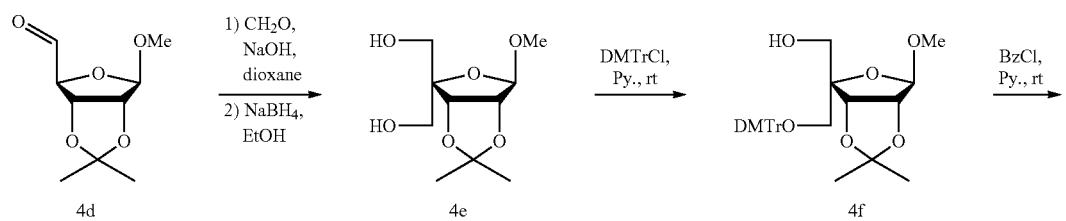
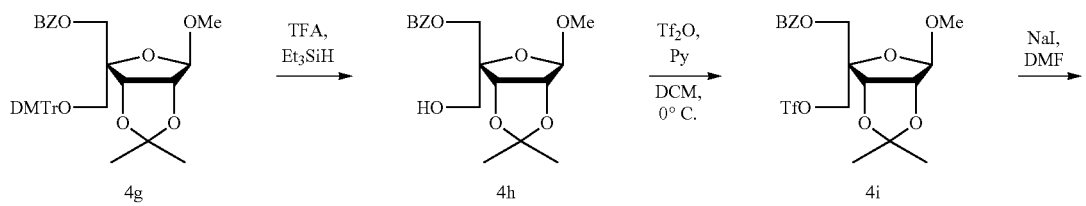
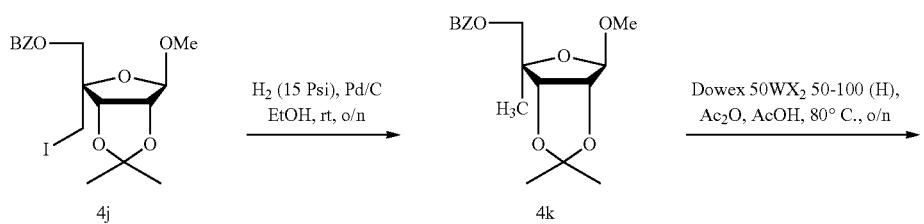

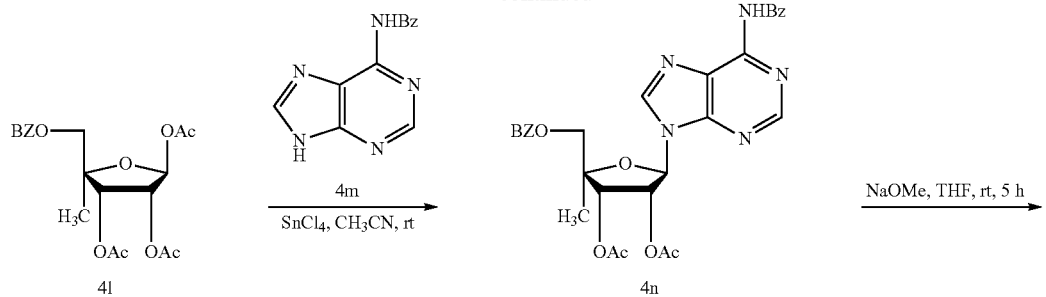
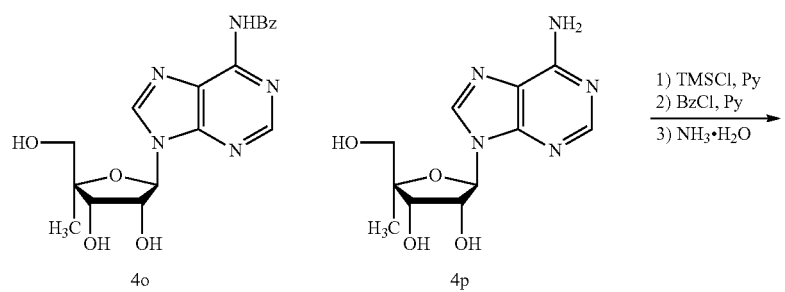
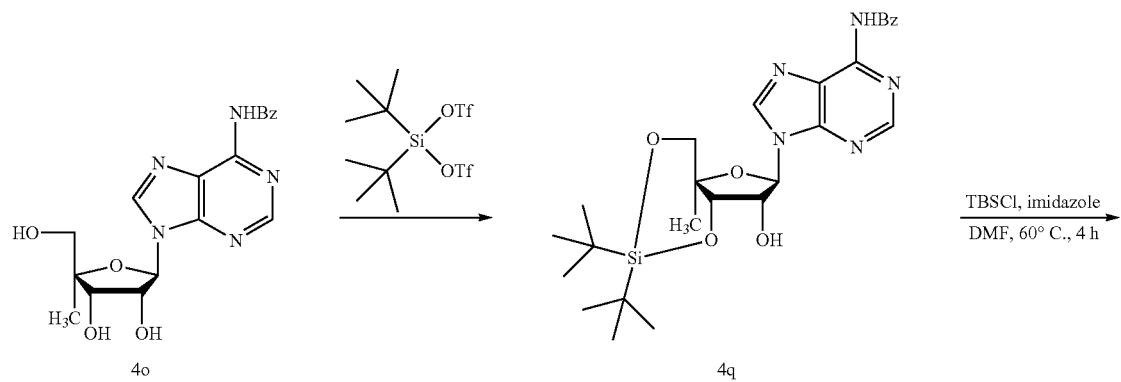
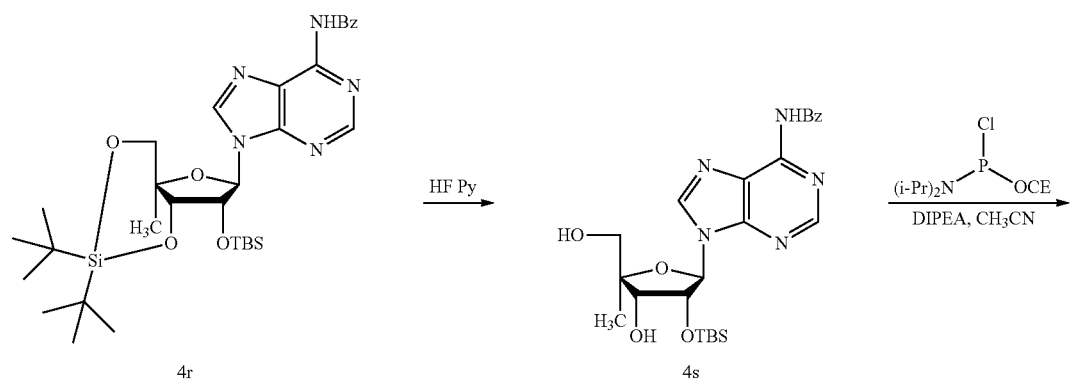

-continued
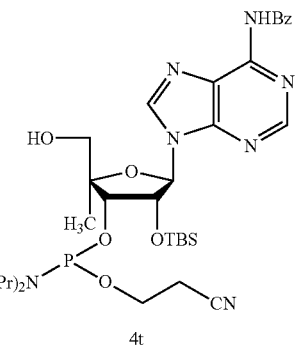
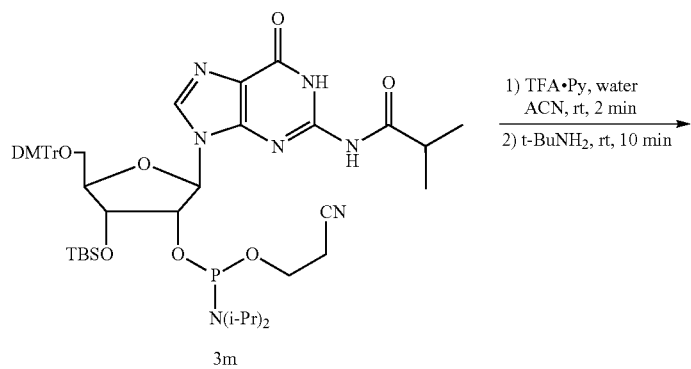
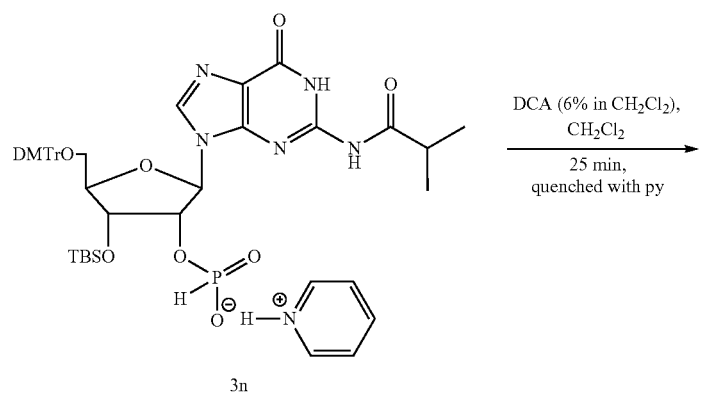
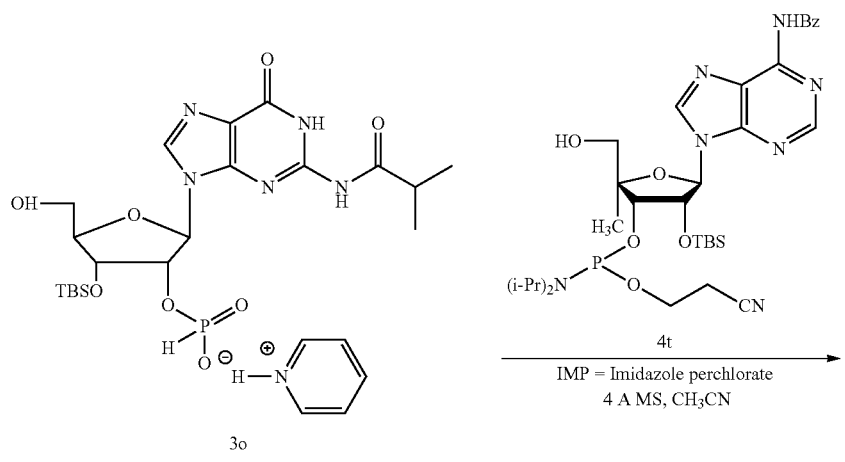

-continued
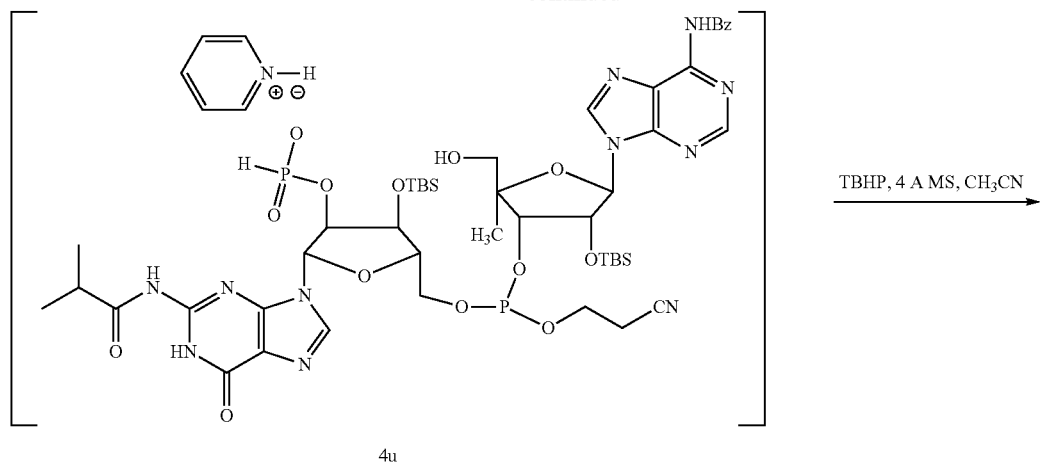
4u
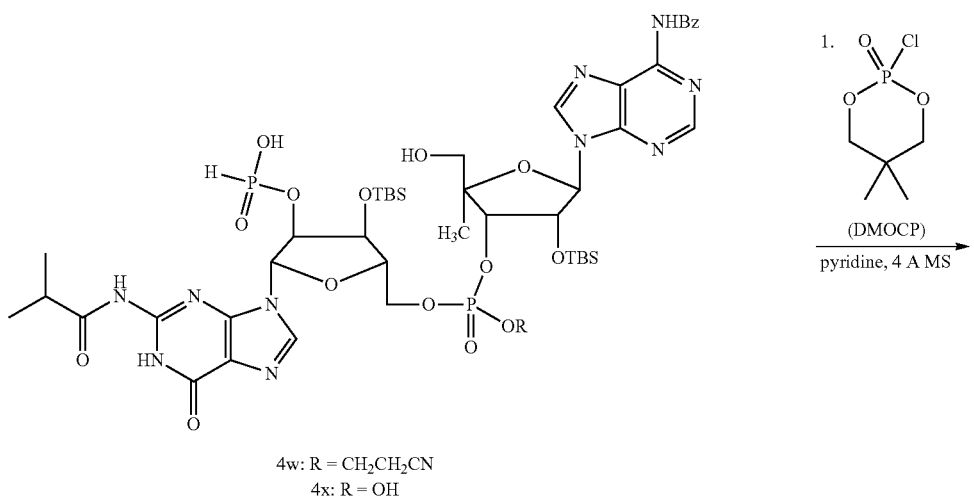
4w: R = CH₂CH₂CN
4x: R = OH
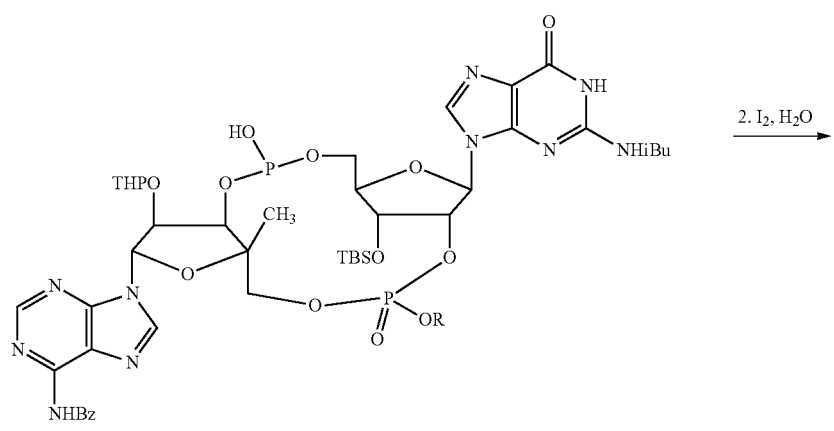
4aa: R = CH₂CH₂CN
4ab: R = OH -continued
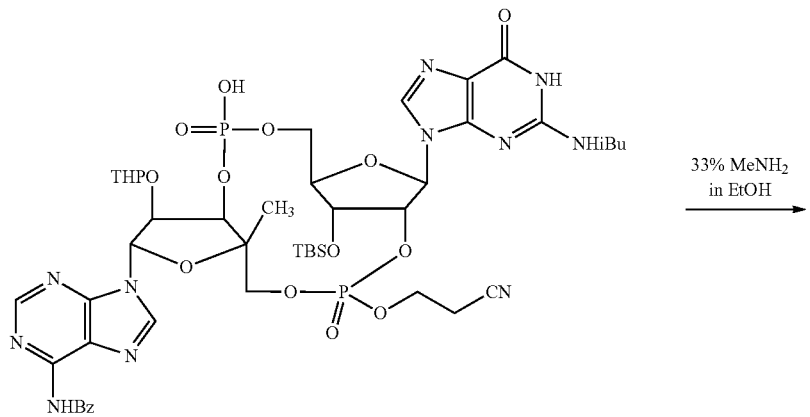
4ac: R = CH₂CH₂CN
4ad: R = OH
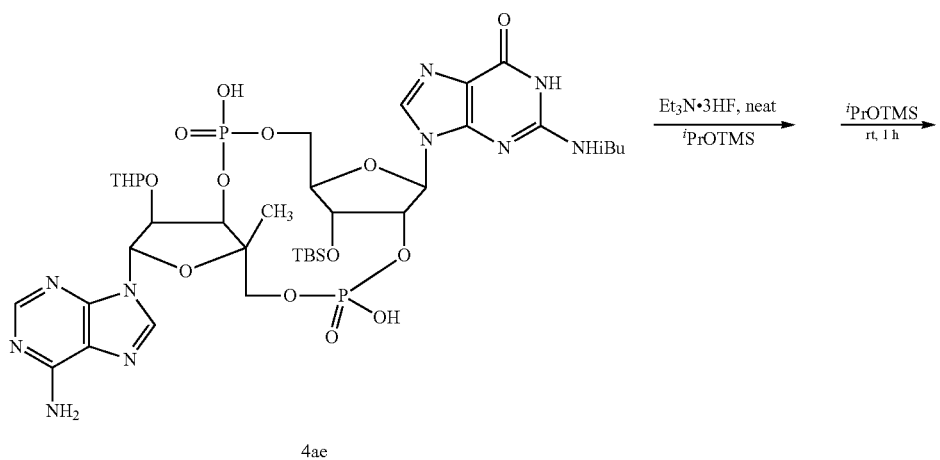
4ae
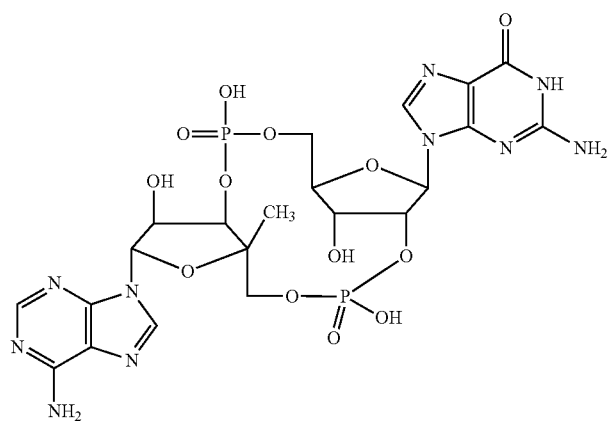
Compound 2, ammonium salt

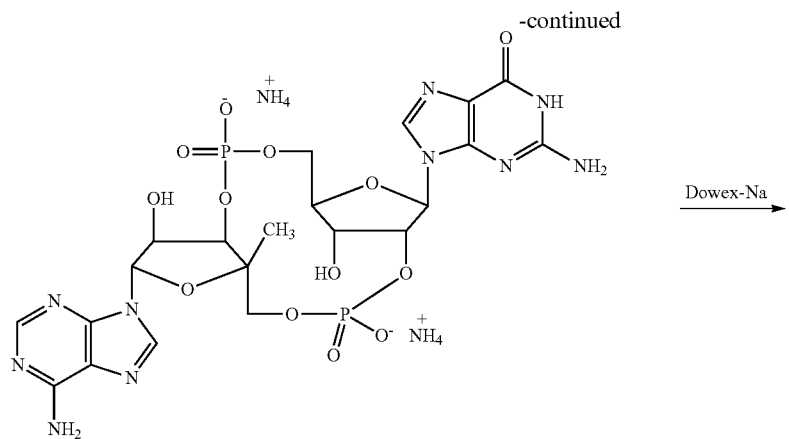
Compound 2, ammonium salt
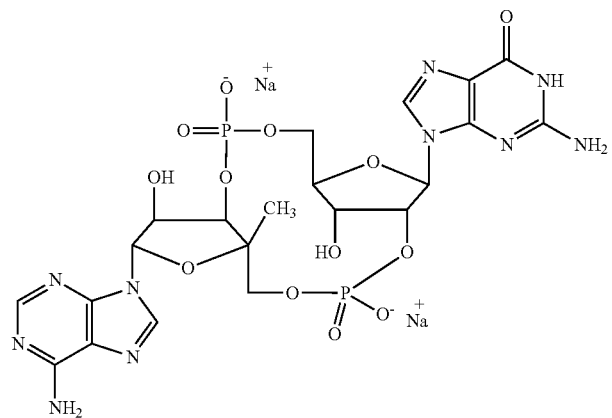
Compound 2, sodium salt
The reaction scheme illustrated under Example 5 describes one possible route for the preparation of compound 3 and pharmaceutically acceptable salt forms thereof, of the present invention.
Example 5
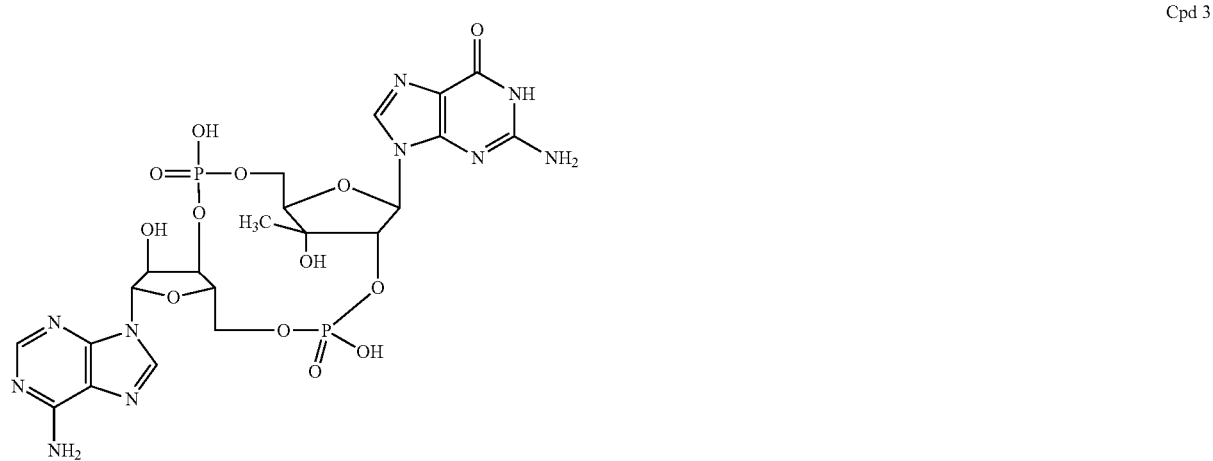
Cpd 3

-continued
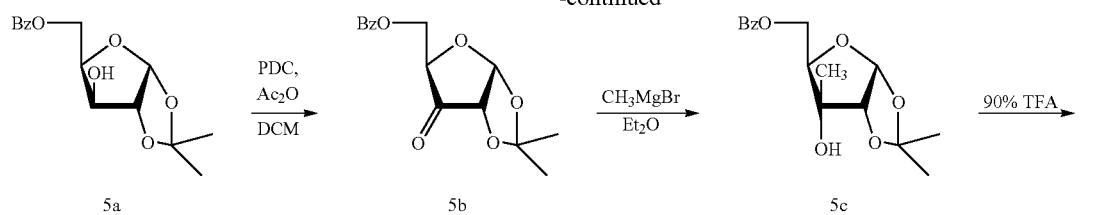
5a → 5b (PDC, Ac₂O, DCM) → 5c (CH₃MgBr, Et₂O) → 90% TFA →
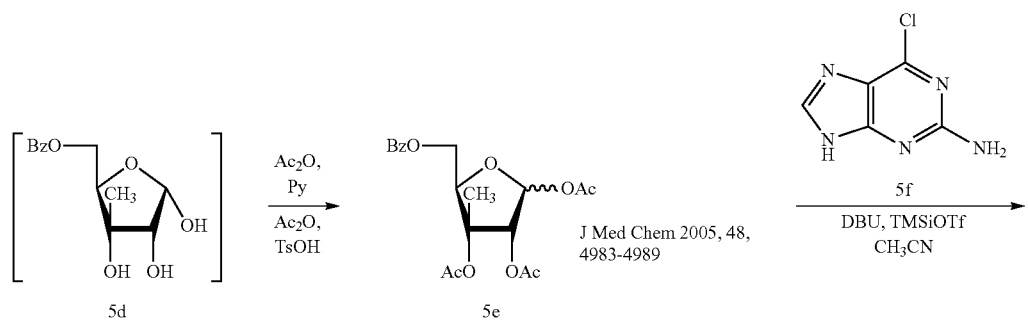
5d → 5e (Ac₂O, Py; Ac₂O, TsOH)
J Med Chem 2005, 48, 4983-4989
5f (DBU, TMSiOTf, CH₃CN) →
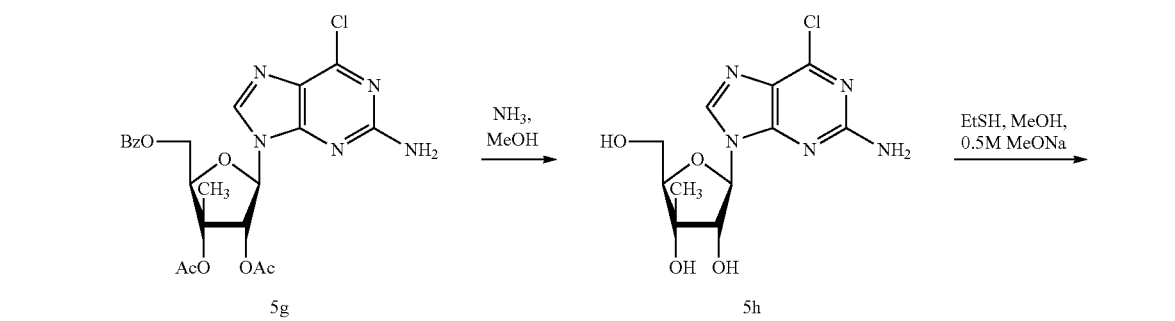
5g → 5h (NH₃, MeOH) → (EtSH, MeOH, 0.5M MeONa) →
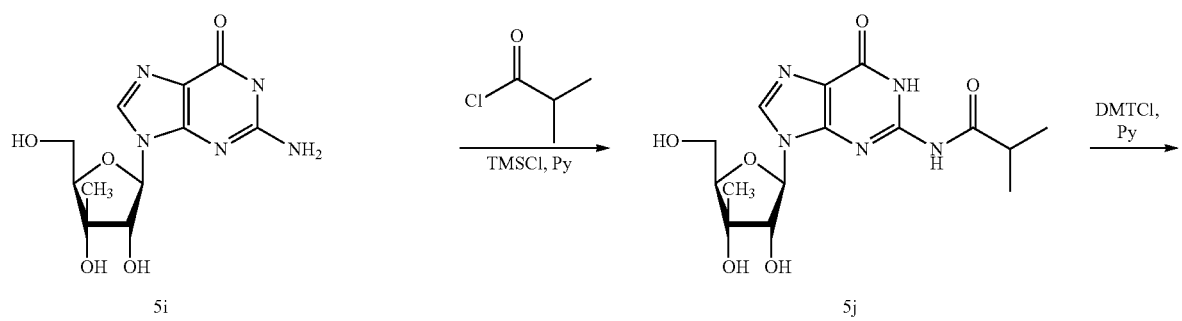
5i → 5j (iBuCOCl, TMSCl, Py) → (DMTCl, Py) →
Collect. Czech. Chem. Commun. 2006, 71, 1088-1098
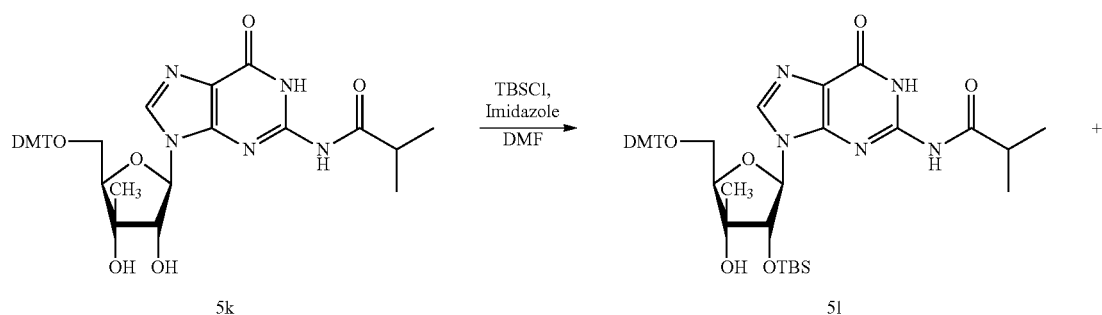
5k → 5l (TBSCl, Imidazole, DMF) +

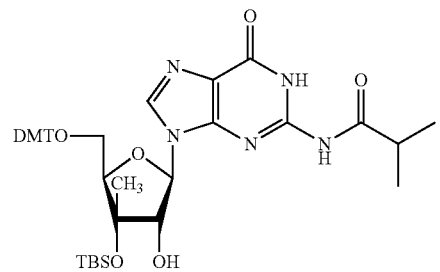
5m
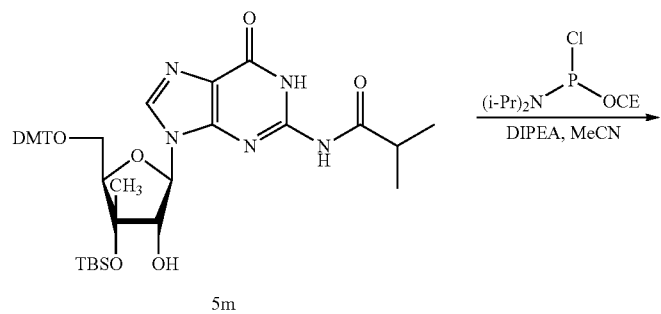
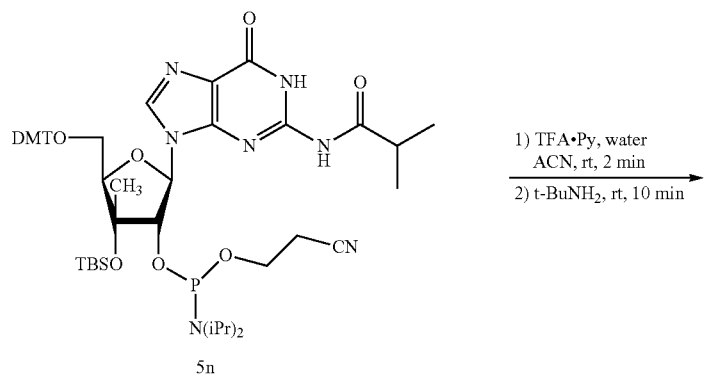
5n
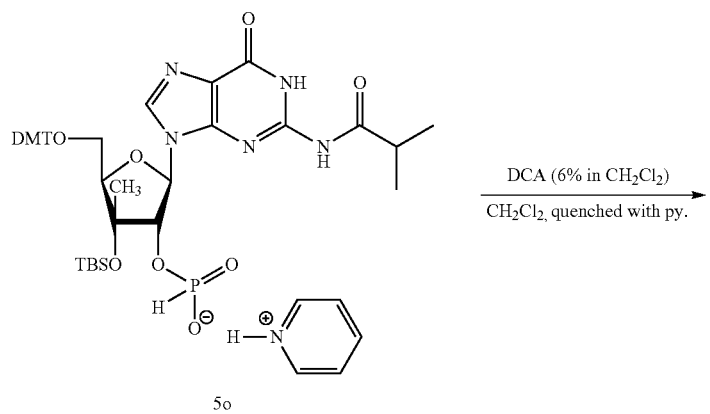
5o

-continued
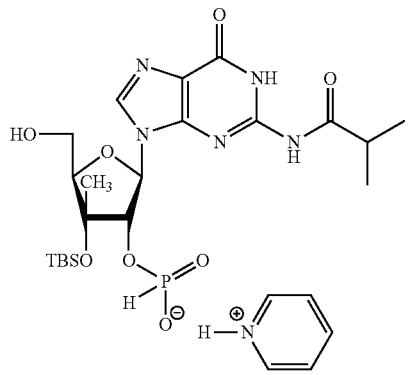 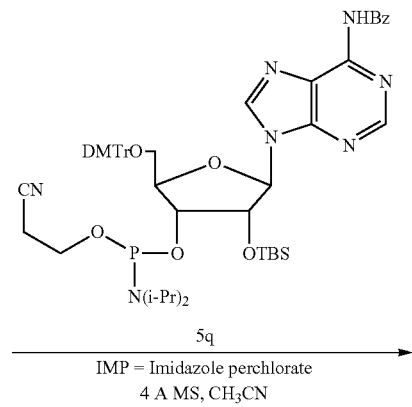
5p     5q
IMP = Imidazole perchlorate
4 A MS, CH₃CN
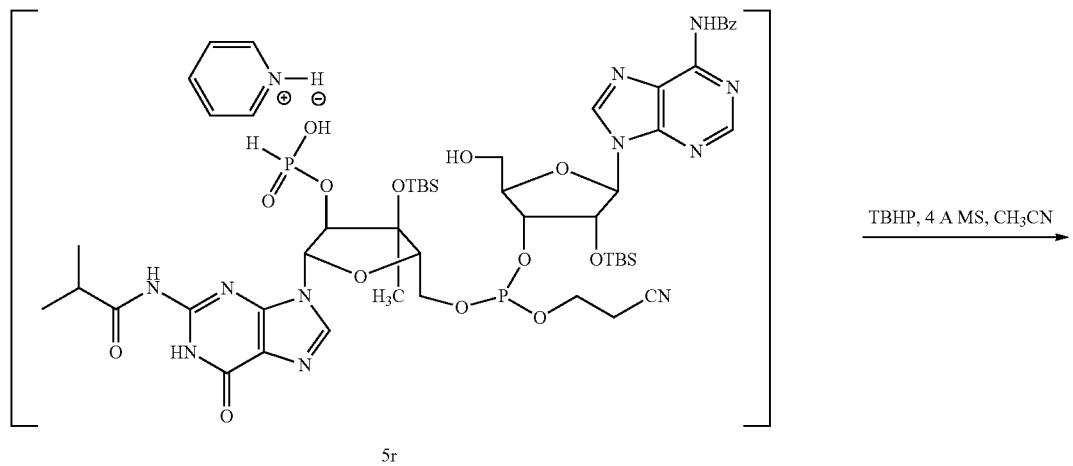
5r
TBHP, 4 A MS, CH₃CN
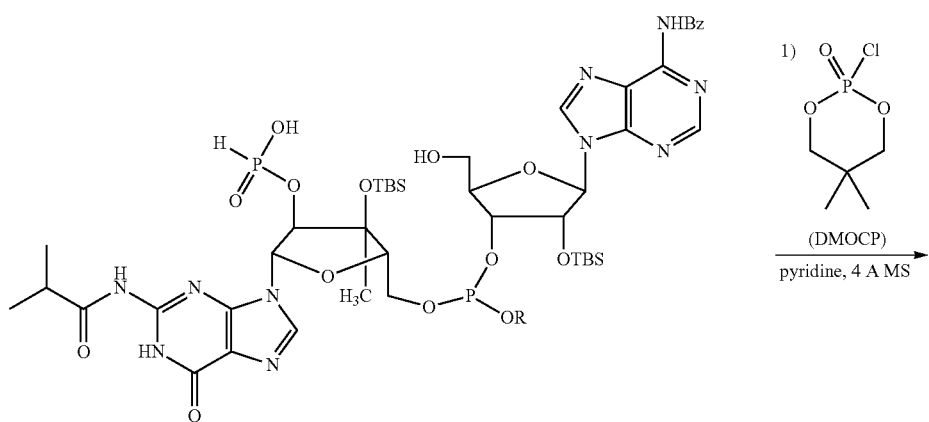 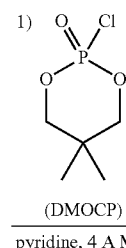
(DMOCP)
pyridine, 4 A MS
5s: R = OCH₂CH₂CN
5t: R = OH -continued
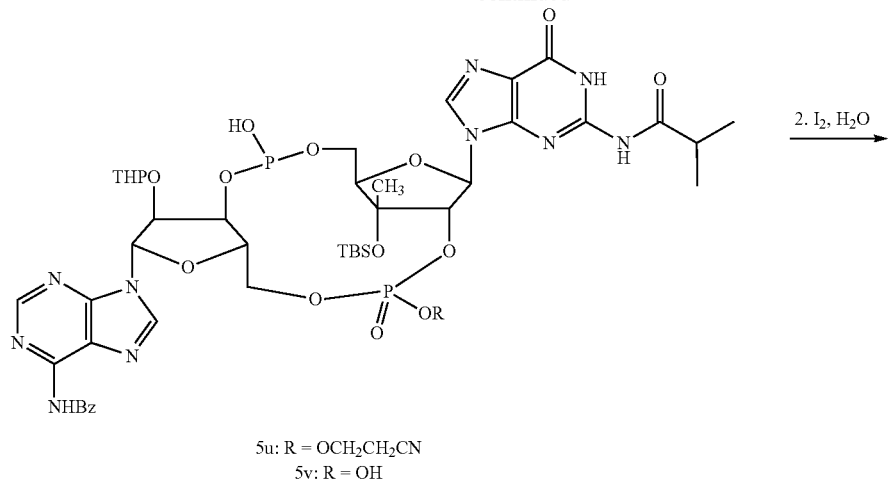
5u: R = OCH₂CH₂CN
5v: R = OH
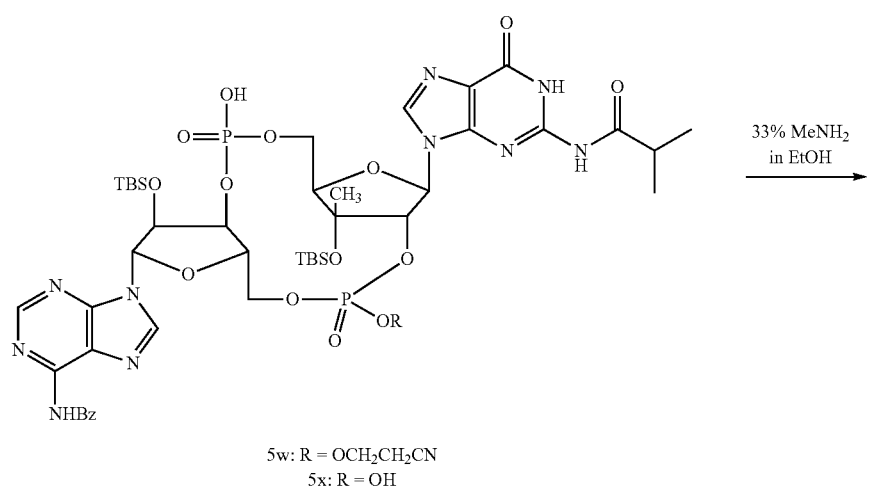
5w: R = OCH₂CH₂CN
5x: R = OH
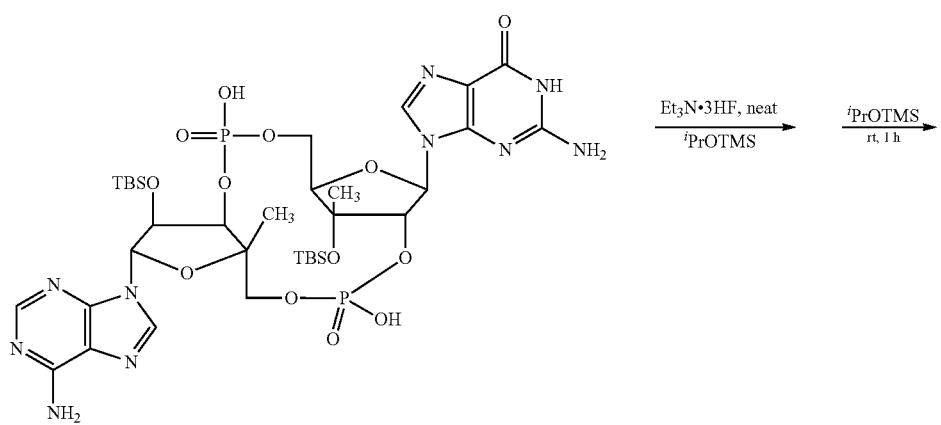
5y

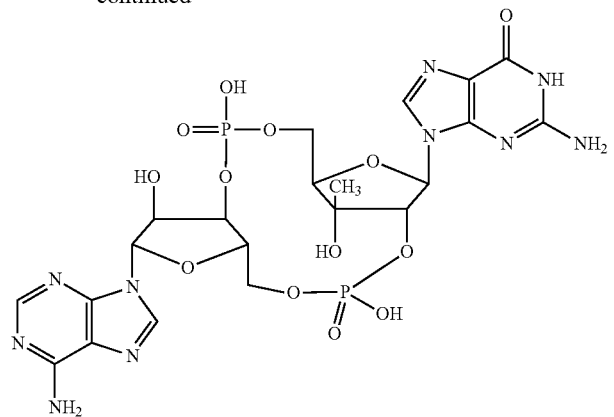
Compound 3, ammonium salt
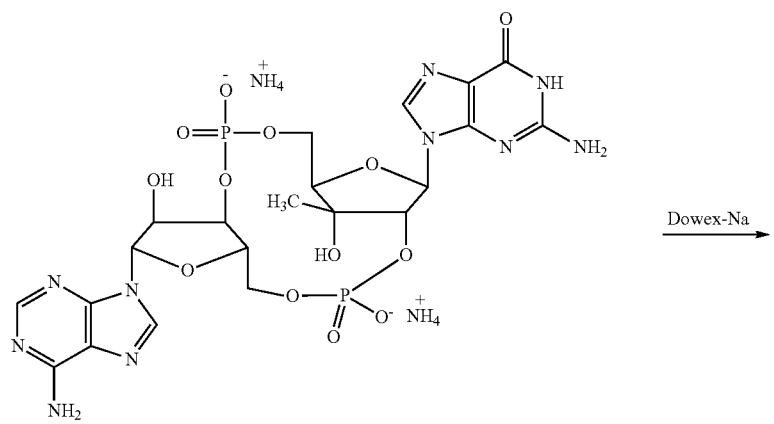
Compound 3, ammonium salt → Dowex-Na
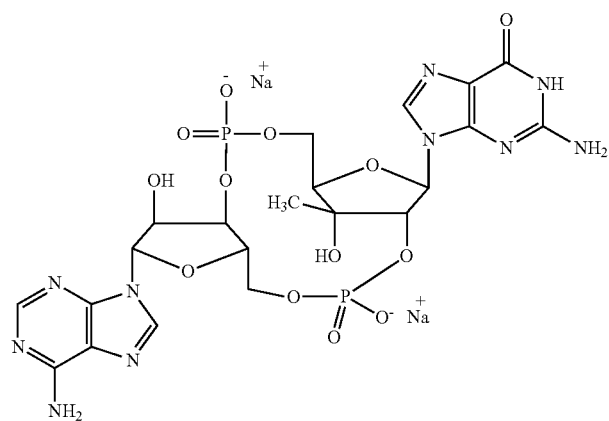
Compound 3, sodium salt

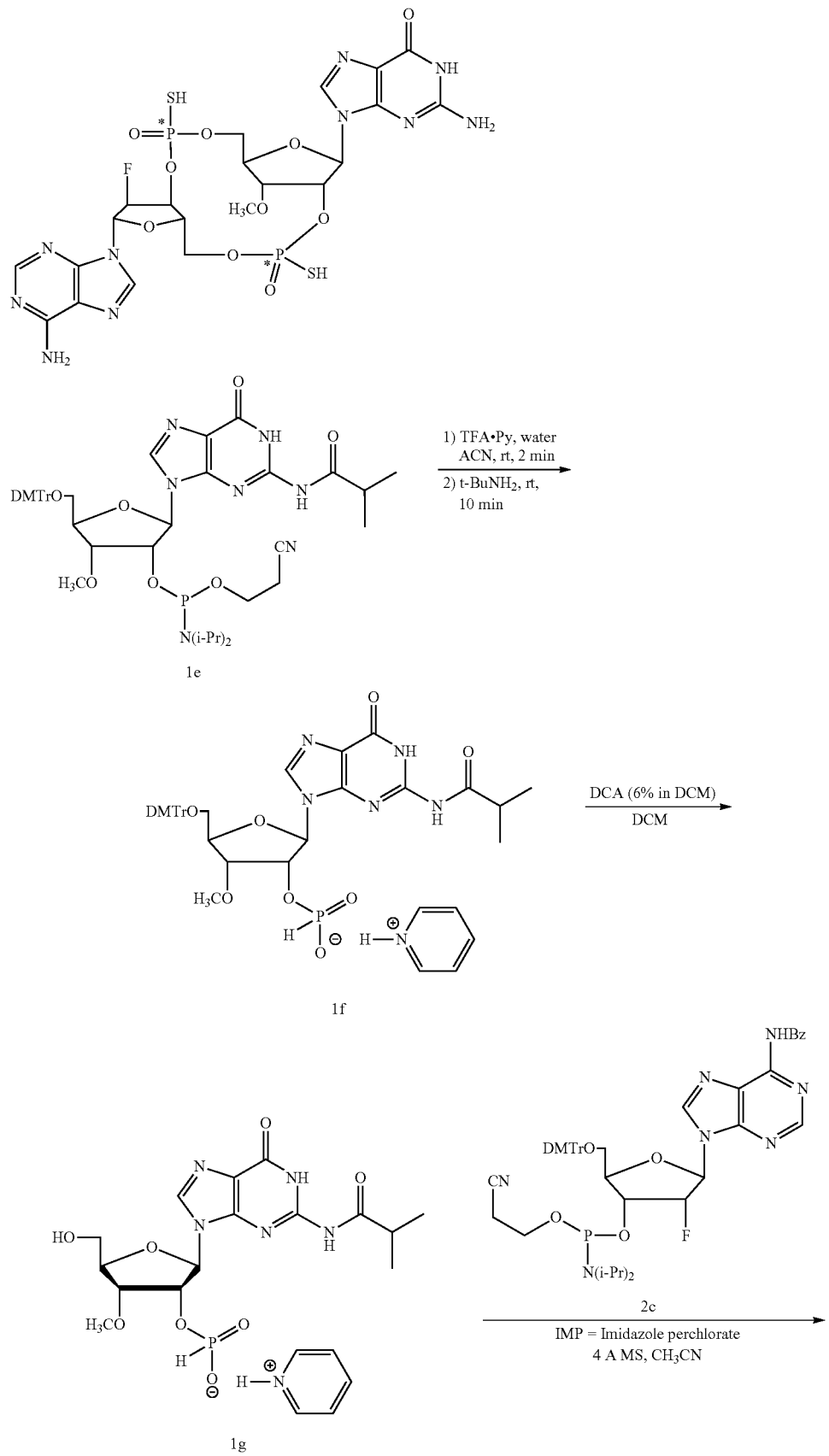
Cpd 6

-continued
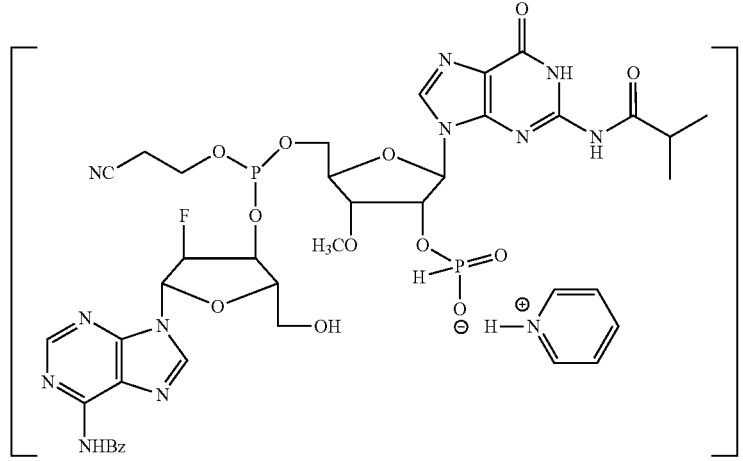
2d
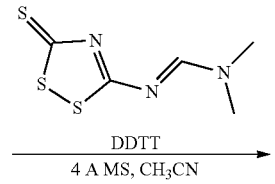
DDTT
4 Å MS, CH₃CN
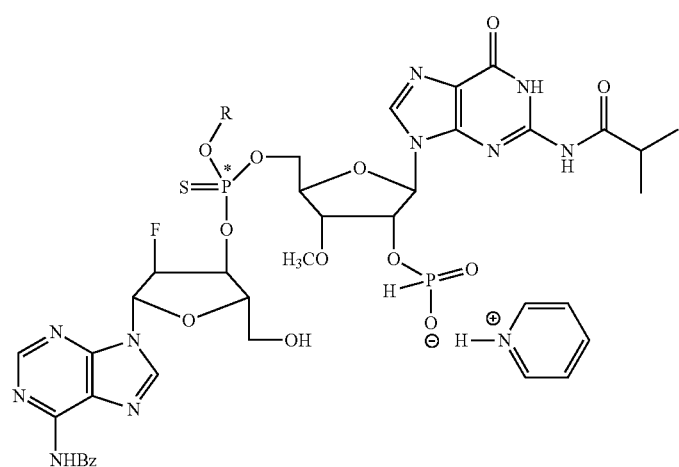
6f: R = CH₂CH₂CN
6g: R = OH
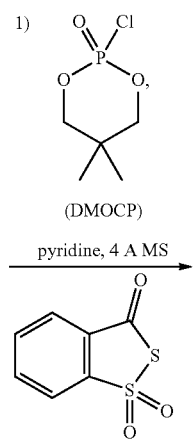
1) (DMOCP)
pyridine, 4 Å MS
Beaucage reagent
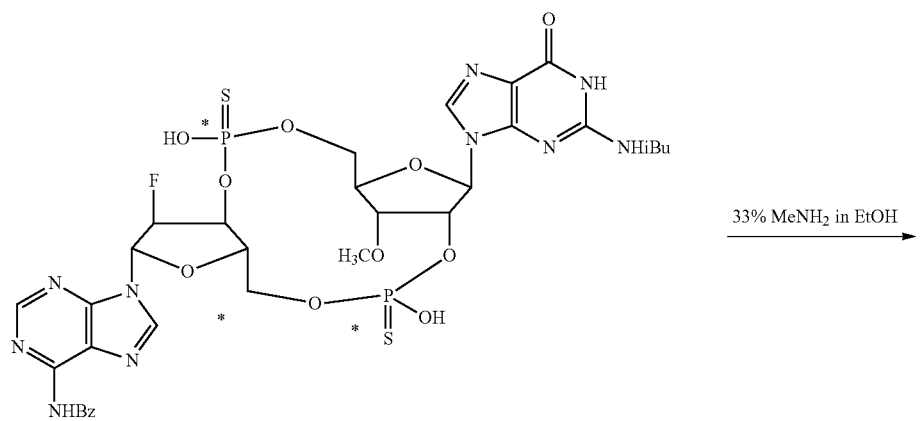
6h: R = CH₂CH₂CN
6i: R = OH
33% MeNH₂ in EtOH -continued
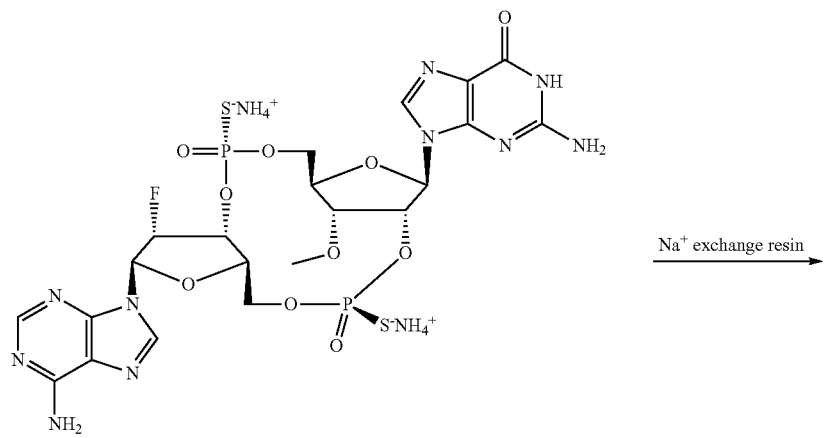
Compound 6a, ammonium salt
Na+ exchange resin →
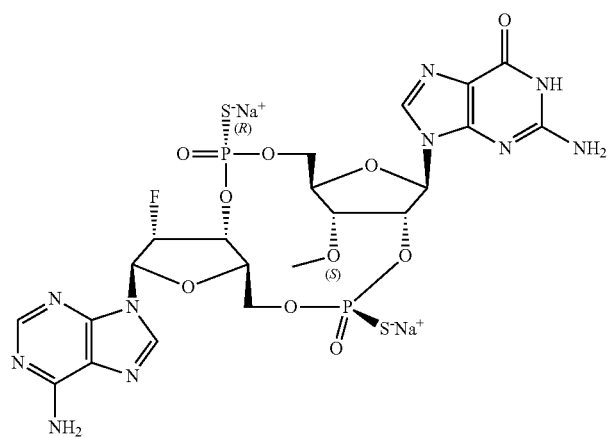
Compound 6a, sodium salt
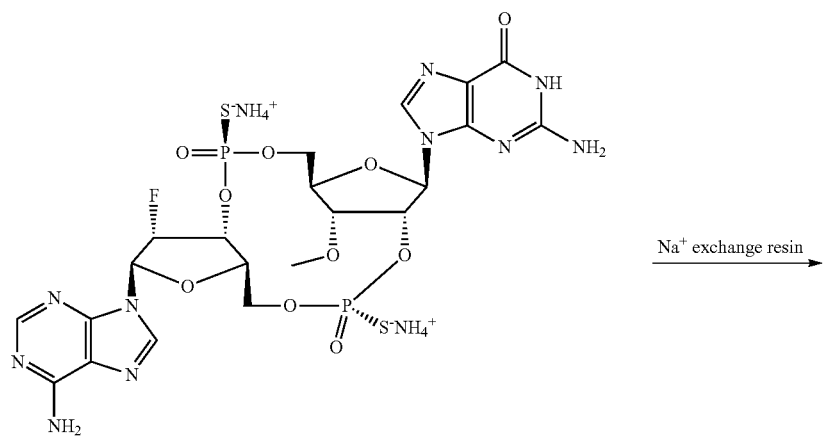
Compound 6b, ammonium salt
Na+ exchange resin →

-continued
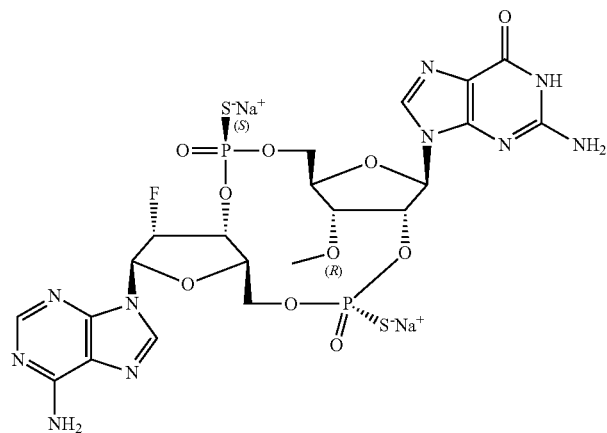
Compound 6b, sodium salt
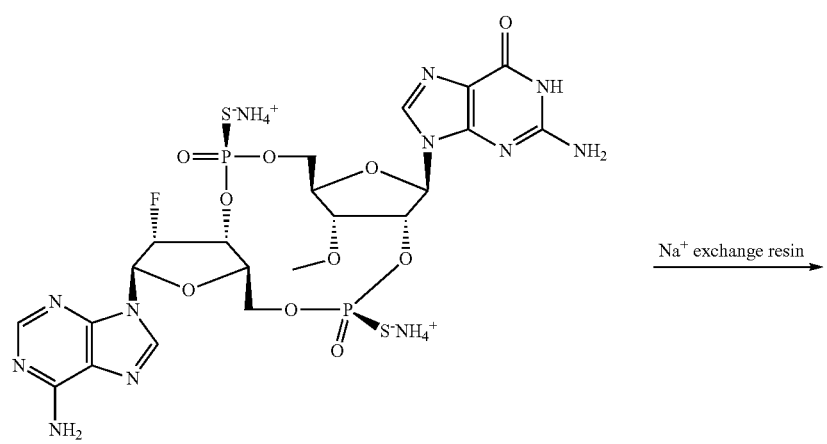
Compound 6c, ammonium salt
$\xrightarrow{\text{Na}^+ \text{ exchange resin}}$
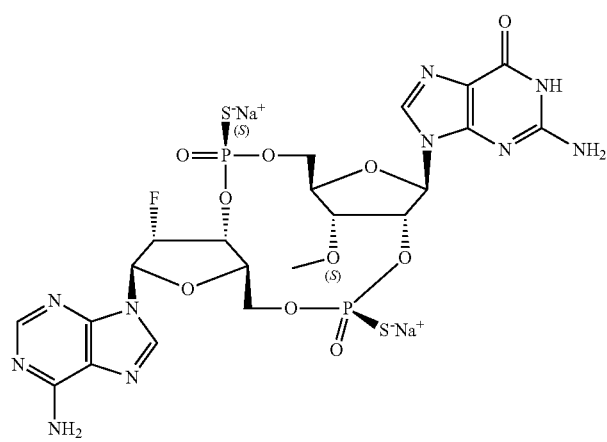
Compound 6c, sodium salt

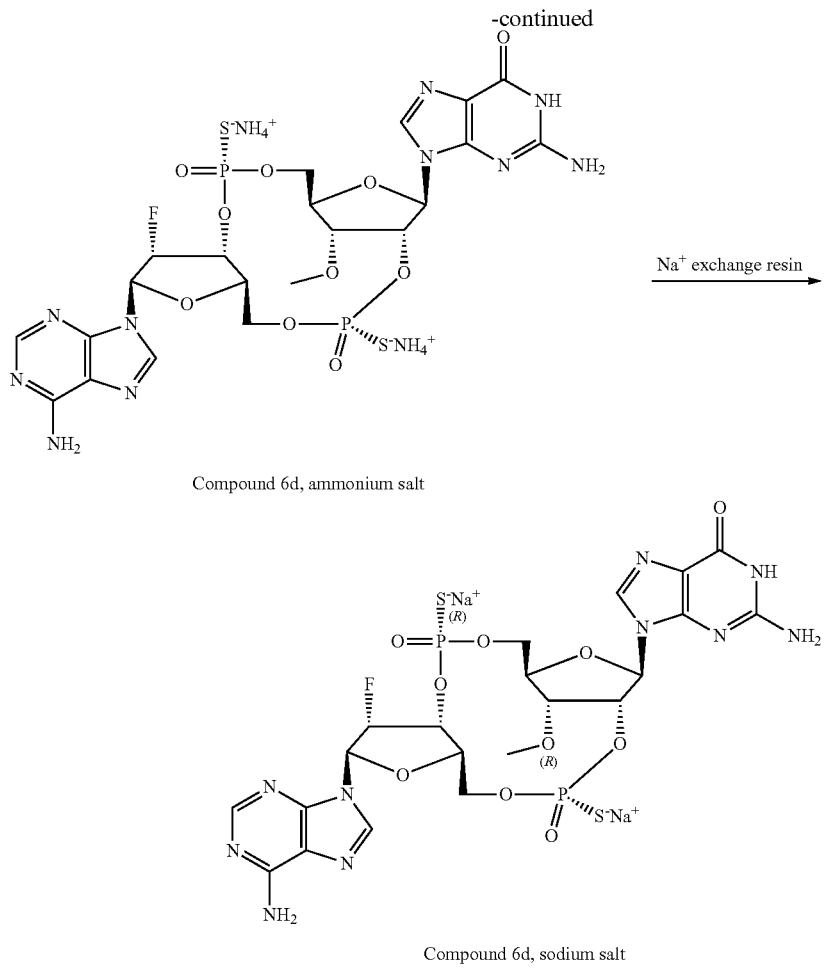

Compound 6d, ammonium salt

Compound 6d, sodium salt

Step 1: Preparation of 1f

To a solution of compound 1e (4.6 g, 5.288 mmol) and water (190.520 mg, 10.575 mmol) in acetonitrile (20 mL) was added pyridinium trifluoroacetate (1.225 g, 6.345 mmol) at 15° C. After 0.5 h, t-butylamine (20 mL) was added. The mixture was concentrated for 2 h to afford the crude product 1f as a white solid (3.96 g, crude). The crude product was used directly for the next step.

Step 2: Preparation of 1g

To a solution of compound 1f (3.359 g, 4.578 mmol) and water (824.688 mg, 45.777 mmol) in $CH_2Cl_2$ (40 mL) was added dichloroacetic acid (40 mL, 6% in $CH_2Cl_2$) at 15° C. After 1 h, pyridine (724.192 mg, 9.155 mmol) was added. The mixture was concentrated and the residue was purified by flash chromatography ($CH_2Cl_2$:MeOH=5:1, Rf=0.5) to afford crude product 1g (1.5 g) as a white solid.

Step 3: Preparation of Compounds 6f+6g

A solution of compound 1g (1.959 g, 1.352 mmol) and 4 Å MS (3 g) in dry $CH_3CN$ (40 mL) was stirred at 15° C. under nitrogen for 10 min. 1H-imidazole perchlorate (6.683 g, 39.182 mmol) was added. After 10 min, compound 2c (2.059 g, 2.351 mmol) in $CH_3CN$ (20 mL) was added. The mixture was stirred at rt for 1 h. (E)-N, N-dimethyl-N'-(3-thioxo-3H-1,2,4-dithiazol-5-yl)formimidamide (DDTT, 5.176 g, 25.211 mmol) was added. The final mixture was stirred at 15° C. for 1 h. The mixture was filtered and the filtrate was concentrated. The residue was purified by reverse phase preparative HPLC (Column: Phenomenex Kinetex XB-C18 150 mm×30 mm, 5 am; Condition: water (10 mM $NH_4HCO_3$)-ACN; Begin B: 20; End B: 50; Flow-Rate (mL/min): 25) to afford a mixture of compounds 6f+6g (260 mg) as a white solid. ESI-MS: m/z=937.1.

Step 4: Preparation of 6h

To a solution of a mixture of compounds 6f+6g (260 mg, 0.278 mmol) and molecular sieve (0.3 g) in pyridine (30 mL) was added DMOCP (153.836 mg, 0.834 mmol) at 16° C. The mixture was stirred at 16° C. for 1 h. Water (50.055 mg, 2.778 mmol) and Beaucage reagent (278.173 mg, 1.389 mmol) was added and stirred at rt for 1.5 h. The mixture was filtered and the filtrate was concentrated. The residue was purified by reverse phase preparative HPLC (Column: Phenomenex Synergi C18 250×21.2 mm 4 μm; Condition: water (10 mM $NH_4HCO_3$)-ACN; Begin B: 10; End B: 40; Flow- Rate (ml/min): 25) to afford a compounds 6h+6i as a mixture of isomers (150 mg) (41.45% of 6i) as a white solid. ESI-MS: m/z=950.2.

Step 5: Preparation of Compounds 6a, 6b, 6c and 6d as Ammonium Salts

A solution of compounds 6h+6i in a solution of $MeNH_2$ in EtOH (33%, 15 mL) was stirred at 15° C. for 2 h. The mixture was concentrated and the residue was diluted with water (3 mL) and purified by reverse phase preparative HPLC (Column: Agela Durashell C18 150×25 5 μm; Condition: water (0.05% ammonia hydroxide v/v)-ACN; Begin B: 0; End B: 20; FlowRate (ml/min): 35) to afford 6a (20.9 mg) as a white solid; 6b (23.0 mg) as a white solid; 6c (13.9 mg) as a white solid; and 6d (9.9 mg) as a white solid.

Compound 6a:
$^1H$ NMR (400 MHz, $D_2O$) 8.36 (s, 1H), 8.11 (s, 1H), 7.83 (s, 1H), 6.34 (d, J=14.8 Hz, 1H), 5.81-5.79 (m, 1H), 5.78-5.64 (m, 1H), 5.61-5.57 (m, 1H), 5.10-5.03 (m, 1H), 4.45-4.44 (m, 2H), 4.41-4.38 (m, 1H), 4.11-4.10 (m, 3H), 4.02-3.99 (m, 1H), 3.46 (s, 3H); $^{19}F$ NMR (376 MHz, $D_2O$) −202.08 (s, 1F); $^{31}P$ NMR (162 MHz, $D_2O$) 54.07 (s, 1P), 52.51 (s, 1P).

Compound 6b:
$^1H$ NMR (400 MHz, $D_2O$) 8.27 (s, 1H), 7.78 (s, 1H), 6.36 (d, J=14.8 Hz, 1H), 5.80-5.75 (m, 2H), 5.39-5.26 (m, 1H), 5.17-5.12 (m, 1H), 4.44-4.30 (m, 4H), 4.07 (d, J=3.6 Hz, 1H), 4.00-3.93 (m, 2H), 3.46 (s, 3H); $^{19}F$ NMR (376 MHz, $D_2O$) −201.87 (s, 1F); $^{31}P$ NMR (162 MHz, $D_2O$) 56.04 (s, 1P).

Compound 6c:
$^1H$ NMR (400 MHz, $D_2O$) 8.25 (s, 1H), 8.01 (s, 1H), 7.72 (s, 1H), 6.28 (d, J=15.6 Hz, 1H), 5.72-5.69 (m, 1H), 5.56 (br s, 1H), 4.95-4.88 (m, 1H), 4.46 (br s, 1H), 4.38-4.35 (m, 2H), 4.09 (s, 3H), 3.88-3.86 (m, 1H), 3.44 (s, 3H); $^{31}P$ NMR (162 MHz, $D_2O$) 52.06 (s, 1P), 51.37 (s, 1P).

Compound 6d:
$^1H$ NMR (400 MHz, $D_2O$) 8.27-8.23 (m, 2H), 7.80 (s, 1H), 6.36 (d, J=16.4 Hz, 1H), 5.76 (br s, 2H), 5.37-5.25 (m, 2H), 4.47-4.36 (m, 4H), 4.10-4.05 (m, 2H), 3.92 (br s, 1H), 3.46 (s, 3H).

Step 6: Preparation of Compound 6a Sodium Salt

A 10 mL volume of Dowex 50W×8, 200-400 (H form) was added to a beaker (for 20.9 mg white solid) and washed with DI $H_2O$ (2×). Then to the resin was added 15% $H_2SO_4$ in DI $H_2O$ (50 mL), the mixture was stirred for 15 min, and decanted (1×). The resin was transferred to a column with 15% $H_2SO_4$ in DI $H_2O$ and washed with 15% $H_2SO_4$ (at least 4 CV), and then with DI $H_2O$ until it was neutral. The resin was transferred back into the beaker, and 15% NaOH in DI $H_2O$ solution (50 mL) was added, and the mixture was stirred for 15 min, and decanted (1×). The resin was transferred to the column and washed with 15% NaOH in DI $H_2O$ (at least 4 CV), and then with $H_2O$ until it was neutral (at least 4 CV). Compound 6a ammonium salt (20.9 mg, 0.022 mmol) was dissolved in DI water (3 mL), added to the top of the column, and eluted with DI water. Compound 6a was eluted out in early fractions as detected by TLC (UV). The product was lyophilized to give compound 6a sodium salt (10.7 mg) as a white solid. ESI-MS: m/z=722.8; $^1H$ NMR (400 MHz, $D_2O$) 8.29 (s, 1H), 8.06 (s, 1H), 7.83 (s, 1H), 6.30 (d, J=14.8 Hz, 1H), 5.79 (d, J=8.8 Hz, 1H), 5.75-5.61 (m, 1H), 5.59-5.56 (m, 1H), 5.07-5.01 (m, 1H), 4.45-4.37 (m, 3H), 4.11-4.10 (m, 3H), 3.99 (d, J=11.6 Hz, 1H), 3.45 (s, 3H); $^{31}P$ NMR (162 MHz, $D_2O$) 54.23 (s, 1P), 52.76 (s, 1P); $^{19}F$ NMR (376 MHz, $D_2O$) −202.00 (s, 1F).

Preparation of Compound 6b Sodium Salt

A 10 mL volume of Dowex 50W×8, 200-400 (H form) was added to a beaker (for 23.0 mg of white solid) and washed with DI $H_2O$ (2×). Then to the resin was added 15% $H_2SO_4$ in DI $H_2O$ (50 mL), the mixture was stirred for 15 min, and decanted (1×). The resin was transferred to a column with 15% $H_2SO_4$ in DI $H_2O$ and washed with 15% $H_2SO_4$ (at least 4 CV), and then with DI $H_2O$ until it was neutral. The resin was transferred back into the beaker, and 15% NaOH in DI $H_2O$ solution (50 mL) was added, and the mixture was stirred for 15 min, and decanted (1×). The resin was transferred to the column and washed with 15% NaOH in DI $H_2O$ (at least 4 CV), and then with $H_2O$ until it was neutral (at least 4 CV). Compound 6b ammonium salt (23.0 mg, 0.030 mmol) was dissolved in DI water (3 mL), added to the top of the column, and eluted with DI water. Compound 6b was eluted in early fractions as detected by TLC (UV). The product was lyophilized to give compound 6b sodium salt (12.7 mg) as a white solid. ESI-MS: m/z=722.7; $^1H$ NMR (400 MHz, $D_2O$) 8.39 (s, 1H), 8.09 (s, 1H), 7.71 (s, 1H), 6.31 (d, J=14.0 Hz, 1H), 5.79-5.73 (m, 2H), 5.41-5.27 (m, 1H), 5.24-5.14 (m, 1H), 4.43-4.38 (m, 3H), 4.32-4.30 (m, 1H), 4.08 (d, J=4.0 Hz, 1H), 4.00-3.97 (m, 2H), 3.45 (s, 3H); $^{31}P$ NMR (162 MHz, $D_2O$) 55.88 (s, 1P), 53.45 (s, 1P); $^{19}F$ NMR (376 MHz, $D_2O$) −201.97 (s, 1F).

Preparation of 6c Sodium Salt

A 10 ml volume of Dowex 50W×8, 200-400 (H form) was added to a beaker (for 13.9 mg of white solid) and washed with DI $H_2O$ (2×). Then to the resin was added 15% $H_2SO_4$ in DI $H_2O$ (50 mL), the mixture was stirred for 15 min, and decanted (1×). The resin was transferred to a column with 15% $H_2SO_4$ in DI $H_2O$ and washed with 15% $H_2SO_4$ (at least 4 CV), and then with DI $H_2O$ until it was neutral. The resin was transferred back into the beaker, and 15% NaOH in DI $H_2O$ solution (50 mL) was added, and the mixture was stirred for 15 min, and decanted (1×). The resin was transferred to the column and washed with 15% NaOH in DI $H_2O$ (at least 4 CV), and then with $H_2O$ until it was neutral (at least 4 CV). Compound 6c ammonium salt (13.9 mg, 0.018 mmol) was dissolved in DI water (3 mL), added to the top of the column, and eluted with DI water. 6c was eluted out in early fractions as detected by TLC (UV). The product was lyophilized to give compound 6c sodium salt (4.8 mg) as a white solid. ESI-MS: m/z=722.8; $^1H$ NMR (400 MHz, $D_2O$) 8.09 (s, 1H), 8.02 (s, 1H), 7.84 (s, 1H), 6.30 (d, J=15.2 Hz, 1H), 5.80-5.64 (m, 2H), 5.47-5.41 (m, 1H), 4.99-4.93 (m, 1H), 4.47-4.41 (m, 3H), 4.24 (d, J=4.0 Hz, 1H), 4.10 (br s, 2H), 4.05-4.02 (m, 1H), 3.43 (s, 3H);
$^{31}P$ NMR (162 MHz, $D_2O$) 52.46 (s, 1P), 52.00 (s, 1P); $^{19}F$ NMR (376 MHz, $D_2O$) −201.91 (s, 1F).

Preparation of 6d Sodium Salt

A 10 ml volume of Dowex 50W×8, 200-400 (H form) was added to a beaker (for 9.9 mg of white solid) and washed with DI $H_2O$ (2×). Then to the resin was added 15% $H_2SO_4$ in DI $H_2O$ (50 mL), the mixture was stirred for 15 min, and decanted (1×). The resin was transferred to a column with 15% $H_2SO_4$ in DI $H_2O$ and washed with 15% $H_2SO_4$ (at least 4 CV), and then with DI $H_2O$ until it was neutral. The resin was transferred back into the beaker, and 15% NaOH in DI H$_2$O solution (50 mL) was added, and the mixture was stirred for 15 min, and decanted (1×). The resin was transferred to the column and washed with 15% NaOH in DI H$_2$O (at least 4 CV), and then with H$_2$O until it was neutral (at least 4 CV). Compound 6d ammonium salt (9.9 mg, 0.013 mmol) was dissolved in DI water (3 mL), added to the top of the column, and eluted with DI water. Compound 6d was eluted out in early fractions as detected by TLC (UV). The product was lyophilized to give compound 6d sodium salt (1.0 mg) as a white solid. ESI-MS: m/z=722.8; $^1$H NMR (400 MHz, D$_2$O) 8.14 (s, 1H), 8.12 (s, 1H), 7.71 (s, 1H), 6.33 (d, J=13.6 Hz, 1H), 5.76 (d, J=8.4 Hz, 1H), 5.65-5.62 (m, 1H), 5.47-5.34 (m, 1H), 5.21-5.13 (m, 1H), 4.46-4.43 (m, 3H), 4.32-4.29 (m, 1H), 4.18 (d, J=3.6 Hz, 1H), 4.02-3.99 (m, 2H), 3.43 (s, 3H); $^{31}$P NMR (162 MHz, D$_2$O) 55.68 (s, 1P), 51.77 (s, 1P); $^{19}$F NMR (376 MHz, D$_2$O) −202.20 (s, 1F).

BIOLOGICAL EXAMPLES

In Vitro Assays

Example 1

STING SPA Binding Assay

The human STING SPA binding assay measures displacement of tritium labeled 2',3'cGAMP (cyclic (guanosine-(2'→5')-monophosphate-adenosine-(3'→5')-monophosphate) to biotinylated STING protein. A soluble version of recombinant STING was expressed in *E. coli* that lacks the four transmembrane domains and contains residues 139-379 of Q86WV6 with an R at position 232 (H232R). Based on the allele frequency of 58% of the population, H232R is considered to be a wild type (Yi, et. al., "Single Nucleotide Polymorphisms of Human STING can affect innate immune response to cyclic dinucleotides" *PLOS ONE*. 2013, 8(10), e77846). The STING construct has an N-terminal HIS tag, followed by a TEV protease cleavage site and an AVI tag to allow directed biotinylation by BirA biotin ligase (Beckett et al., A minimal peptide substrate in biotin holoenzyme synthetase-*catalyzed biotinylation*. (1999) *Protein Science* 8, 921-929). The HIS tag is cleaved after purification and prior to biotinylation.

The assay was run in 1536-well plates in a total volume of 8 µL per well by adding 8 nM [$^3$H]-2'3'-cGAMP and 40 nM biotin-STING protein in assay buffer [25 mM HEPES (Corning 25-060-C1) pH 7.5, 150 mM NaCl (Sigma S5150), 0.5 mg/mL BSA (Gibco 15260-037), 0.001% Tween-20 (Sigma P7949), molecular grade water (Corning 46-000-CM)]. Test compounds (80 nL) were added with an acoustic dispenser (EDC Biosystems) in 100% DMSO for a final assay concentration of 1% DMSO. Plates were centrifuged for 1 min and incubated for 60 min at room temperature. Finally, (2 µL) polystyrene streptavidin SPA beads (PerkinElmer RPNQ0306) were added and plates were sealed and centrifuged for 1 min at room temperature. Plates were dark adapted for 2 h and read on a ViewLux (Perkin Elmer) for 12 min per plate. A saturation binding curve for [$^3$H]-2'3'-cGAMP showed a K$_D$ of 3.6±0.3 nM for binding to STING, comparable to reported values for the natural ligand (Zhang et al., Cyclic GMP-AMP containing mixed phosphodiester linkages is an endogenous high-affinity ligand for STING. Other natural ligands including cyclic-di-GMP also returned values in this assay within the expected range. Reference compound is cGAMP and results are reported as percent inhibition and IC$_{50}$ values. Binding to mouse STING used a construct similar to the one described above containing residues 138-378 of Q3TBT3.

Full Length Human STING Binding Assay

Human STING from residues 1-379 of Q86WV6 with an R at position 232 (H232R) with an N-terminal 6HIS tag followed by a FLAG tag, a TEV protease cleavage site and an AVI tag for biotinylation was recombinantly expressed in HEK293-EXPI cells. Purified membranes were prepared from these cells and STING expression was confirmed and quantified by immunoblot. STING containing membranes were combined with test compound in a Greiner 384-well assay plate and incubated at room temperature for one hour in the same assay buffer used for the STING SPA binding assay. Next, [$^3$H]-2'3'-cGAMP was added and plates were incubated for 30 min at room temperature. Reactions were transferred to a prewashed Pall 5073 filter plate and each well was washed 3 times with 50 µL assay buffer. Filter plates were dried at 50° C. for 1 h. To each well, 10 µL of Microscint scintillation fluid was added and plates were sealed and read on a TopCount (Perkin Elmer) for 1 min per well.

STING SPR Binding Assay

Compounds were analyzed on an S200 biacore SPR instrument (GE Healthcare). *E. coli* produced truncated STING protein was immobilized on a series S streptavidin chip via biotin capture (GE Healthcare #BR100531) with. Compounds were screened at 1:2 dilutions from 100 uM to 0.195 uM in run buffer (10 mM HEPES, pH 7.4, 150 mM NaCl, 0.005% P20, 1 mM TECEP). Steady state affinity and kinetic evaluations were carried out using 1:1 binding model (STING was treated as a dimer). Run parameters were as follows: 60 sec on, 300 sec off for the IFM compounds, cyclic-di-GMP (60 sec on/60 sec off), thiol isomer 1 (60 sec on/300 sec off) and cGAMP (60 sec on/1200 sec off) with a flow rate of 50 µL/min and data collection at 40 Hz at 25° C.

STING Human Cell Reporter Assay

Agonism of the human STING pathway is assessed in THP1-ISG cells (Invivogen, cat #thp-isg) derived from human THP1 monocyte cell line by stable integration of an interferon regulatory factor (IRF)-inducible SEAP reporter construct. THP1-Blue ISG cells express a secreted embryonic alkaline phosphatase (SEAP) reporter gene under the control of an ISG54 minimal promoter in conjunction with five interferon (IFN)-stimulated response elements. As a result, THP1-Blue ISG cells allow the monitoring of IRF activation by determining the activity of SEAP. The levels of IRF-induced SEAP in the cell culture supernatant are readily assessed with alkaline phosphatase detection medium, a SEAP detection reagent. These cells are resistant to Zeocin. 2'3'cGAMP was used as a positive control in this assay. To run the assay, 60,000 cells were dispensed in 30 µL/well of a white, opaque bottom tissue culture treated 384-well plate.

Test compounds were added in a volume of 10 µL (1% DMSO final concentration). Compounds are initially prepared in 100% DMSO, spotted on an intermediate dilution plate and then diluted in media prior to transfer. The assay was incubated for 24 h at 37° C., 5% CO$_2$ then plates were centrifuged at 1200 rpm (120×g) for 5 min. After final incubation, 90 µL of alkaline phosphatase detection medium-substrate was added to each well of a new 384-well clear plate and 10 µL of the cell supernatant was transferred from the assay plate to the new alkaline phosphatase detection medium-plate using a Biomek FX and mixed 4 times. Plates were incubated at RT for 20 min then absorbance at 655 nm was determined on the Tecan Safire2.

STING Mouse Cell Reporter Assay

Agonism of the mouse STING pathway is assessed in RAW Lucia cells (Invivogen, cat # rawl-isg) derived from mouse RAW-264.7 macrophage cell line by stable integration of an interferon-inducible Lucia luciferase reporter construct. RAW Lucia cells express a secreted luciferase reporter gene under the control of an ISG54 minimal promoter in conjunction with five interferon (IFN)-stimulated response elements. As a result, RAW Lucia cells allow the monitoring of IRF activation by determining the activity of luciferase. The levels of IRF-induced luciferase in the cell culture supernatant are readily assessed with QUANTI-Luc™, a luciferase detection reagent. These cells are resistant to Zeocin. 2'3'cGAMP is used as a positive control in this assay. To run the assay, 100,000 cells were dispensed in 90 µL/well of a clear, flat bottom tissue culture treated 96-well plate. Test compounds were added in a volume of 10 µL. The assay was incubated for 24 and 48 hours at 37° C., 5% $CO_2$. After incubation, 20 µL of the cell supernatant from the assay plate was transferred to a new 96-well white plate and 50 uL of QUANTI-Luc substrate was added. The plate was incubated, shaking, at RT for 5 minutes then luminescence was read on an EnVision 2104 with 0.1 s integration time.

Human Interferon-β Induction Assay

THP1-Blue ISG cells are used to measure the secretion of IFN-β into the culture supernatant following STING pathway activation. To run the assay, anti-IFN-β capture antibodies were coated on 96 well MultiArray plates (Mesoscale Discovery). After a one hour incubation, plates were washed and 50 µL supernatant from the STING human cell reporter assay plates or IFN-β standards were mixed with 20 µL Sulfotag-conjugated detection antibody in the coated plates. Plates were incubated, shaking for 2 h, washed, and read buffer was applied. Electrochemiluminescence was measured on the SectorImager.

STING Cell Signaling Pathway Assessment

Agonism of the STING pathway was measured in THP1 BLUE ISG cells by western blot of phospho-STING(S366), phospho-TBK1(S172) and phospho-IRF3 (S396). Briefly, 5 million cells in 90 µL nucleofection buffer were mixed with 10 µL test compounds. These mixtures were electroporated using program V-001 on an Amaxa Nucleofector (Lonza). Cells were transferred into 12 well plates with fresh media and allowed to recover for one hour at 37° C., 5% $CO_2$. Cells were then washed in cold HBSS and lysed in RIPA buffer. Samples were total protein normalized and either diluted in ProteinSimple sample buffer or LDS loading buffer. Samples were heat denatured at 95° C. for 5 min, then PeggySue (ProteinSimple) was used to measure phospho- and total STING and IRF3 while the NuPAGE (Invitrogen) system was used to measure TBK1. Data was analyzed using Compass or Licor Odyssey software, respectively.

STING In Vivo Activity

For all studies, female Balb/c mice were obtained from Charles River Labs (Wilmington, Mass.) and used when they were 6-8 weeks of age and weighed approximately 20 g. All animals were allowed to acclimate and recover from any shipping-related stress for a minimum of 5 days prior to experimental use. Reverse osmosis chlorinated water and irradiated food (Laboratory Autoclavable Rodent Diet 5010, Lab Diet) were provided ad libitum, and the animals were maintained on a 12 h light and dark cycle. Cages and bedding were autoclaved before use and changed weekly. All experiments were carried out in accordance with The Guide for the Care and Use of Laboratory Animals and were approved by the Institutional Animal Care and Use Committee of Janssen R & D, Spring House, Pa. Each experimental group contained 8 mice. In vivo efficacy in a mouse CT26 tumor model was determined by implanting 500,000 CT26 colon carcinoma tumor cells subcutaneously into Balb/c mice and allowing tumors to establish to 100-300 $mm^3$. Compounds were injected intratumorally formulated in phosphate buffered saline in a volume of 0.1 mL per injection. Mice were administered 0.05 mg every three days for a total of three doses. Efficacy was measured as the percent tumor growth inhibition (TGI) calculated by the reduction in size of the Treated tumor volume (T) over the Control tumor volume (C) according to the following formula: $((C-T)/(C))*100$ when all control animals were still on study. Cures were defined as the number of animals with no measurable tumor detected 10 tumor volume doubling times (TVDT) after the last dose was administered.

The resultant data are presented in Table 3.

TABLE 3

| Cpd No. | hSTING SPA IC50 (µm) | human cell reporter EC50 (µm) | SPR human STING KD (µm) | mSTING SPA IC50 (µm) | human IFN-β (ranking value) | In vivo activity (% TGI) | In vivo activity (cures) |
|---|---|---|---|---|---|---|---|
| 1 | 54.5 | 1.81 | ND | ND | ND | ND | ND |
| 4 | <0.01 | 0.019 | ND | <0.002 | 821 | 83.6 | 1 |
| 5 | <0.01 | 0.21 | <0.01 | 0.016 | 1024 | 90.8 | 1 |
| 6a | <0.01 | 0.053 | 0.006 | ND | 2427 | 94.8 | 6 |
| 6b | <0.01 | 0.107 | 0.0017 | <0.01 | 904 | 95 | 7 |
| 6c | <0.01 | 0.06 | 0.0017 | <0.01 | 4266 | 94.1 | 8 |
| 6d | — | ND | ND | ND | 3039 | ND | ND |

ND—not done, human IFN-β ranking value determined by Ranking value determined by total cumulative IFN-β induction over the dose range tested (0.78 to 50 µM) in THP-1 Blue cells.

Biological Example 2

STING Primary Human PBMC Cytokine Induction Assay

Agonism of the human STING pathway is assessed in primary human peripheral blood mononuclear cells (PBMC) derived from human whole blood. 1 pint (approximately 420 ml) of fresh donor blood (AllCells Inc., Alameda, Calif.) is layered over Lymphocyte Separation Medium (1.077-1.080 g/ml, Corning, Manassas, Va.), then centrifuged at 500 g for 20 min at RT without applying break. The PBMC collected at the interface between serum and Lymphocyte Separation Medium are harvested, washed, then counted. PBMC are composed of subtypes of lymphocytes and monocytes, such as B cells, T cells, etc., and these subtypes have been characterized in the literature to express different levels of the STING protein. In response to STING agonists, such as 2'3'-cGAMP, these cells become activated and are induced to express a variety of proinflammatory and antiviral cytokines. Also, upon stimulation with STING agonists, these cells upregulate activation markers. The levels of cytokine induction can be measured by a variety of methods including ELISA, Luminex and MSD. The levels of activation marker upregulation can be measured by flow cytometry.

To run the assay, 1,000,000 cells were dispensed into 225 µL/well of flat-bottom, tissue culture treated, 96-well plates. Test compounds were added in a volume of 25 µL at 10× concentration. Some compounds were solubilized in 100% DMSO and the final concentration of DMSO in the cultures receiving these compounds was 1%. The assay was incubated for 48 h at 37° C., 5% $CO_2$. 200 µl of supernatants were harvested without disturbing cells on the bottom of the plate, then frozen at −20° C. until time of Luminex measurement. Luminex assays were performed using G-CSF, IFNα2, IFNγ, IL-1b, IL-6, IL-10, IL-12 (p40), IL-12 (p70), TNFa from MILLIPLEX MAP Human Cytokine/Chemokine Magnetic Bead Panel—Immunology Multiplex Assay kit and IFNβ1 analyte from MILLIPLEX MAP Human Cytokine/Chemokine Magnetic Bead Panel IV kit (EMD Millipore, Billerica, Mass.), following the manufacturer's protocol. Cytokine induction was measured using a Luminex FlexMAP 3D® instrument (Luminex Corporation, Radnor, Pa.). Analysis of collected Luminex data was performed using MILLIPLEX Analyst software (EMD Millipore).

Suppression of HBV Virus in PHH Cells Using Conditioned Media from STING Activated Primary Human PBMC Primary human hepatocytes can be infected with hepatitis B virus and during an established infection, will produce viral proteins such as HBsAg and HBeAg that can be detected by ELISA. Therapeutic treatment with compounds such as entecavir can suppress HBV reproduction, which can be measured by decreased viral protein production. (# of cells) $4×10^5$ cells/well primary human hepatocytes (BioReclamation, Westbury, N.Y.) were dispensed into 500 µL/well of flat-bottom, tissue culture treated, 24-well plates. 24 h later, cells were infected with 30-75 moi of HBV. On the next day, the PHH were washed 3× and fresh maintenance media was added to the cells. Concurrently, PBMC were isolated as described previously. To stimulate the PBMC, 10,000,000 cells were dispensed into 400 µL/well of flat-bottom, tissue culture treated, 24-well plates. Test compounds were added in a volume of 100 µL, then the cultures were incubated for 48 h at 37° C., 5% $CO_2$. Supernatants were harvested. Cells were measured for activation marker upregulation using flow cytometery. Briefly, cells were stained with fluorescently labeled antibodies directed to CD56, CD19, CD3, CD8a, CD14, CD69, CD54, CD161, CD4 and CD80. Samples were analyzed on an Attune NxT flow cytometer (Thermo Fisher, Carlsbad, Calif.)

From the stimulated PBMC cultures, a portion of supernatant was reserved for cytokine detection by Luminex, as described previously. The rest of the supernatant was divided in half, and one aliquot was stored at 4° C. for use on $d_8$ of the assay. The other aliquot of supernatant was diluted 1:1 with 2×PHH media, then added to the $d_4$ infected PHH cells. After 96 h, the spent media was changed and supernatant was added at a dilution of 1:1 with 2×PHH media. At this point an interim measurement of HBsAg was performed using an HBsAg ELISA kit (Wantai Bio-pharm, Beijing, China). Following 96 h, the media was collected and HBsAg was measured.

Table 4: Fold Induction of Cytokines in PBMC Cultures Stimulated with CDN Compounds.

Fold induction is calculated by measuring the concentrations of the cytokine induced after 48 h by approximately 20 µM of compound, then dividing by base line levels of cytokine production of cells incubated with PBS. The data is the average of multiple donors over three experiments. nt=not tested.

TABLE 4

| Cpd No. | IL-6 | IL-10 | IFN-γ | IL-1b | IFN-α | TNFa | IL12p40 | IL12p70 | G-CSF | IFN-β |
|---|---|---|---|---|---|---|---|---|---|---|
| 4 | 4.0 | 10.7 | 108.5 | 17.8 | 6.4 | 35.6 | 7.1 | 197.5 | 16.4 | 10.9 |

Table 5: Fold Induction of Cytokines in PBMC Cultures Stimulated with Higher Concentrations of CDN Compounds.

Fold induction is calculated by measuring the concentrations of the cytokine induced after 48 h the indicated concentration of compound, then dividing by base line levels of cytokine production of cells incubated with PBS. The data is the average of multiple donors over three experiments. nt=not tested.

TABLE 5

| Cpd No. | Top Conc (µM) | IL-6 | IL-10 | IFNγ | IL-1β | IFNα2 | TNFα | IL12p40 | IL12p70 | G-CSF | IFNβ1 |
|---|---|---|---|---|---|---|---|---|---|---|---|
| 4 | 40 µM | 392.6 | 13.2 | 1577.7 | 167.6 | 15.7 | 89.3 | 1.0 | 5.8 | 44.1 | 18.6 |

Table 6. Conditioned Media from PBMCs Stimulated with CDN can Suppress Viral Load of HBV Infected PHH Cells.

PBMCs were stimulated with the indicated CDN at 20, 4, 0.8 M for 48 h. Supernatants were mixed with fresh media at a ratio of 1:1, then added to HBV infected PHH cells. HBsAg production was measured 8 days later. The data is an average of two independent donors.

TABLE 6

| Cpd No. | EC50 (µM) |
|---|---|
| 4 | 8.37E−05 |

Table 7. CDN Activate PBMC.

PBMCs were stimulated with 20 µM of CDN for 48 h. Cells were assessed by flow cytometry for upregulation of CD54 on monocytes. The fold increase in Mean Fluoresence Intensity was calculated relative to the levels on resting cells. The data is an average of two independent donors.

TABLE 7

| Cpd No. | MFI |
|---|---|
| 4 | 5.9 |
| 4-2'3'-cGAMP | 4.5 |
| PBS | 1.0 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A method of treating hepatitis B comprising administering to a subject in need thereof a therapeutically effective amount of the compound of Formula (I)

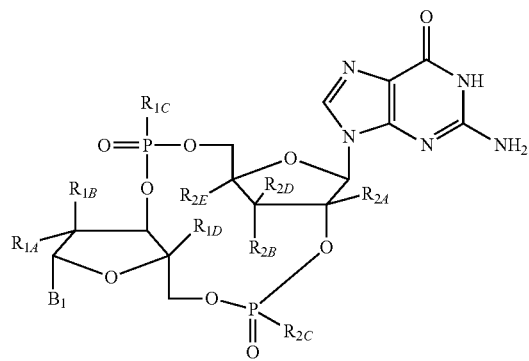

(I)

wherein $R_{1A}$, $R_{2A}$, $R_{1D}$, $R_{2D}$, and $R_{2E}$ are each, independently, hydrogen or methyl; such that one of said $R_{1A}$, $R_{2A}$, $R_{1D}$, $R_{2D}$, and $R_{2E}$ is methyl;

$R_{1B}$ is hydrogen, hydroxy or fluoro; or, $R_{1B}$ is —O—, and $R_{1D}$ is $CH_2$, wherein $R_{1B}$, $R_{1D}$ and the atoms to which they are attached form a 5-membered ring;

$R_{1C}$ is hydroxy, thiol, or $BH_3^-$;

$B_1$ is ring b1 or b2

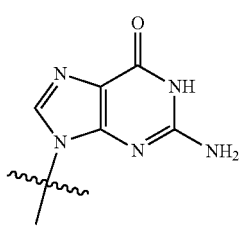

b1

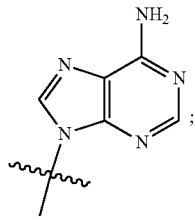

b2

$R_{2B}$ is hydroxy, fluoro or methoxy;

$R_{2C}$ is hydroxy, thiol, or $BH_3^-$;

or an enantiomer, diastereomer, or pharmaceutically acceptable salt form thereof.

2. The method of claim 1, wherein $R_{1B}$ is hydrogen or fluoro.

3. The method of claim 1, wherein $R_{1B}$ is —O—, and $R_{1D}$ is $CH_2$, wherein $R_{1B}$, $R_{1D}$ and the atoms to which they are attached form a 5-membered ring.

4. The method of claim 1, wherein $R_{1C}$ is selected from the group consisting of hydroxy and thiol.

5. The method of claim 1, wherein $R_{1D}$ is hydrogen.

6. The method of claim 1, wherein $B_1$ is ring b2

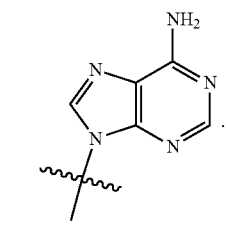

b2

7. The method of claim 1, wherein $R_{2A}$ is hydrogen.

8. The method of claim 1, wherein $R_{2C}$ is selected from the group consisting of hydroxy and thiol.

9. The method of claim 1, wherein $R_{2D}$ is hydrogen.

10. The method of claim 1, wherein:

$R_{1C}$ is selected from the group consisting of hydroxy and thiol; and $B_1$ is ring b2

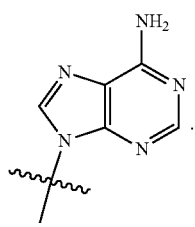

b2

11. The method of claim 1 selected from the group consisting of compounds 1 to 3

101

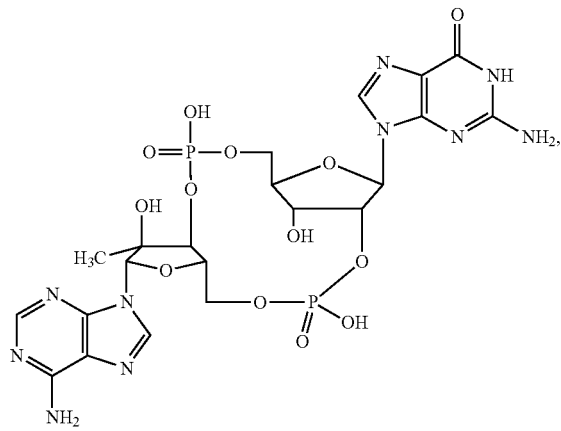

1

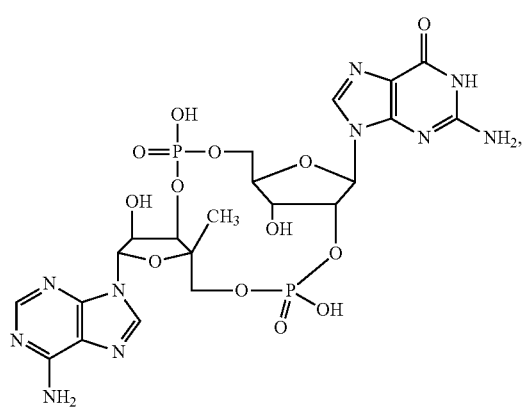

2

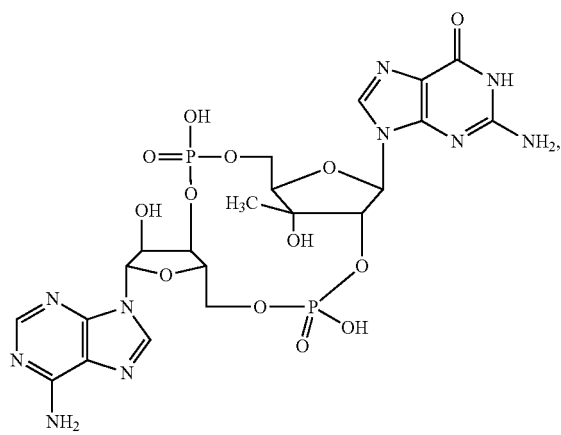

3 or a pharmaceutically acceptable salt form thereof.

12. A method of treating hepatitis B comprising administering to a subject in need thereof a therapeutically effective amount of a pharmaceutical composition comprising a of Formula (I) and at least one of a pharmaceutically acceptable carrier, a pharmaceutically acceptable excipient, and a pharmaceutically acceptable diluent:

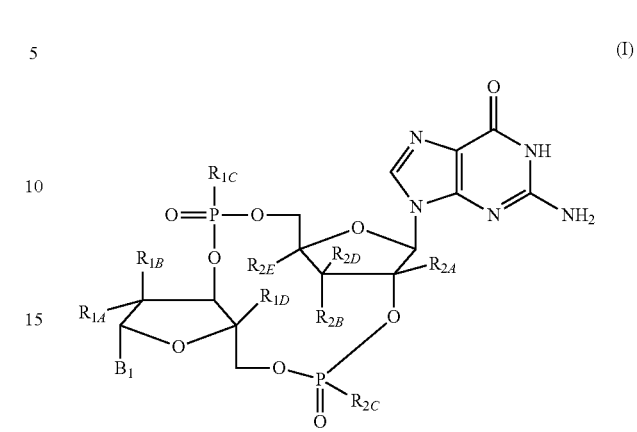

(I)

wherein
$R_{1A}$, $R_{2A}$, $R_{1D}$, $R_{2D}$, and $R_{2E}$ are each, independently, hydrogen or methyl; such that one of said $R_{1A}$, $R_{2A}$, $R_{1D}$, $R_{2D}$, and $R_{2E}$ is methyl;
$R_{1B}$ is hydrogen, hydroxy or fluoro; or, $R_{1B}$ is —O—, and $R_{1D}$ is $CH_2$, wherein $R_{1B}$, $R_{1D}$ and the atoms to which they are attached form a 5-membered ring;
$R_{1C}$ is hydroxy, thiol, or $BH_3^-$;
$B_1$ is ring b1 or b2

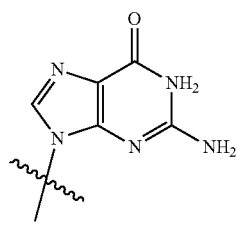

b1

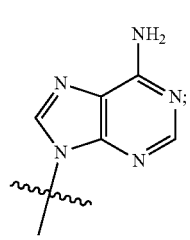

b2

$R_{2B}$ is hydroxy, fluoro or methoxy;
$R_{2C}$ is hydroxy, thiol, or $BH_3^-$;
or an enantiomer, diastereomer, or pharmaceutically acceptable salt form thereof.

13. The method of claim 12, wherein the pharmaceutical composition is a solid oral dosage form.

14. The method of claim 12, wherein the composition is a syrup, an elixir or a suspension.

* * * * *